US011961589B2

(12) United States Patent
Blocker et al.

(10) Patent No.: US 11,961,589 B2
(45) Date of Patent: Apr. 16, 2024

(54) MODELS FOR TARGETED SEQUENCING

(71) Applicant: GRAIL, Inc., Menlo Park, CA (US)

(72) Inventors: Alexander W. Blocker, Mountain View, CA (US); Earl Hubbell, Palo Alto, CA (US); Oliver Claude Venn, San Francisco, CA (US); Qinwen Liu, Fremont, CA (US)

(73) Assignee: GRAIL, LLC, Menlo Park, CA (US)

( * ) Notice: Subject to any disclaimer, the term of this patent is extended or adjusted under 35 U.S.C. 154(b) by 890 days.

(21) Appl. No.: 16/201,912

(22) Filed: Nov. 27, 2018

(65) Prior Publication Data

US 2019/0164627 A1 May 30, 2019

Related U.S. Application Data

(60) Provisional application No. 62/679,347, filed on Jun. 1, 2018, provisional application No. 62/642,301, filed
(Continued)

(51) Int. Cl.
*G16B 20/20* (2019.01)
*C12Q 1/6869* (2018.01)
(Continued)

(52) U.S. Cl.
CPC .......... *G16B 20/20* (2019.02); *C12Q 1/6869* (2013.01); *G06F 17/10* (2013.01); *G16B 5/20* (2019.02);
(Continued)

(58) Field of Classification Search
CPC .......... G16B 20/20; G16B 5/20; G16B 40/00; G16B 15/00; G16B 30/10; G16B 99/00;
(Continued)

(56) References Cited

U.S. PATENT DOCUMENTS

2012/0065081 A1 3/2012 Chee
2014/0066317 A1 3/2014 Talasaz
(Continued)

FOREIGN PATENT DOCUMENTS

CN 104781421 A 7/2015
WO WO 2016/109452 A1 7/2016
(Continued)

OTHER PUBLICATIONS

Larson, Nicholas B., et al. "Improving single-nucleotide polymorphism-based fetal fraction estimation of maternal plasma circulating cell-free DNA using Bayesian hierarchical models." Journal of Computational Biology 25.9 (2018): 1040-1049. (Year: 2018).*
(Continued)

*Primary Examiner* — Jesse P Frumkin
(74) *Attorney, Agent, or Firm* — Fenwick & West LLP

(57) ABSTRACT

A processing system uses a Bayesian inference based model for targeted sequencing or variant calling. In an embodiment, the processing system generates candidate variants of a cell free nucleic acid sample. The processing system determines likelihoods of true alternate frequencies for each of the candidate variants in the cell free nucleic acid sample and in a corresponding genomic nucleic acid sample. The processing system filters or scores the candidate variants by the model using at least the likelihoods of true alternate frequencies. The processing system outputs the filtered candidate variants, which may be used to generate features for a predictive cancer or disease model.

28 Claims, 63 Drawing Sheets

Related U.S. Application Data on Mar. 13, 2018, provisional application No. 62/610,917, filed on Dec. 27, 2017, provisional application No. 62/591,637, filed on Nov. 28, 2017.

(51) Int. Cl.

| | |
|---|---|
| *G06F 17/10* | (2006.01) |
| *G16B 5/20* | (2019.01) |
| *G16B 15/00* | (2019.01) |
| *G16B 30/10* | (2019.01) |
| *G16B 40/00* | (2019.01) |

(52) U.S. Cl.
CPC ............. *G16B 15/00* (2019.02); *G16B 30/10* (2019.02); *G16B 40/00* (2019.02)

(58) Field of Classification Search
CPC ........ G16B 20/00; G16B 5/00; C12Q 1/6869; G06F 17/10
See application file for complete search history.

(56) References Cited

U.S. PATENT DOCUMENTS

| | | | |
|---|---|---|---|
| 2014/0227705 A1 | 8/2014 | Vogelstein et al. | |
| 2015/0044687 A1 | 2/2015 | Schmitt et al. | |
| 2015/0178445 A1 | 6/2015 | Cibulskis et al. | |
| 2015/0324519 A1* | 11/2015 | Liu ........................ | G16H 20/00 702/20 |
| 2017/0058332 A1 | 3/2017 | Kermani et al. | |
| 2017/0211153 A1 | 7/2017 | Kohli et al. | |
| 2020/0105375 A1* | 4/2020 | Pan ........................ | G16B 30/10 |
| 2020/0327954 A1* | 10/2020 | Nance ..................... | C12P 19/34 |
| 2021/0125683 A1* | 4/2021 | Zhou ....................... | G16B 20/20 |

FOREIGN PATENT DOCUMENTS

| | | |
|---|---|---|
| WO | WO 2016/115530 A1 | 7/2016 |
| WO | WO 2017/181146 A1 | 10/2017 |
| WO | WO 2018/161031 A1 | 9/2018 |

OTHER PUBLICATIONS

PCT International Search Report and Written Opinion, PCT Application No. PCT/US2018/062666, dated Apr. 16, 2019, 23 pages.
Genovese, G. et al., "Clonal Hematopoiesis and Blood-Cancer Risk Inferred from Blood DNA Sequence," The New England Journal of Medicine, Nov. 26, 2014, pp. 2477-2487.
Hartman, A. et al., "GRAIL's Approach to Early Cancer Detection," FDA-AACR Liquid Biopsies Workshop, Session II, Conference, Oct. 10, 2017, 16 pages.
Lee, K. et al., "CPEM: Accurate cancer type classification based on somatic alterations using an ensemble of a random forest and a deep neural network," Scientific Reports, vol. 9, No. 1, Nov. 15, 2019, pp. 1-9.
Marquard, A. M. et al., "TumorTracer: a method to identify the tissue of origin from the somatic mutations of a tumor specimen," BMC Medical Genomics 8:58, Oct. 1, 2015, pp. 1-13.
PCT International Search Report and Written Opinion, PCT Application No. PCT/US2019/067297, dated Apr. 29, 2020, pp. 1-17.
Soh, K.P. et al., "Predicting cancer type from tumour DNA signatures," Genome Medicine 9:104, Dec. 1, 2017, pp. 1-11.
Alic, A. et al., "Objective Review of De Novo Stand-Alone Error Correction Methods for NGS Data: Objective Review of De Novo Stand-Alone NGS Correctors," Wiley Interdisciplinary Reviews: Computational Molecular Science, vol. 6, No. 2, Jan. 11, 2016, pp. 111-146.
Cheng, D. et al.,. "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology," The Journal of Colecular Diagnostics 17(3), May 2015, pp. 251-264.
Duncavage, E. et al., "Hybrid Capture and Next-Generation Sequencing Identify Viral Integration Sites from Formalin-Fixed, Paraffin-Embedded Tissue," The Journal of Molecular Diagnostics, vol. 13, No. 3, May 2011, pp. 325-333.
EMBL-EBI, "Variant Effect Predictor," Date Unknown, two pages, [Online] [Retrieved on Mar. 29, 2019] Retrieved from the Internet URL: <https://uswest.ensembl.org/info/docs/tools/vep/index.html?redirect=no>.
Forbes, A. et al., "COSMIC: somatic cancer genetics at high-resolution," Nucleic Acids Research, vol. 45, Nov. 29, 2016, pp. D777-D783.
Newman, A. et al., "An ultrasensitive method for quantitating circulating tumor DNA with broad patient coverage," Nat Med. 20(5), May 2014, pp. 548-554.
PCT Invitation to Pay Additional Fees, PCT Application No. PCT/US2018/062666, dated Feb. 21, 2019, 19 pages.
Pereira, M. et al., "Statistical Learning Formulation of the DNA Base-Calling Problem and its Solution in a Bayesian EM Framework," Discrete Applied Mathematics, vol. 104, No. 1-3, Aug. 15, 2000, pp. 229-258.
Ptashkin, R. et al., "Prevalence of Clonal Hematopoiesis Mutations in Tumor-Only Clinical Genomic Profiling of Solid Tumors," JAMA Oncol. Nov. 2018;4(11), pp. 1589-1593.
Ciniselli, C.M., "Identification of Circulating Biomarkers for the Early Diagnosis of Colorectal Cancer: Methodological Aspects," Dottorato di Ricerca in Epidemiologia, Ambiente e Sanita Pubblica Curriculum in Biostatistica ed Epidemiologia (doctoral thesis), Cicio XXIX, 2016, pp. 1-92.
Japan Patent Office, Office Action, JP Patent Application No. 2020-529278, dated Aug. 30, 2022, 14 pages.
Kang, S. et al., "CancerLocator: non-invasive cancer diagnosis and tissue-of-origin prediction using methylation profiles of cell-free DNA," Genome Biology 18(53), Mar. 24, 2017, pp. 1-12.
Kirkizlar, E. et al., "Detection of Clonal and Subclonal Copy-Number Variants in Cell-Free DNA from Patients with Breast Cancer Using a Massively Multiplexed PCR Methodology," Transitional Oncology, vol. 8, No. 5, Oct. 2015, pp. 407-416.
Kurachic, F., "Memory Change for MacBook Pro (13-inch, Mid 2012) CPU, Memory, and HD," Sep. 29, 2017, 15 pages, [Online] [Retrieved on Aug. 19, 2022] Retrieved from the Internet <URL: https://www.kurachic.jp/column/1826/>.
Starkweather, J. et al., "Multinomial Logistic Regression," University of North Texas, 2011, pp. 1-6, [Online] Retrieved from the Internet <URL: https://it.unt.edu/sites/default/files/mlr_jds_aug2011.pdf>.
Taiwan Intellectual Property Office, Office Action, TW Patent Application No. 107142461, dated Dec. 6, 2022, seven pages (with English translation of search report).
United States Office Action, U.S. Appl. No. 16/719,938, dated Dec. 6, 2022, 15 pages.
China National Intellectual Property Administration, Office Action, CN Patent Application No. 201880076840.2, dated Jan. 4, 2023, 12 pages.
Japan Patent Office, Office Action, JP Patent Application No. 2020-529278, dated Apr. 4, 2023, 11 pages.
Dietrich, D. et al., "Performance evaluation of the DNA methylation biomarker SHOX2 for the aid in diagnosis of lung cancer based on the analysis of bronchial aspirates," International Journal of Oncology 40, Nov. 16, 2011, pp. 825-832.
Nikolaidis, G. et al., "DNA methylation biomarkers offer improved diagnostic efficiency in lung cancer," Cancer Research 72(22), Nov. 15, 2012, pp. 5692-5701.
United States Office Action, U.S. Appl. No. 16/719,938, dated Jul. 31, 2023, 17 pages.
Van De Donk, Nwcj et al., "Interference of daratumumab in monitoring multiple myeloma patients using serum immunofixation electrophoresis can be abrogated using the daratumumab IFE reflex assay (DIRA)," Clinical Chemistry and Laboratory Medicine 54(6), Jan. 21, 2016, pp. 1105-1109.

\* cited by examiner

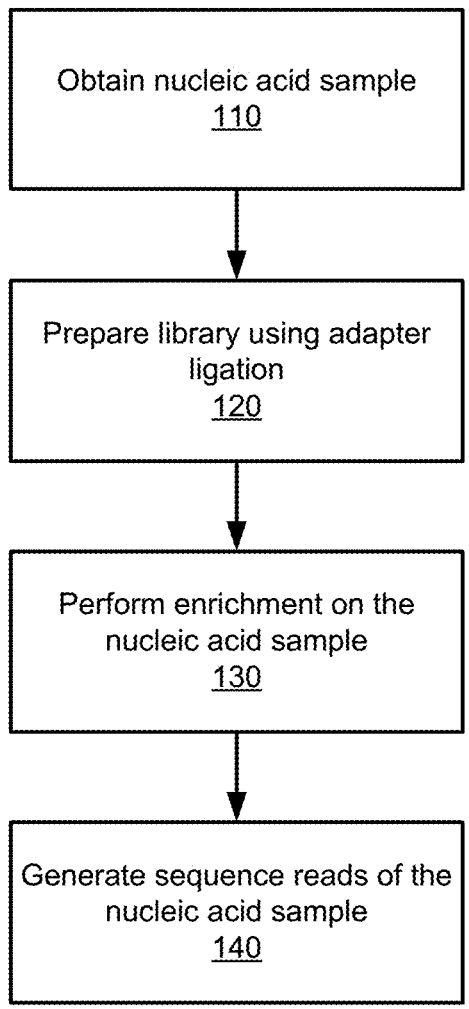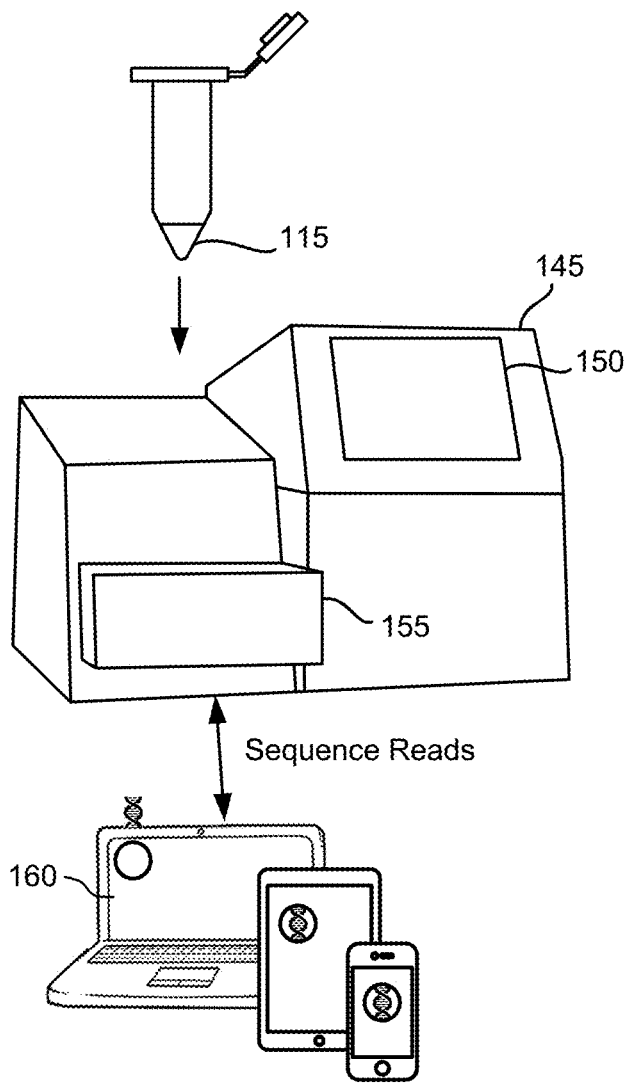
FIG. 1A

| Study | Subject type | Threshold | | | Joint Model | |
|---|---|---|---|---|---|---|
| | | $PPA_{tumor}$ | $PPA_{cfDNA}$ | $PPA_{tumor}$ | $PPA_{tumor}$ | $PPA_{tumor}$ |
| A | Breast | 0 | 0 | 0 | 0 | 0 |
| A | Healthy | NA | 0 | NA | NA | NA |
| A | Lung | 0.14 | 0.12 | 0.12 | 0.12 | 0.22 |
| B | Breast | 0.75 | 0.12 | 0.73 | 0.73 | 0.15 |
| B | Healthy | 0.71 | 0.44 | 0.69 | 0.69 | 0.56 |
| B | Lung | 0.72 | 0.24 | 0.7 | 0.7 | 0.34 |

Determine a probability that the true alternate frequency of a cell free nucleic acid sample is greater than a function of a true alternate frequency of a genomic nucleic acid sample
2010

↓

Probability less than a threshold probability?
2020 — NO → Candidate variant likely not blood-derived

YES ↓

Alternate depth of the gDNA sample significantly same as zero?
2030 — NO → Positive evidence that candidate variant is blood-derived

YES ↓

Determine a gDNA depth quality score of sequence reads of the genomic nucleic acid sample
2040

↓

Determine a ratio of the cell free nucleic acid sample and the genomic nucleic acid sample
2050

↓ gDNA depth quality score greater than or equal to threshold score and ratio less than threshold ratio?
2060 — NO → Uncertain evidence that candidate variant is blood-derived

YES ↓

Determine that a candidate variant is likely associated with a nucleotide mutation of the genomic nucleic acid sample
2070

FIG. 20

| Somatic | Associated with gDNA? | | |
|---|---|---|---|
| | Definitively "Blood" | Likely "Bloodier" | Uncertain "Bloodish" |
| 15216 | 23805 | 1360 | 2607 |

FIG. 21A

| Somatic | Associated with gDNA? | | |
|---|---|---|---|
| | Definitively "Blood" | Likely "Bloodier" | Uncertain "Bloodish" |
| 1914 | 7797 | 451 | 714 |

| | No Edge Variant Filter | Simple Edge Variant Filter | Sample Specific Edge Variant Filter |
|---|---|---|---|
| Breast Cancer | 9.5% | 11% | 9.8% |
| Lung Cancer | 45% | 49% | 47% |
| Prostate Cancer | 22% | 27% | 27% |

(Detected Variants in cfDNA and tissue) / (Detected Variants in cfDNA)

FIG. 30

| | $\frac{\text{(Detected Variants in cfDNA and tissue)}}{\text{(Detected Variants in tissue)}}$ | | |
|---|---|---|---|
| | No Edge Variant Filter | Simple Edge Variant Filter | Sample Specific Edge Variant Filter |
| Breast Cancer | 73% | 69% | 73% |
| Lung Cancer | 73% | 70% | 73% |
| Prostate Cancer | 76% | 71% | 76% |

FIG. 31

|  | Cancers | | | | | Non-cancer | |
|---|---|---|---|---|---|---|---|
|  | Breast | Lung | Prostate | Colorectal | Others | NC | NS <35 yo |
| Total | 410 | 127 | 74 | 52 | 321 | 580 | 169 |
| Age, Mean +/- SD | 58 +/- 13 | 67 +/- 9 | 64 +/- 8 | 60 +/- 11 | 62 +/- 12 | 60 +/- 13 | 28 +/- 4 |
| Sex, N (%) | | | | | | | |
| Female | 410 (100) | 69 (54) | 0 (0) | 28 (54) | 190 (59) | 452 (78) | 109 (64) |
| Male | 0 (0) | 58 (46) | 74 (100) | 24 (46) | 131 (41) | 128 (22) | 60 (36) |
| Race/Ethnicity, N (%) | | | | | | | |
| Asian | 2 (0.5) | 4 (3.1) | 1 (1.4) | 0 (0.0) | 3 (0.9) | 2 (0.3) | 5 (3.0) |
| Black, African Am | 32 (7.8) | 6 (4.7) | 9 (12.2) | 0 (0.0) | 20 (6.2) | 47 (8.1) | 20 (11.8) |
| Hispanic | 20 (4.9) | 4 (3.1) | 2 (2.7) | 3 (5.8) | 17 (5.3) | 29 (5.0) | 19 (11.2) |
| White, non-Hispanic | 351 (85.6) | 112 (88.2) | 61 (82.4) | 48 (92.3) | 274 (85.4) | 489 (84.3) | 125 (74.0) |
| Other/unknown | 5 (1.2) | 1 (0.8) | 1 (1.4) | 1 (1.9) | 7 (2.2) | 13 (2.2) | 0 (0.0) |

FIG. 33A

|  | Breast | Lung | Prostate | Colorectal | Others |
|---|---|---|---|---|---|
| Method of Dx | | | | | |
| Dx by Screening | 237 (58) | 23 (18) | 67 (91) | 16 (31) | 11 (3) |
| Dx by Symptom | 173 (42) | 104 (82) | 7 (9) | 36 (69) | 310 (97) |
| Overall Clinical Stage | | | | | |
| 0 | 51 (12.4) | 1 (0.8) | 0 (0.0) | 1 (1.9) | 5 (1.6) |
| I | 169 (41.2) | 23 (18.1) | 17 (23.0) | 5 (9.6) | 88 (27.4) |
| II | 126 (30.7) | 13 (10.2) | 49 (66.2) | 8 (15.4) | 51 (15.9) |
| III | 50 (12.2) | 40 (31.5) | 3 (4.1) | 16 (30.8) | 58 (18.1) |
| IV | 6 (1.5) | 47 (37.0) | 4 (5.4) | 19 (36.5) | 88 (27.4) |
| Non-informative | 8 (2.0) | 3 (2.4) | 1 (1.4) | 3 (5.8) | 31 (9.7) |
| Clinical N Stage | | | | | |
| N0 | 278 (68) | 37 (29) | 42 (57) | 15 (29) | 91 (28) |
| N1 | 67 (16) | 13 (10) | 3 (4) | 19 (37) | 46 (14) |
| N2 | 11 (3) | 39 (31) | 1 (1) | 7 (13) | 18 (6) |
| N3 | 5 (1) | 14 (11) | 0 (0) | 0 (0) | 4 (1) |
| Nx | 49 (12) | 24 (19) | 28 (38) | 11 (21) | 162 (50) |

FIG. 33C

| Group | mean | median | sd | min | q10 | q90 | max |
|---|---|---|---|---|---|---|---|
| I | 3.121 | 2 | 3.852 | 0 | 0 | 6 | 31 |
| II | 4.707 | 3 | 7.194 | 0 | 1 | 10 | 78 |
| III | 10.24 | 6 | 12.47 | 0 | 1 | 24 | 94 |
| IV | 13.68 | 11 | 15.48 | 0 | 3 | 24.7 | 166 |
| Non-cancer | 2.467 | 2 | 2.012 | 0 | 0 | 5 | 12 |
| YH | 1.089 | 1 | 1.242 | 0 | 0 | 3 | 5 |

FIG. 34E

MODELS FOR TARGETED SEQUENCING

CROSS REFERENCE TO RELATED APPLICATIONS

This application claims the benefit of priority to U.S. Provisional Application No. 62/679,347, filed on Jun. 1, 2018; U.S. Provisional Application No. 62/642,301, filed on Mar. 13, 2018; U.S. Provisional Application No. 62/610,917, filed on Dec. 27, 2017; and U.S. Provisional Application No. 62/591,637, filed on Nov. 28, 2017, all of which are incorporated herein by reference in their entirety for all purposes.

BACKGROUND

1. Field of Art

This disclosure generally relates to models for targeted sequencing, leveraging the models in variant calling and quality control, and statistical analysis of results of physical assays performed on test samples.

2. Description of the Related Art

Computational techniques can be used on DNA sequencing data to identify mutations or variants in DNA that may correspond to various types of cancer or other diseases. Thus, cancer diagnosis or prediction may be performed by analyzing a biological sample such as a tissue biopsy or blood drawn from a subject. Detecting DNA that originated from tumor cells from a blood sample is difficult because circulating tumor DNA (ctDNA) is typically present at low levels relative to other molecules in cell-free DNA (cfDNA) extracted from the blood. The inability of existing methods to identify true positives (e.g., indicative of cancer in the subject) from signal noise diminishes the ability of known and future systems to distinguish true positives from false positives caused by noise sources, which can result in unreliable results for variant calling or other types of analyses. Analyzing cfDNA can be advantageous in comparison to traditional tumor biopsy methods; however, identifying cancer-indicative signals in tumor-derived cfDNA faces distinct challenges, especially for purposes such as early detection of cancer where the cancer-indicative signals are not yet pronounced. As one example, it may be difficult to achieve the necessary sequencing depth of tumor-derived fragments. As another example, errors introduced during sample preparation and sequencing can make accurate identification of rare variants difficult. The combination of these various challenges stand in the way of accurately predicting, with sufficient sensitivity and specificity, characteristics of cancer in a subject through the use of cfDNA obtained from the subject.

A number of different methods have been developed for detecting variants, such as single nucleotide variants (SNVs), in sequencing data. Most conventional methods have been developed for calling variants from DNA sequencing data obtained from a tissue sample. These methods may not be suitable for calling variants from deep sequencing data obtained from a cell free nucleic acid sample.

For non-invasive diagnostic and monitoring of cancer, targeted sequencing data of cell free nucleotides serve as an important bio-source. However, detection of variants in deep sequencing data sets poses distinct challenges: the number of sequenced fragments tend to be several order of magnitude larger (e.g., sequencing depth can be 2,000× or more), debilitating most of the existing variant callers in compute-time and memory usage.

A major challenge to accurate detection of variants is the possibility of damage to sequenced fragments that occur during processing. An example of damage to sequenced fragments can be a nucleotide substitution that occurs naturally or due to assay processing steps. For example, damage can occur due to spontaneous deamination of nucleotide bases or due to end repair errors. Since the damage occurs during processing, existing variant callers may identify these nucleotide base changes as variants in the genome. In other words, this damage can lead to systematic errors and can cause mutations to be falsely identified, e.g., as false positives.

SUMMARY

A processing system uses models for various applications including targeted sequencing, variant calling, quality control, and statistical analysis of physical assays. The processing system generates candidate variants using sequence reads obtained from a sample, which may include blood, a tumor biopsy, or other bodily fluids or substances. Candidate variants may include single nucleotide variants, insertions, or deletions of base pairs. The processing system may determine a likelihood of true alternate frequency for a candidate variant in a cell free nucleic acid sample or a genomic nucleic acid sample. In some use cases, the genomic nucleic acid sample is from white blood cells. The processing system may score or filter the candidate variants using the likelihoods of true alternate frequencies. The processing system outputs the scored or filtered candidate variants, which may be used for variant calling or quality control, for example, by filtering out potential false positives based on estimated noise levels. Additionally, the processing system may generate features from the sequence reads, where the features are input to a predictive cancer or disease model.

The processing system may train and apply a site-specific noise model, also referred to herein as a "Bayesian hierarchical model," "noise model," or "model," for determining likelihoods of true positives in targeted sequencing. The model may use Bayesian inference to determine a rate or level of noise, e.g., indicative of an expected likelihood of certain mutations, per position of a nucleic acid sequence. Moreover, the model may be a hierarchical model that accounts for covariates (e.g., trinucleotide context, mappability, or segmental duplication) and various types of parameters (e.g., mixture components or depth of sequence reads). The model may be trained by Markov chain Monte Carlo sampling from sequence reads of healthy subjects. Therefore, an overall pipeline that incorporates the model can identify true positives at higher sensitivities and filter out false positives. In addition to noise models, the processing system may train and apply a model for classification or prediction of cancer, or other types of diseases, for an individual based on a test sample obtained from the individual.

The processing system may use a filtering process to identify and remove called variants that arise during sample processing. Artifacts can arise from a variety of sources that occur during the processing of cfDNA such as spontaneous cytosine deamination and end repair errors. These artifacts may be referred to by a variety of terms, including edge variants and artifact variants. Called variants that are detected as a result of these artifact processes are not reflective of actual mutations that are present in the genome of a subject. In various embodiments, the filtering process disclosed herein combines at least two analyses. One analysis occurs at the sample level and analyzes the distribution of called variants that are observed across the sample. Another analysis occurs at the variant level and considers each called variant to determine whether that called variant is likely to be a result of an artifact process. Combining these analyses allows a sample specific filtering of individual called variants. As an example scenario, a called variant identified in a sample can be categorized as an edge variant (e.g., resulting from an artifact process) whereas the same called variant identified in a different sample can be categorized as a non-edge variant (e.g., not resulting from an artifact process).

In various embodiments, a method comprises generating a plurality of candidate variants of a cell free nucleic acid sample. The method further comprises determining likelihoods of true alternate frequencies for each of the candidate variants in the cell free nucleic acid sample and in a corresponding genomic nucleic acid sample. The method further comprises filtering the candidate variants at least by a model using the likelihoods of true alternate frequencies. In some use cases, the method may include scoring the candidate variants in addition, or alternatively, to the filtering. The method further comprises outputting the filtered candidate variants.

In one or more embodiments, the method further includes filtering the candidate variants by removing at least one candidate variant associated with a synonymous mutation.

In one or more embodiments, determining the likelihoods of true alternate frequencies further includes, for at least one of the candidate variants, determining first depths and first alternate depths of first sequence reads from a cell free nucleic acid sample of a subject. The method further includes determining second depths and second alternate depths of second sequence reads from a genomic nucleic acid sample of the subject. The method further includes determining a first likelihood of true alternate frequency of the cell free nucleic acid sample by modeling the first alternate depths using a first function parameterized by the first depths and the true alternate frequency of the cell free nucleic acid sample. The method further includes determining a second likelihood of true alternate frequency of the genomic nucleic acid sample by modeling the second alternate depths using a second function parameterized by the second depths and the true alternate frequency of the genomic nucleic acid sample. The model filters the candidate variants at least by determining, using the first likelihood, the second likelihood, and one or more parameters, a probability that the true alternate frequency of the cell free nucleic acid sample is greater than a function of the true alternate frequency of the genomic nucleic acid sample.

In one or more embodiments, the first function is a Poisson distribution function parameterized by a product of one of the first depths and the true alternate frequency of the cell free nucleic acid sample. The second function is another Poisson distribution function parameterized by another product of one of the second depths and the true alternate frequency of the genomic nucleic acid sample.

In one or more embodiments, the probability represents a confidence level that (e.g., nucleotide) mutations from the first sequence reads from the cell free nucleic acid sample are not found in the second sequence reads from the genomic nucleic acid sample of the subject.

In one or more embodiments, the further includes, responsive to determining that the probability is greater than one of the one or more parameters, determining that at least some (e.g., nucleotide) mutations from the first sequence reads from the cell free nucleic acid sample are not found in the second sequence reads from the genomic nucleic acid sample of the subject.

In one or more embodiments, determining the probability includes determining the probability that the true alternate frequency of the cell free nucleic acid sample is greater than the true alternate frequency of the genomic nucleic acid sample multiplied by one of the one or more parameters.

In one or more embodiments, determining the probability includes determining a joint likelihood of the first likelihood and the second likelihood, where the first likelihood and the second likelihood are conditionally independent given the first sequence reads and the second sequence reads.

In one or more embodiments, determining the probability comprises numerically approximating a joint likelihood of the first likelihood and the second likelihood by determining a cumulative sum of one of the first and second likelihoods, and determining an integral of the other of the first and second likelihoods.

In one or more embodiments, the one or more parameters includes a first parameter determined using a third function taking as input an alternate frequency of healthy genomic nucleic acid samples.

In one or more embodiments, the third function is defined by criteria to guard against loss of heterozygosity events in sequence reads.

In one or more embodiments, the third function is a non-linear function.

In one or more embodiments, the criteria indicates a value of 3 for the first parameter and a lower threshold value of $\frac{1}{3}$ for the alternate frequency of the healthy genomic nucleic acid samples.

In one or more embodiments, the one or more parameters includes a second parameter. The first and second parameters are determined empirically by cross-validating with sets of cell free nucleic acid samples and genomic nucleic acid samples of a plurality of individuals.

In one or more embodiments, the first parameter has a value between 1 and 5, inclusive, and the second parameter has another value between 0.5 and 1.

In one or more embodiments, the cross-validating includes applying candidate parameter values derived using samples associated with a plurality of types of diseases to test another sample associated with a different type of disease.

In one or more embodiments, the method further includes determining a first noise level of (e.g., nucleotide) mutations with respect to healthy cell free nucleic acid samples using a third function parameterized by first parameters, where the first likelihood of true alternate frequency of cell free nucleic acid of the subject is determined further using the first noise level. The method further includes determining a second noise level of (e.g., nucleotide) mutations with respect to healthy genomic nucleic acid samples using a fourth function parameterized by second parameters, where the second likelihood of true alternate frequency of genomic nucleic acid of the subject is determined further using the second noise level.

In one or more embodiments, modeling the first alternate depths includes adding the first noise level to an output of the first function, and modeling the second alternate depths includes adding the second noise level to another output of the second function.

In one or more embodiments, the first and second parameters represent parameters of distributions that encode noise levels of (e.g., nucleotide) mutations with respect to a given position of a sequence read.

In one or more embodiments, the third and fourth functions are each a negative binomial function parameterized by a mean rate and dispersion parameter.

In one or more embodiments, the third and fourth functions are a same type of function and parameterized by same types of parameters.

In one or more embodiments, the first parameters are derived using a first model trained using a set of cell free nucleic acid samples, and the second parameters are derived using a second model trained using a set of genomic nucleic acid samples.

In one or more embodiments, the set of genomic nucleic acid samples are from white blood cells.

In one or more embodiments, the first and second models are Bayesian Hierarchical models.

In one or more embodiments, the first and second models are a same type of model.

In one or more embodiments, the method further includes collecting or having collected the cell free nucleic acid sample from a blood sample of the subject. The method further includes performing enrichment on the cell free nucleic acid sample to generate the first sequence reads.

In one or more embodiments, the first sequence reads are obtained from a sample of blood, whole blood, plasma, serum, urine, cerebrospinal fluid, fecal, saliva, tears, a tissue biopsy, pleural fluid, pericardial fluid, or peritoneal fluid of the subject.

In one or more embodiments, the first sequence reads are obtained from an isolate of cells from blood including at least CD4+ cells of the subject.

In one or more embodiments, the second sequence reads are obtained from tumor cells obtained from a tumor biopsy of the subject.

In one or more embodiments, the second sequence reads are obtained from white blood cells of the subject.

In one or more embodiments, the method further includes determining that a candidate variant of the first sequence reads from the cell free nucleic acid sample is associated with a nucleotide mutation of the genomic nucleic acid sample responsive to: determining that the probability is less than a threshold probability, and determining that one of the second alternate depths of the second sequence reads from the genomic nucleic acid sample is greater than zero.

In one or more embodiments, the threshold probability equals 0.8.

In one or more embodiments, the method further includes, for a candidate variant of the first sequence reads from the cell free nucleic acid sample, responsive to (i) determining that the probability is less than a threshold probability and (ii) determining that one of the second alternate depths of the second sequence reads from the genomic nucleic acid sample associated with the candidate variant is equal to zero: determining a ratio using the first depths, the first alternate depths, the second depths, and the second alternate depths, and determining that the candidate variant is likely associated with a (e.g., nucleotide) mutation of the genomic nucleic acid sample responsive to at least determining that the ratio is less than a threshold ratio.

In one or more embodiments, at least one of the one or more parameters is determined for the candidate variant based on the determination that the candidate variant is likely associated with the (e.g., nucleotide) mutation of the genomic nucleic acid sample.

In one or more embodiments, the method further includes determining a first set of one or more parameters corresponding to the candidate variant. The method further includes applying a first filter to the candidate variant using the first set of one or more parameters. The method further includes, responsive to determining that another candidate variant is unlikely associated with another (e.g., nucleotide) mutation of the genomic nucleic acid sample, determining a second set of one or more parameters corresponding to the another candidate variant. The method further includes applying a second filter to the another candidate variant using the second set of one or more parameters, the second filter having a stricter filtering criterion than that of the first filter.

In one or more embodiments, the method further includes determining a gDNA depth quality score using the second alternate depths of the second sequence reads. Where determining that the candidate variant is likely associated with the (e.g., nucleotide) mutation is further responsive to determining that the gDNA depth quality score is greater than or equal to a threshold score.

In one or more embodiments, the threshold score is one.

In one or more embodiments, the method further includes determining to filter a candidate variant of the first sequence reads from the cell free nucleic acid sample by determining that the first sequence reads satisfy at least one of a plurality of criteria.

In one or more embodiments, determining whether the first sequence reads satisfy at least one of the plurality of criteria includes determining that the candidate variant is an edge variant artifact.

In one or more embodiments, determining whether the first sequence reads satisfy at least one of the plurality of criteria includes determining that one of the first depths of the first sequence reads is less than a threshold depth.

In one or more embodiments, determining whether the first sequence reads satisfy at least one of the plurality of criteria includes determining that a frequency of (e.g., nucleotide) mutations in the first sequence similar to one or more germline mutations is greater than a threshold frequency, and determining that the (e.g., nucleotide) mutations are located at positions associated with germline mutations.

In one or more embodiments, the method further comprises generating values of one or more features using the filtered sequence reads. The method further comprises inputting the values of the one or more features into a predictive cancer model to generate a cancer prediction for the subject, the predictive cancer model transforming the values of the one or more features to the cancer prediction for the subject through a function comprising learned weights. The method further comprises providing the cancer prediction for the subject.

In one or more embodiments, the one or more features comprise one or more of a total number of somatic variants, a total number of nonsynonymous variants, a total number of synonymous variants, a presence or absence of somatic variants per gene in a gene panel, a presence or absence of somatic variants for particular genes known to be associated with cancer, an allele frequency of a somatic variant per gene in a gene panel, a ranked order according to AF of somatic variants, and an allele frequency of a somatic variant per category.

In one or more embodiments, filtering the candidate variants by the model includes, for a candidate variants of the plurality of candidate variants, determining a probability that a true alternate frequency of the candidate variant in the cell free nucleic acid sample is greater than a function of a true alternate frequency of the candidate variant in the corresponding genomic nucleic acid sample. The filtering further includes determining that the probability is less than a threshold probability. The filtering further includes determining that an alternate depth of the candidate variant in the genomic nucleic acid sample is greater than a threshold depth. The filtering further includes determining a ratio using a depth and alternate depth of the cell free nucleic acid sample and another depth and alternate depth of the genomic nucleic acid sample. The filtering further includes determining a gDNA depth quality score using the alternate depth of the genomic nucleic acid sample. The filtering further includes determining that the candidate variant is likely associated with a (e.g., nucleotide) mutation of the genomic nucleic acid sample responsive to: determining that the ratio is less than a threshold ratio, and determining that the gDNA depth quality score is greater than or equal to a threshold score.

In various embodiments, a method comprises determining first depths and first alternate depths of first sequence reads from a cell free nucleic acid sample of a subject. The method further comprises determining second depths and second alternate depths of second sequence reads from a genomic nucleic acid sample of the subject. The method further comprises determining a first likelihood of true alternate frequency of the cell free nucleic acid sample by modeling the first alternate depths using a first function parameterized by the first depths and the true alternate frequency of the cell free nucleic acid sample. The method further comprises determining a second likelihood of true alternate frequency of the genomic nucleic acid sample by modeling the second alternate depths using a second function parameterized by the second depths and the true alternate frequency of the genomic nucleic acid sample. The method further comprises filtering candidate variants of the subject at least by determining, using the first likelihood, the second likelihood, and one or more parameters, a probability that the true alternate frequency of the cell free nucleic acid sample is greater than a function of the true alternate frequency of the genomic nucleic acid sample. The method further comprises outputting the filtered candidate variants.

The processing system may conduct a sample-specific analysis or a variant-specific analysis in view of distributions that are generated using previously categorized edge variants and previously categorized non-edge variants obtained from prior samples (e.g., training samples). For example, a first distribution describes the distribution of features of previously categorized edge variants whereas a second distribution describe the distribution of features of previously categorized non-edge variants. Features can be related to a location of the mutated nucleotide base across sequence reads of an edge variant or non-edge variant. For example, one particular feature can be a median distance from an edge of a sequence read that a mutated nucleotide base is detected across the sequence reads.

In various embodiments, the sample-specific analysis employs a sample-specific rate prediction model that determines a predicted rate of artifacts in the sample. For example, the sample-specific analysis may include performing a likelihood estimation to determine a predicted rate of edge variants in the sample. Here, the predicted rate may best explains the distribution of called variants observed across the sample in view of the first distribution and the second distribution. A high predicted rate indicates that the distribution of called variants observed across the sample is more similar to the first distribution that describes features of known edge variants. In other words, a large proportion of called variants observed across the sample are likely due to artifact processes. An example result like this suggests the use of a more aggressive filtering process to identify and eliminate edge variants in the sample. On the other hand, a low predicted rate indicates that the distribution of called variants observed across the sample is more similar to the second distribution that describes features of known non-edge variants. In other words, a small proportion of called variants observed across the sample are likely due to artifact processes. An example result like this suggests the use of a less aggressive filtering process to identify and eliminate edge variants in the sample.

In various embodiments, the variant specific analysis employs an edge variant prediction model that analyzes the features of the specific called variant in view of the first and second distributions. The edge variant prediction model outputs an artifact score that represents the likelihood that the called variant is a result of a processing artifact as well as a non-artifact score that represents the likelihood that the called variant is a non-edge variant. For each called variant, the sample-specific predicted rate is combined with the artifact score and non-artifact score for the called variant. Therefore, the called variant is identified as an edge variant or a non-edge variant by considering both the sample-specific analysis and variant specific analysis. Edge variants can be filtered out whereas non-edge variants are kept.

In various embodiments, a method comprises generating a plurality of candidate variants of a cell free nucleic acid sample. The method further comprises determining likelihoods of true alternate frequencies for each of the candidate variants in the cell free nucleic acid sample and in a corresponding genomic nucleic acid sample. The method further comprises filtering the candidate variants at least by a model using the likelihoods of true alternate frequencies. The method further comprises filtering the candidate variants by determining, for each of the candidate variants, an edge variant probability indicating probability that the candidate variant is an edge variant. The method further comprises outputting the filtered candidate variants.

In various embodiments, filtering the candidate variants includes receiving alternative alleles located on sequence reads, the sequence reads obtained from a plurality of positions in a genome. The method further includes determining a predicted rate of edge variants for the cell free nucleic acid sample based on the received alternative alleles. The method further includes, for each of a subset of the plurality of positions: extracting features from sequence reads obtained from the position; applying the extracted features as input to a trained model to obtain an artifact score for the position and a non-artifact score for the position, the artifact score reflecting a likelihood that alternative alleles located on sequence reads obtained from the position are a result of a processing artifact, the non-artifact score reflecting a likelihood that alternative alleles located on sequence reads obtained from the position are not a result of a processing artifact; generating the edge variant probability for the position by combining the artifact score for the position, the non-artifact score for the position, and the predicted rate of artifacts for the cell free nucleic acid sample; and reporting one of the candidate variants at the position as an edge variant based on the edge variant probability.

In one or more embodiments, the edge variants for the cell free nucleic acid sample are due to spontaneous deamination of portions of one or more of the sequence reads.

In one or more embodiments, determining the predicted rate of edge variants for the cell free nucleic acid sample includes performing a likelihood based estimation in view of the received alternative alleles to generate an estimator, and selecting the predicted rate of edge variants based on the maximum likelihood estimator.

In one or more embodiments, the likelihood based estimation is further performed in view of a first distribution generated from sequence reads categorized into an artifact category.

In one or more embodiments, the likelihood based estimation is further performed in view of a second distribution generated from sequence reads categorized into a non-artifact category.

In one or more embodiments, one of the features extracted from the sequence reads of the position is a median distance between locations of alternative alleles on a subset of the sequencing reads and edges of the subset of the sequencing reads.

In one or more embodiments, one of the features extracted from the sequence reads of the position is a significance score representing a difference between 1) a first median distance between locations of alternative alleles on a first subset of the sequencing reads and edges of the sequencing reads in the first subset and 2) a second median distance between locations of reference alleles on a second subset of the sequencing reads and edges of the sequencing reads in the second subset.

In one or more embodiments, one of the features extracted from the sequence reads of the position is an allele fraction representing a fraction of sequence reads that contain the alternative allele that cross a position.

In one or more embodiments, reporting the called variant as the edge variant based on the edge variant probability includes comparing the edge variant probability to a threshold value, and reporting the called variant as the edge variant based on the comparison.

In one or more embodiments, positions in the genome that are included in the subset of the plurality of positions are determined by, for each position in the plurality, identifying a mutation type of a called variant corresponding to the position, and determining whether the mutation type of the called variant is one of a cytosine to thymine or a guanine to adenine base substitution.

In one or more embodiments, the trained model is trained by: receiving training data comprising alternative alleles located on training sequence reads, the training sequence reads obtained from a plurality of positions in a genome; categorizing each of the training sequence reads into two or more categories based on characteristics of the alternative allele located on the training sequence read; for each of the two or more categories of training variants, extracting features from training sequence reads categorized in the category, and generating a distribution based on the extracted features.

In one or more embodiments, the characteristics of the training sequence read comprise a type of nucleotide base mutation of the alternate read, and where categorizing each of the training sequence reads into two or more categories comprises categorizing each training sequence read into one of an artifact category or a non-artifact category based on the type of nucleotide base mutation of the alternative allele on the training sequence read.

In one or more embodiments, training sequence reads categorized into the artifact category each include an alternate read that is either a cytosine to thymine mutation or a guanine to adenine mutation.

In one or more embodiments, training sequence reads categorized into the artifact category each include an alternative allele located within a threshold distance from an edge of the training sequencing read.

In one or more embodiments, training sequence reads categorized into the non-artifact category each include an alternative allele that is either located outside a threshold distance from an edge of the training sequencing read or is a base substitution other than a cytosine to thymine mutation or a guanine to adenine mutation.

Embodiments disclosed herein describe a method for detecting the presence of cancer in a subject, the method comprising: obtaining sequencing data generated from a plurality of cell-free nucleic acids in a test sample from the subject, wherein the sequencing data comprises a plurality of sequence reads determined from the plurality of cell-free nucleic acids; analyzing, using a suitable programed computer, the plurality of sequence reads to identify one or more sequencing based features; detecting the presence of cancer based on the analysis of the one or more features, wherein the presence of cancer is detected with a specificity of at least about 95% and a sensitivity of at least about 30% sensitivity.

In some embodiments, the presence of cancer is detected with a specificity of at least about 95% and a sensitivity of at least about 50% sensitivity. In some embodiments, the presence of cancer is detected with a specificity of at least about 95% and a sensitivity of at least about 60% sensitivity. In some embodiments, the presence of cancer is detected with a specificity of at least about 95% and a sensitivity of at least about 70% sensitivity. In some embodiments, the presence of cancer is detected with a specificity of at least about 95% and a sensitivity of at least about 80% sensitivity. In some embodiments, the presence of cancer is detected with a specificity of at least about 95% and a sensitivity of at least about 90% sensitivity. In some embodiments, the presence of cancer is detected with a specificity of at least about 95% and a sensitivity of at least about 95% sensitivity. In some embodiments, the presence of cancer is detected with a specificity of at least about 99% and a sensitivity of at least about 35% sensitivity. In some embodiments, the presence of cancer is detected with a specificity of at least about 95% and a sensitivity of at least about 40% sensitivity. In some embodiments, the presence of cancer is detected with a specificity of at least about 95% and a sensitivity of at least about 45% sensitivity. In some embodiments, the presence of cancer is detected with a specificity of at least about 96%, 97%, 98%, 99%, 99.5%, 99.8%, or 99.9%. In some embodiments, the presence of cancer is detected with a specificity of at least about 55%, 60%, 65%, 70%, 75%, 80%, 85%, 90%, 91%, 92%, 93%, 94%, or 95%.

Embodiments disclosed herein further describe a method for detecting the presence of cancer in an asymptomatic subject, the method comprising: obtaining sequencing data generated from a plurality of cell-free nucleic acids in a test sample from an asymptomatic subject; analyzing, using a suitable programed computer, the sequencing data to identify one or more sequencing based features; detecting the presence of cancer based on the analysis of the one or more features, wherein the area under the curve (AUC) of a receiver operating characteristic (ROC) for the presence of cancer is greater than 0.60. In some embodiments, the AUC is greater than 0.65, 0.70, 0.75 0.80, 0.85, 0.90, 0.95, 0.97, 0.98, or 0.99.

Embodiments disclosed herein further describe a method for detecting the presence of cancer in an asymptomatic subject, the method comprising: obtaining sequencing data generated from a plurality of cell-free nucleic acids in a test sample from an asymptomatic subject; analyzing, using a suitable programed computer, the sequencing data to identify one or more sequencing based features; detecting the presence of cancer based on the analysis of the one or more features, wherein the presence of cancer is detected with an estimated positive predictive value of at least about 30%.

In some embodiments, the presence of cancer is detected with an estimated positive predictive value of at least 35%, 40%, 45%, 50%, 55%, 60%, 65%, 70%, or 75%. In some embodiments, the method detects two or more different types of cancer. In some embodiments, the method detects three or more different types of cancer. In some embodiments, the method detects five or more different types of cancer. In some embodiments, the method detects ten or more different types of cancer. In some embodiments, the method detects twenty or more different types of cancer. In some embodiments, the two or more different types of cancer are selected from breast cancer, lung cancer, prostate cancer, colorectal cancer, renal cancer, uterine cancer, pancreas cancer, esophageal cancer, lymphoma, head and neck cancer, ovarian cancer, hepatobiliary cancer, melanoma, cervical cancer, multiple myeloma, leukemia, thyroid cancer, bladder cancer, gastric cancer, anorectal cancer, and any combination thereof.

In some embodiments, the subject is asymptomatic. In some embodiments, the cell-free nucleic acids comprise cell-free DNA (cfDNA). In some embodiments, the sequence reads are generated from a next generation sequencing (NGS) procedure. In some embodiments, the sequence reads are generated from a massively parallel sequencing procedure using sequencing-by-synthesis.

In some embodiments, the one or more features are derived from at least a small variant sequencing assay on the plurality of cell-free nucleic acids in the test sample.

In some embodiments, the small variant sequencing assay is a targeted sequencing assay, and wherein the sequence data is derived from a targeted panel of genes. In some embodiments, the targeted panel of genes comprises between 2 and 10,000 genes. In some embodiments, detecting the presence of cancer based on the analysis of one or more features determined from the small variant sequencing assay. In some embodiments, the small variant sequencing assay features comprise one or more of a total number of somatic variants, a total number of nonsynonymous variants, total number of synonymous variants, a presence/absence of somatic variants per gene, a presence/absence of somatic variants for particular genes that are known to be associated with cancer, an allele frequency of a somatic variant per gene, order statistics according to AF of somatic variants, and classification of somatic variants that are known to be associated with cancer based on their allele frequency. In some embodiments, the method further comprises obtaining sequence data of genomic DNA from one of more white blood cells of the subject, wherein the sequencing data comprises a plurality of sequence reads determined from the genomic DNA and wherein the analysis comprises comparing the sequence data for cell-free nucleic acids form the subject with the sequence data of DNA from the one or more white blood cells of the subject to identify one or more tumor-derived small variant sequencing assay features.

In some embodiments, the detected cancer is a stage I cancer. In some embodiments, the detected cancer is a stage II cancer. In some embodiments, the detected cancer is a stage III cancer. In some embodiments, the detected cancer is a stage IV cancer. In some embodiments, the detected cancer is breast cancer, lung cancer, colorectal cancer, ovarian cancer, uterine cancer, melanoma, renal cancer, pancreatic cancer, thyroid cancer, gastric cancer, hepatobiliary cancer, esophageal cancer, prostate cancer, lymphoma, multiple myeloma, head and neck cancer, bladder cancer, cervical cancer, or any combination thereof. In some embodiments, the method further comprises classifying breast cancer as HR positive, HER2 overexpression, HER2 amplified, or triple negative, based on analysis of the sequence reads from the test sample.

In some embodiments, the analysis further comprises detecting the presence of one or more viral-derived nucleic acids in the test sample and wherein the detection of cancer is based, in part, on detection of the one or more viral nucleic acids. For example, in one embodiment, the one or more features may include a presence/absence of a viral-derived nucleic acid or a viral load determined from viral-derived nucleic acids. In some embodiments, the one or more viral-derived nucleic acids are selected from the group consisting of human papillomavirus, Epstein-Barr virus, hepatitis B, hepatitis C, and any combination thereof.

In some embodiments, the test sample is a blood, plasma, serum, urine, cerebrospinal fluid, fecal matter, saliva, pleural fluid, pericardial fluid, cervical swab, saliva, or peritoneal fluid sample.

BRIEF DESCRIPTION OF DRAWINGS

FIG. 1A is flowchart of a method for preparing a nucleic acid sample for sequencing according to one embodiment.

FIG. 16 is a diagram of sensitivity and specificity of a joint model according to one embodiment.

FIG. 20 is flowchart of a method for tuning a joint model to process cell free nucleic acid samples and genomic nucleic acid samples according to one embodiment.

FIG. 21A is a table of example counts of candidate variants of cfDNA samples according to an embodiment.

FIG. 21B is a table of example counts of candidate variants of cfDNA samples from healthy individuals according to one embodiment.

FIG. 30 depicts concordant variants called in both solid tumor and in cfDNA following the removal of edge variants using different edge filters as a fraction of the variants called in cfDNA according to one embodiment.

FIG. 31 depicts concordant variants called in both solid tumor and in cfDNA following the removal of edge variants using different edge filters as a fraction of the variants called in solid tumor according to one embodiment.

FIG. 33A is a table describing individuals of a sample set for a cell free genome study according to one embodiment.

FIG. 33C is another table describing the sample set for the cell free genome study of FIG. 33A according to one embodiment.

FIG. 34E is a table of example counts of called variants for samples known to have various types of cancer and at different stages of cancer according to one embodiment.

Figure 1B:
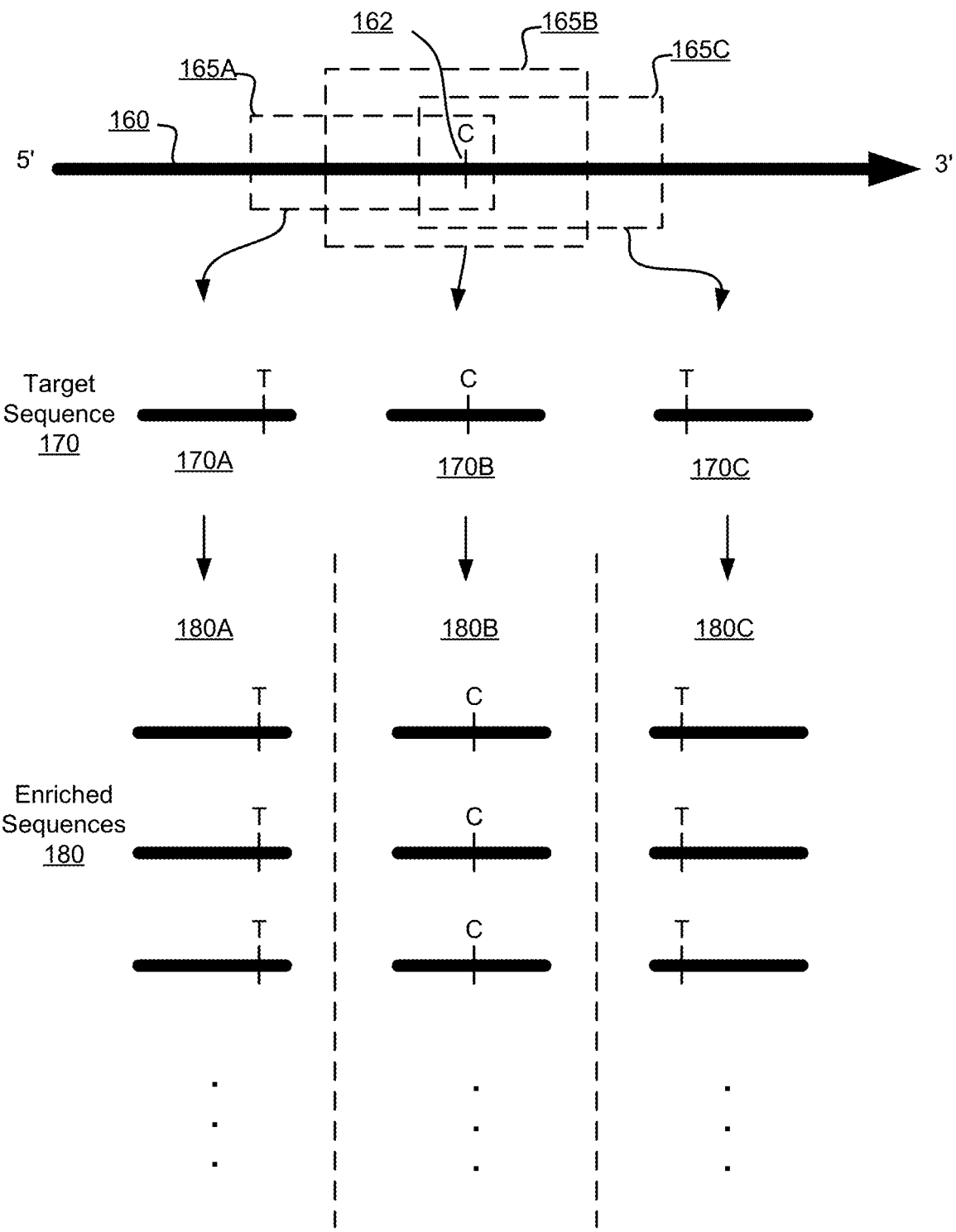
FIG. 1B is a graphical representation of the process for obtaining sequence reads according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Reference will now be made in detail to several embodiments, examples of which are illustrated in the accompanying figures. It is noted that wherever practicable similar or like reference numbers may be used in the figures and may indicate similar or like functionality. For example, a letter after a reference numeral, such as "sequence reads 180A," indicates that the text refers specifically to the element having that particular reference numeral. A reference numeral in the text without a following letter, such as "sequence reads 180," refers to any or all of the elements in the figures bearing that reference numeral (e.g. "sequence reads 180" in the text refers to reference numerals "sequence reads 180A" and/or "sequence reads 180B" in the figures).

I. Definitions

The term "individual" refers to a human individual. The term "healthy individual" refers to an individual presumed to not have a cancer or disease. The term "subject" refers to an individual who is known to have, or potentially has, a cancer or disease.

The term "sequence reads" refers to nucleotide sequences read from a sample obtained from an individual. Sequence reads can be obtained through various methods known in the art.

The term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

The term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

The term "indel" refers to any insertion or deletion of one or more bases having a length and a position (which may also be referred to as an anchor position) in a sequence read. An insertion corresponds to a positive length, while a deletion corresponds to a negative length.

The term "mutation" refers to one or more SNVs or indels.

The term "candidate variant," "called variant," or "putative variant" refers to one or more detected nucleotide variants of a nucleotide sequence, for example, at a position in the genome that is determined to be mutated (i.e., a candidate SNV) or an insertion or deletion at one or more bases (i.e., a candidate indel). Generally, a nucleotide base is deemed a called variant based on the presence of an alternative allele on a sequence read, or collapsed read, where the nucleotide base at the position(s) differ from the nucleotide base in a reference genome. Additionally, candidate variants may be called as true positives or false positives.

The term "true positive" refers to a mutation that indicates real biology, for example, presence of a potential cancer, disease, or germline mutation in an individual. True positives are not caused by mutations naturally occurring in healthy individuals (e.g., recurrent mutations) or other sources of artifacts such as process errors during assay preparation of nucleic acid samples.

The term "false positive" refers to a mutation incorrectly determined to be a true positive. Generally, false positives may be more likely to occur when processing sequence reads associated with greater mean noise rates or greater uncertainty in noise rates.

The term "cell-free nucleic acids" of "cfNAs" refers to nucleic acid molecules that can be found outside cells, in bodily fluids such blood, sweat, urine, or saliva. Cell-free nucleic acids are used interchangeably as circulating nucleic acids.

The term "cell free nucleic acid," "cell free DNA," or "cfDNA" refers to deoxyribonucleic acid fragments that circulate in bodily fluids such blood, sweat, urine, or saliva and originate from one or more healthy cells and/or from one or more cancer cells.

The term "circulating tumor DNA" or "ctDNA" refers to deoxyribonucleic acid fragments that originate from tumor cells or other types of cancer cells, which may be released into an individual's bodily fluids such blood, sweat, urine, or saliva as result of biological processes such as apoptosis or necrosis of dying cells or actively released by viable tumor cells.

The term "circulating tumor RNA" or "ctRNA" refers to ribonucleic acid fragments that originate from tumor cells or other types of cancer cells, which may be released into an individual's bodily fluids such blood, sweat, urine, or saliva as result of biological processes such as apoptosis or necrosis of dying cells or actively released by viable tumor cells.

The term "genomic nucleic acid," "genomic DNA," or "gDNA" refers to nucleic acid including chromosomal DNA that originate from one or more healthy cells.

The term "alternative allele" or "ALT" refers to an allele having one or more mutations relative to a reference allele, e.g., corresponding to a known gene.

The term "sequencing depth" or "depth" refers to a total number of read segments from a sample obtained from an individual at a given position, region, or loci. In some embodiments, the depth refers to the average sequencing depth across the genome or across a targeted sequencing panel.

The term "alternate depth" or "AD" refers to a number of read segments in a sample that support an ALT, e.g., include mutations of the ALT.

The term "reference depth" refers to a number of read segments in a sample that include a reference allele at a candidate variant location.

The term "alternate frequency" or "AF" refers to the frequency of a given ALT. The AF may be determined by dividing the corresponding AD of a sample by the depth of the sample for the given ALT.

The term "variant" or "true variant" refers to a mutated nucleotide base at a position in the genome. Such a variant can lead to the development and/or progression of cancer in an individual.

The term "edge variant" refers to a mutation located near an edge of a sequence read, for example, within a threshold distance of nucleotide bases from the edge of the sequence read.

The term "non-edge variant" refers to a candidate variant that is not determined to be resulting from an artifact process, e.g., using an edge variant filtering method described herein. In some scenarios, a non-edge variant may not be a true variant (e.g., mutation in the genome) as the non-edge variant could arise due to a different reason as opposed to one or more artifact processes.

II. Example Assay Protocol

FIG. 1A is flowchart of a method 100 for preparing a nucleic acid sample for sequencing according to one embodiment. The method 100 includes, but is not limited to, the following steps. For example, any step of the method 100 may comprise a quantitation sub-step for quality control or other laboratory assay procedures known to one skilled in the art.

In step 110, a test sample comprising a plurality of nucleic acid molecules (DNA or RNA) is obtained from a subject, and the nucleic acids are extracted and/or purified from the test sample. In the present disclosure, DNA and RNA may be used interchangeably unless otherwise indicated. That is, the following embodiments for using error source information in variant calling and quality control may be applicable to both DNA and RNA types of nucleic acid sequences. However, the examples described herein may focus on DNA for purposes of clarity and explanation. The nucleic acids in the extracted sample may comprise the whole human genome, or any subset of the human genome, including the whole exome. Alternatively, the sample may be any subset of the human transcriptome, including the whole transcriptome. The test sample may be obtained from a subject known to have or suspected of having cancer. In some embodiments, the test sample may include blood, plasma, serum, urine, fecal, saliva, other types of bodily fluids, or any combination thereof. Alternatively, the test sample may comprise a sample selected from the group consisting of whole blood, a blood fraction, a tissue biopsy, pleural fluid, pericardial fluid, cerebral spinal fluid, and peritoneal fluid. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. In general, any known method in the art can be used to extract and purify cell-free nucleic acids from the test sample. For example, cell-free nucleic acids can be extracted and purified using one or more known commercially available protocols or kits, such as the QIAamp circulating nucleic acid kit (QIAGEN®). If a subject has a cancer or disease, ctDNA in an extracted sample may be present at a detectable level for diagnosis.

In step 120, a sequencing library is prepared. During library preparation, sequencing adapters comprising unique molecular identifiers (UMI) are added to the nucleic acid molecules (e.g., DNA molecules), for example, through adapter ligation (using T4 or T7 DNA ligase) or other known means in the art. The UMIs are short nucleic acid sequences (e.g., 4-10 base pairs) that are added to ends of DNA fragments and serve as unique tags that can be used to identify nucleic acids (or sequence reads) originating from a specific DNA fragment. Following adapter addition, the adapter-nucleic acid constructs are amplified, for example, using polymerase chain reaction (PCR). During PCR amplification, the UMIs are replicated along with the attached DNA fragment, which provides a way to identify sequence reads that came from the same original fragment in downstream analysis. Optionally, as is well known in the art, the sequencing adapters may further comprise a universal primer, a sample-specific barcode (for multiplexing) and/or one or more sequencing oligonucleotides for use in subsequent cluster generation and/or sequencing (e.g., known P5 and P7 sequences for used in sequencing by synthesis (SBS) (ILLUMINA®, San Diego, CA)).

In step 130, targeted DNA sequences are enriched from the library. In accordance with one embodiment, during targeted enrichment, hybridization probes (also referred to herein as "probes") are used to target, and pull down, nucleic acid fragments known to be, or that may be, informative for the presence or absence of cancer (or disease), cancer status, or a cancer classification (e.g., cancer type or tissue of origin). For a given workflow, the probes may be designed to anneal (or hybridize) to a target (complementary) strand of DNA or RNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a gene panel to analyze particular mutations or target regions of the genome (e.g., of the human or another organism) that are suspected to correspond to certain cancers or other types of diseases. Moreover, the probes may cover overlapping portions of a target region. As one of skill in the art would readily appreciate, any known means in the art can be used for targeted enrichment. For example, in one embodiment, the probes may be biotinylated and streptavidin coated magnetic beads used to enrich for probe captured target nucleic acids. See, e.g., Duncavage et al., J Mol Diagn. 13(3): 325-333 (2011); and Newman et al., Nat Med. 20(5): 548-554 (2014). By using a targeted gene panel rather than sequencing the whole genome ("whole genome sequencing"), all expressed genes of a genome ("whole exome sequencing" or "whole transcriptome sequencing"), the method 100 may be used to increase sequencing depth of the target regions, where depth refers to the count of the number of times a given target sequence within the sample has been sequenced. Increasing sequencing depth allows for detection of rare sequence variants in a sample and/or increases the throughput of the sequencing process. After a hybridization step, the hybridized nucleic acid fragments are captured and may also be amplified using PCR.

FIG. 1B is a graphical representation of the process for obtaining sequence reads according to one embodiment. FIG. 1B depicts one example of a nucleic acid segment 160 from the sample. Here, the nucleic acid segment 160 can be a single-stranded nucleic acid segment, such as a single stranded DNA or single stranded RNA segment. In some embodiments, the nucleic acid segment 160 is a double-stranded cfDNA segment. The illustrated example depicts three regions 165A, 165B, and 165C of the nucleic acid segment 160 that can be targeted by different probes. Specifically, each of the three regions 165A, 165B, and 165C includes an overlapping position on the nucleic acid segment 160. An example overlapping position is depicted in FIG. 1B as the cytosine ("C") nucleotide base 162. The cytosine nucleotide base 162 is located near a first edge of region 165A, at the center of region 165B, and near a second edge of region 165C.

In some embodiments, one or more (or all) of the probes are designed based on a gene panel to analyze particular mutations or target regions of the genome (e.g., of the human or another organism) that are suspected to correspond to certain cancers or other types of diseases. By using a targeted gene panel rather than sequencing all expressed genes of a genome, also known as "whole exome sequencing," the method 100 may be used to increase sequencing depth of the target regions, where depth refers to the count of the number of times a given target sequence within the sample has been sequenced. Increasing sequencing depth reduces required input amounts of the nucleic acid sample.

Hybridization of the nucleic acid sample 160 using one or more probes results in an understanding of a target sequence 170. As shown in FIG. 1B, the target sequence 170 is the nucleotide base sequence of the region 165 that is targeted by a hybridization probe. The target sequence 170 can also be referred to as a hybridized nucleic acid fragment. For example, target sequence 170A corresponds to region 165A targeted by a first hybridization probe, target sequence 170B corresponds to region 165B targeted by a second hybridization probe, and target sequence 170C corresponds to region 165C targeted by a third hybridization probe. Given that the cytosine nucleotide base 162 is located at different locations within each region 165A-C targeted by a hybridization probe, each target sequence 170 includes a nucleotide base that corresponds to the cytosine nucleotide base 162 at a particular location on the target sequence 170.

In the example of FIG. 1B, the target sequence 170A and target sequence 170C each have a nucleotide base (shown as thymine "T") that is located near the edge of the target sequences 170A and 170C. Here, the thymine nucleotide base (e.g., as opposed to a cytosine base) may be a result of a random cytosine deamination process that causes a cytosine base to be subsequently recognized as a thymine nucleotide base during the sequencing process. Thus, the C>T SNV for target sequences 170A and 170C may be considered an edge variant because the mutation is located at an edge of target sequences 170A and 170C. A cytosine deamination process can lead to a downstream sequencing artifact that prevents the accurate capture of the actual nucleotide base pair in the nucleic acid segment 160. Additionally, target sequence 170B has a cytosine base that is located at the center of the target sequence 170B. Here, a cytosine base that is located at the center may be less susceptible to cytosine deamination.

After a hybridization step, the hybridized nucleic acid fragments are captured and may also be amplified using PCR. For example, the target sequences 170 can be enriched to obtain enriched sequences 180 that can be subsequently sequenced. In some embodiments, each enriched sequence 180 is replicated from a target sequence 170. Enriched sequences 180A and 180C that are amplified from target sequences 170A and 170C, respectively, also include the thymine nucleotide base located near the edge of each sequence read 180A or 180C. As used hereafter, the mutated nucleotide base (e.g., thymine nucleotide base) in the enriched sequence 180 that is mutated in relation to the reference allele (e.g., cytosine nucleotide base 162) is considered as the alternative allele. Additionally, each enriched sequence 180B amplified from target sequence 170B includes the cytosine nucleotide base located near or at the center of each enriched sequence 180B.

In step 140, sequence reads are generated from the enriched nucleic acid molecules (e.g., DNA molecules). Sequencing data or sequence reads may be acquired from the enriched nucleic acid molecules by known means in the art. For example, the method 100 may include next generation sequencing (NGS) techniques including synthesis technology (ILLUMINA®), pyrosequencing (454 LIFE SCIENCES), ion semiconductor technology (Ion Torrent sequencing), single-molecule real-time sequencing (PACIFIC BIOSCIENCES®), sequencing by ligation (SOLiD sequencing), nanopore sequencing (OXFORD NANOPORE TECHNOLOGIES), or paired-end sequencing. In some embodiments, massively parallel sequencing is performed using sequencing-by-synthesis with reversible dye terminators.

In various embodiments, the enriched nucleic acid sample 115 is provided to the sequencer 145 for sequencing. As shown in FIG. 1A, the sequencer 145 can include a graphical user interface 150 that enables user interactions with particular tasks (e.g., initiate sequencing or terminate sequencing) as well as one more loading trays 155 for providing the enriched fragment samples and/or necessary buffers for performing the sequencing assays. Therefore, once a user has provided the necessary reagents and enriched fragment samples to the loading trays 155 of the sequencer 145, the user can initiate sequencing by interacting with the graphical user interface 150 of the sequencer 145. In step 140, the sequencer 145 performs the sequencing and outputs the sequence reads of the enriched fragments from the nucleic acid sample 115.

In some embodiments, the sequencer 145 is communicatively coupled with one or more computing devices 160. Each computing device 160 can process the sequence reads for various applications such as variant calling or quality control. The sequencer 145 may provide the sequence reads in a BAM file format to a computing device 160. Each computing device 160 can be one of a personal computer (PC), a desktop computer, a laptop computer, a notebook, a tablet PC, or a mobile device. A computing device 160 can be communicatively coupled to the sequencer 145 through a wireless, wired, or a combination of wireless and wired communication technologies. Generally, the computing device 160 is configured with a processor and memory storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information. For example, in one embodiment, sequence reads are aligned to human reference genome hg19. The sequence of the human reference genome, hg19, is available from Genome Reference Consortium with a reference number, GRCh37/hg19, and also available from Genome Browser provided by Santa Cruz Genomics Institute. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, for example when a paired-end sequencing process is used, a sequence read is comprised of a read pair denoted as $R_1$ and $R_2$. For example, the first read $R_1$ may be sequenced from a first end of a double-stranded DNA (dsDNA) molecule whereas the second read $R_2$ may be sequenced from the second end of the double-stranded DNA (dsDNA). Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis such as variant calling, as described below with respect to FIG. 2.

III. Example Processing System

Figure 2:
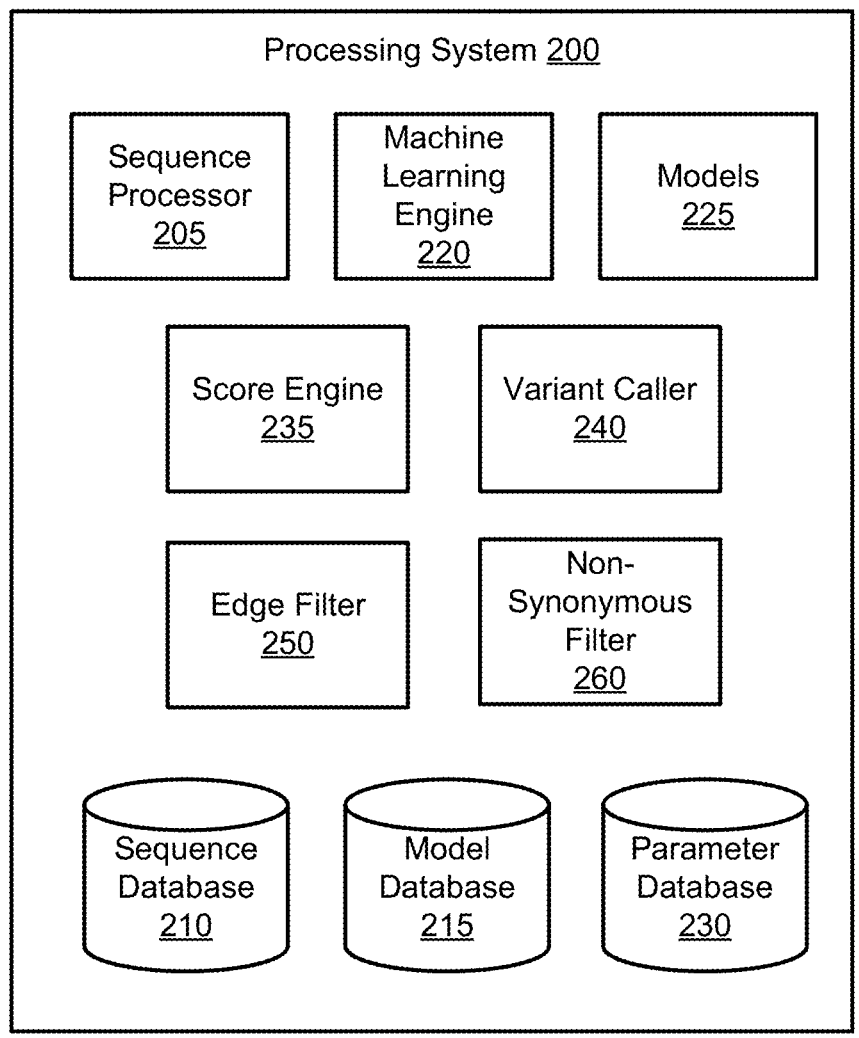
FIG. 2 is block diagram of a processing system for processing sequence reads according to one embodiment.
Figure 3:
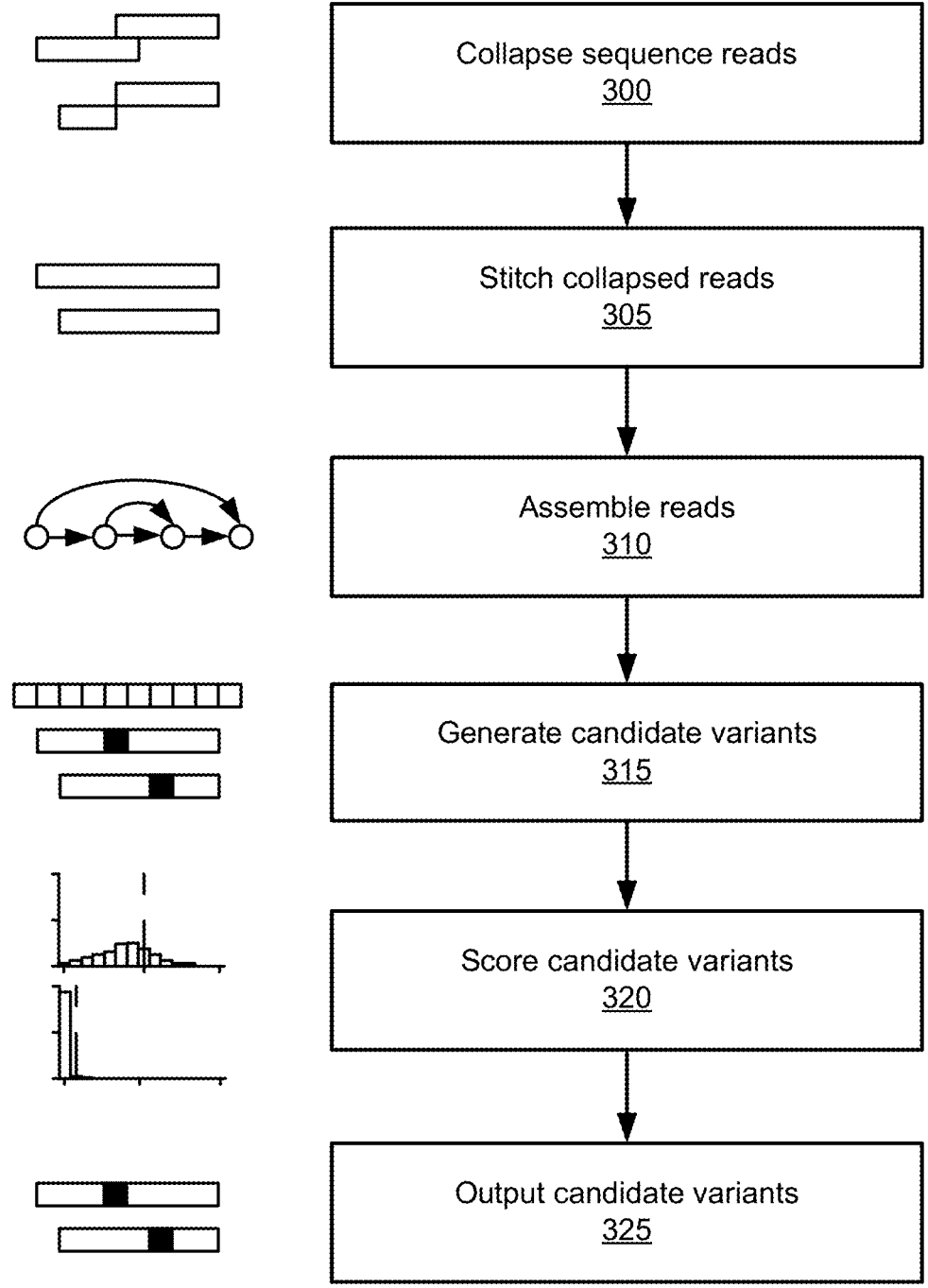
FIG. 3 is flowchart of a method for determining variants of sequence reads according to one embodiment.

FIG. 2 is block diagram of a processing system 200 for processing sequence reads according to one embodiment. The processing system 200 includes a sequence processor 205, sequence database 210, model database 215, machine learning engine 220, models 225 (for example, including a "Bayesian hierarchical model" or a "predictive cancer model"), parameter database 230, score engine 235, variant caller 240, edge filter 250, and non-synonymous filter 260. FIG. 3 is flowchart of a method 300 for determining variants of sequence reads according to one embodiment. In some embodiments, the processing system 200 performs the method 300 to perform variant calling (e.g., for SNVs and/or indels) based on input sequencing data. Further, the processing system 200 may obtain the input sequencing data from an output file associated with nucleic acid sample prepared using the method 100 described above. The method 300 includes, but is not limited to, the following steps, which are described with respect to the components of the processing system 200. In other embodiments, one or more steps of the method 300 may be replaced by a step of a different process for generating variant calls, e.g., using Variant Call Format (VCF), such as HaplotypeCaller, VarScan, Strelka, or SomaticSniper.

At step 300, optionally, the sequence processor 205 collapses aligned sequence reads of the input sequencing data. In one embodiment, collapsing sequence reads includes using UMIs, and optionally alignment position information from sequencing data of an output file (e.g., from the method 100 shown in FIG. 1A) to identify and collapse multiple sequence reads (i.e., derived from the same original nucleic acid molecule) into a consensus sequence. In accordance with this step, a consensus sequence is determined from multiple sequence reads derived from the same original nucleic acid molecule that represents the most likely nucleic acid sequence, or portion thereof, of the original molecule. Since the UMI sequences are replicated through PCR amplification of the sequencing library, the sequence processor 205 can determine that certain sequence reads originated from the same molecule in a nucleic acid sample. In some embodiments, sequence reads that have the same or similar alignment position information (e.g., beginning and end positions within a threshold offset) and include a common UMI are collapsed, and the sequence processor 205 generates a collapsed read (also referred to herein as a consensus read) to represent the nucleic acid fragment. In some embodiments, the sequence processor 205 designates a consensus read as "duplex" if the corresponding pair of sequence reads (i.e., $R_1$ and $R_2$), or collapsed sequence reads, have a common UMI, which indicates that both positive and negative strands of the originating nucleic acid molecule have been captured; otherwise, the collapsed read is designated "non-duplex." In some embodiments, the sequence processor 205 may perform other types of error correction on sequence reads as an alternative to, or in addition to, collapsing sequence reads.

At step 305, optionally, the sequence processor 205 may stitch sequence reads, or collapsed sequence reads, based on the corresponding alignment position information merging together two sequence reads into a single read segment. In some embodiments, the sequence processor 205 compares alignment position information between a first sequence read and a second sequence read (or collapsed sequence reads) to determine whether nucleotide base pairs of the first and second reads partially overlap in the reference genome. In one use case, responsive to determining that an overlap (e.g., of a given number of nucleotide bases) between the first and second reads is greater than a threshold length (e.g., threshold number of nucleotide bases), the sequence processor 205 designates the first and second reads as "stitched"; otherwise, the collapsed reads are designated "unstitched." In some embodiments, a first and second read are stitched if the overlap is greater than the threshold length and if the overlap is not a sliding overlap. For example, a sliding overlap may include a homopolymer run (e.g., a single repeating nucleotide base), a dinucleotide run (e.g., two-nucleotide repeating base sequence), or a trinucleotide run (e.g., three-nucleotide repeating base sequence), where the homopolymer run, dinucleotide run, or trinucleotide run has at least a threshold length of base pairs.

At step 310, the sequence processor 205 may optionally assemble two or more reads, or read segments, into a merged sequence read (or a path covering the targeted region). In some embodiments, the sequence processor 205 assembles reads to generate a directed graph, for example, a de Bruijn graph, for a target region (e.g., a gene). Unidirectional edges of the directed graph represent sequences of k nucleotide bases (also referred to herein as "k-mers") in the target region, and the edges are connected by vertices (or nodes). The sequence processor 205 aligns collapsed reads to a directed graph such that any of the collapsed reads may be represented in order by a subset of the edges and corresponding vertices.

In some embodiments, the sequence processor 205 determines sets of parameters describing directed graphs and processes directed graphs. Additionally, the set of parameters may include a count of successfully aligned k-mers from collapsed reads to a k-mer represented by a node or edge in the directed graph. The sequence processor 205 stores, e.g., in the sequence database 210, directed graphs and corresponding sets of parameters, which may be retrieved to update graphs or generate new graphs. For instance, the sequence processor 205 may generate a compressed version of a directed graph (e.g., or modify an existing graph) based on the set of parameters. In one use case, in order to filter out data of a directed graph having lower levels of importance, the sequence processor 205 removes (e.g., "trims" or "prunes") nodes or edges having a count less than a threshold value, and maintains nodes or edges having counts greater than or equal to the threshold value.

At step 315, the variant caller 240 generates candidate variants from the sequence reads, collapsed sequence reads, or merged sequence reads assembled by the sequence processor 205. In one embodiment, the variant caller 240 generates the candidate variants by comparing sequence reads, collapsed sequence reads, or merged sequence reads (which may have been compressed by pruning edges or nodes in step 310) to a reference sequence of a target region of a reference genome (e.g., human reference genome hg19). The variant caller 240 may align edges of the sequence reads collapsed sequence reads, or merged sequence reads to the reference sequence, and records the genomic positions of mismatched edges and mismatched nucleotide bases adjacent to the edges as the locations of candidate variants. In some embodiments, the genomic positions of mismatched nucleotide bases to the left and right edges are recorded as the locations of called variants. Additionally, the variant caller 240 may generate candidate variants based on the sequencing depth of a target region. In particular, the variant caller 240 may be more confident in identifying variants in target regions that have greater sequencing depth, for example, because a greater number of sequence reads help to resolve (e.g., using redundancies) mismatches or other base pair variations between sequences.

In one embodiment, the variant caller 240 generates candidate variants using the model 225 to determine expected noise rates for sequence reads from a subject (e.g., from a healthy subject). The model 225 may be a Bayesian hierarchical model, though in some embodiments, the processing system 200 uses one or more different types of models. Moreover, a Bayesian hierarchical model may be one of many possible model architectures that may be used to generate candidate variants and which are related to each other in that they all model position-specific noise information in order to improve the sensitivity or specificity of variant calling. More specifically, the machine learning engine 220 trains the model 225 using samples from healthy individuals to model the expected noise rates per position of sequence reads.

Further, multiple different models may be stored in the model database 215 or retrieved for application post-training. For example, a first model is trained to model SNV noise rates and a second model is trained to model indel noise rates. Further, the score engine 235 may use parameters of the model 225 to determine a likelihood of one or more true positives in a sequence read. The score engine 235 may determine a quality score (e.g., on a logarithmic scale) based on the likelihood. For example, the quality score is a Phred quality score $Q=-10\cdot\log_{10} P$, where P is the likelihood of an incorrect candidate variant call (e.g., a false positive).

At step 320, the score engine 235 scores the candidate variants based on the model 225 or corresponding likelihoods of true positives or quality scores. Training and application of the model 225 is described in more detail below. In some embodiments, the processing system 200 may filter the candidate variants using on one or more criteria. For example, processing system 200 filter candidate variants having at least (or less than) a threshold score.

At step 325, the processing system 200 outputs the candidate variants. In some embodiments, the processing system 200 outputs some or all of the determined candidate variants along with the corresponding scores. Downstream systems, e.g., external to the processing system 200 or other components of the processing system 200, may use the candidate variants and scores for various applications including, but not limited to, predicting presence of cancer, disease, or germline mutations.

FIGS. 1-3 exemplify possible embodiments for generating sequencing read data and identifying candidate variants or rare mutation calls. However, as one of skill in the art would readily appreciate, other known means in the art for obtaining sequencing data, such as sequence reads or consensus sequence reads, and identifying candidate variants or rare mutation calls therefrom, can be used in the practice of embodiments of the present invention (see, e.g., U.S. Patent Publication No. 2012/0065081, U.S. Patent Publication No. 2014/0227705, U.S. Patent Publication No. 2015/0044687 and U.S. Patent Publication No. 2017/0058332).

IV. Example Noise Models

Figure 4:
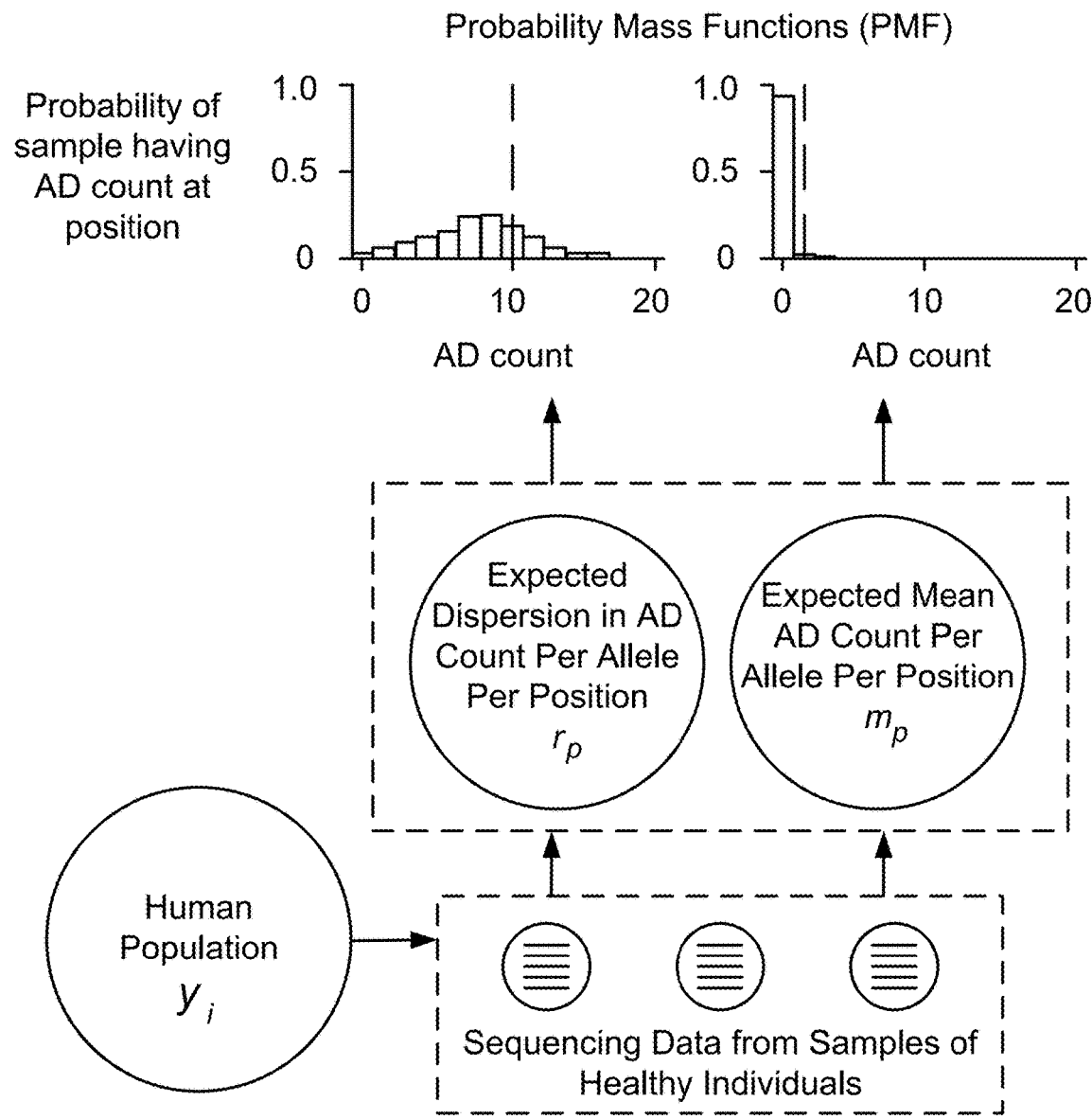
FIG. 4 is a diagram of an application of a Bayesian hierarchical model according to one embodiment.

FIG. 4 is a diagram of an application of a Bayesian hierarchical model 225 according to one embodiment. Mutation A and Mutation B are shown as examples for purposes of explanation. In the embodiment of FIG. 4, Mutations A and B are represented as SNVs, though in other embodiments, the following description is also applicable to indels or other types of mutations. Mutation A is a C>T mutation at position 4 of a first reference allele from a first sample. The first sample has a first AD of 10 and a first total depth of 1000. Mutation B is a T>G mutation at position 3 of a second reference allele from a second sample. The second sample has a second AD of 1 and a second total depth of 1200. Based merely on AD (or AF), Mutation A may appear to be a true positive, while Mutation B may appear to be a false positive because the AD (or AF) of the former is greater than that of the latter. However, Mutations A and B may have different relative levels of noise rates per allele and/or per position of the allele. In fact, Mutation A may be a false positive and Mutation B may be a true positive, once the relative noise levels of these different positions are accounted for. The models 225 described herein model this noise for appropriate identification of true positives accordingly.

The probability mass functions (PMFs) illustrated in FIG. 4 indicate the probability (or likelihood) of a sample from a subject having a given AD count at a position. Using sequencing data from samples of healthy individuals (e.g., stored in the sequence database 210), the processing system 200 trains a model 225 from which the PMFs for healthy samples may be derived. In particular, the PMFs are based on $m_p$, which models the expected mean AD count per allele per position in normal tissue (e.g., of a healthy individual), and $r_p$, which models the expected variation (e.g., dispersion) in this AD count. Stated differently, $m_p$ and/or $r_p$ represent a baseline level of noise, on a per position per allele basis, in the sequencing data for normal tissue.

Using the example of FIG. 4 to further illustrate, samples from the healthy individuals represent a subset of the human population modeled by $y_i$, where i is the index of the healthy individual in the training set. Assuming for sake of example the model 225 has already been trained, PMFs produced by the model 225 visually illustrate the likelihood of the measured ADs for each mutation, and therefore provide an indication of which are true positives and which are false positives. The example PMF on the left of FIG. 4 associated with Mutation A indicates that the probability of the first sample having an AD count of 10 for the mutation at position 4 is approximately 20%. Additionally, the example PMF on the right associated with Mutation B indicates that the probability of the second sample having an AD count of 1 for the mutation at position 3 is approximately 1% (note: the PMFs of FIG. 4 are not exactly to scale). Thus, the noise rates corresponding to these probabilities of the PMFs indicate that Mutation A is more likely to occur than Mutation B, despite Mutation B having a lower AD and AF. Thus, in this example, Mutation B may be the true positive and Mutation A may be the false positive. Accordingly, the processing system 200 may perform improved variant calling by using the model 225 to distinguish true positives from false positives at a more accurate rate, and further provide numerical confidence as to these likelihoods.

Figure 5A:
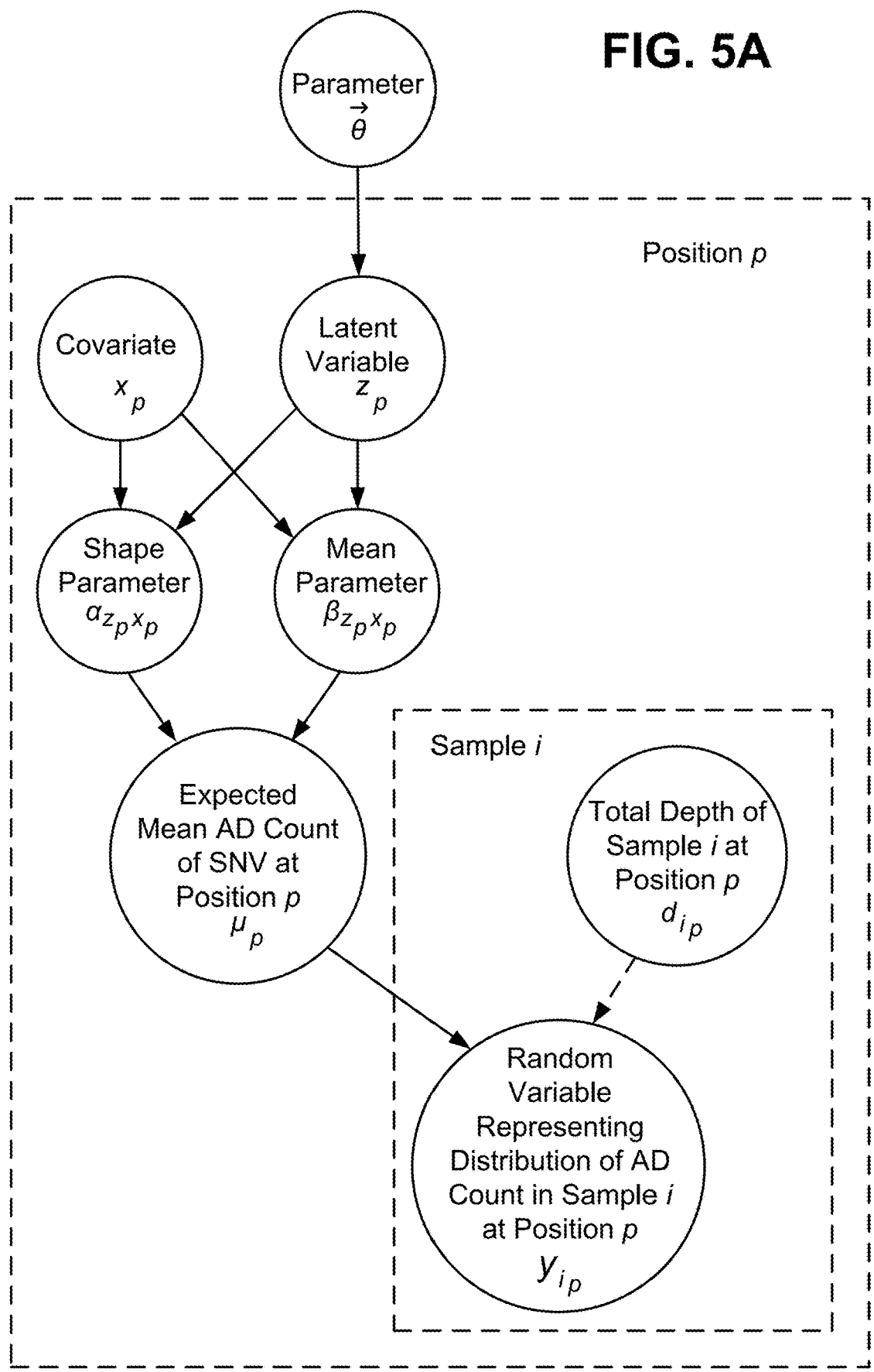
FIG. 5A shows dependencies between parameters and sub-models of a Bayesian hierarchical model for determining true single nucleotide variants according to one embodiment.

FIG. 5A shows dependencies between parameters and sub-models of a Bayesian hierarchical model 225 for determining true single nucleotide variants according to one embodiment. Parameters of models may be stored in the parameter database 230. In the example shown in FIG. 5A, $\vec{\theta}$ represents the vector of weights assigned to each mixture component. The vector $\vec{\theta}$ takes on values within the simplex in K dimensions and may be learned or updated via posterior sampling during training. It may be given a uniform prior on said simplex for such training. The mixture component to which a position p belongs may be modeled by latent variable $z_p$ using one or more different multinomial distributions:

$$z_p \sim \text{Multinom}(\vec{\theta})$$

Together, the latent variable $z_p$, the vector of mixture components $\vec{\theta}$, $\alpha$, and $\beta$ allow the model for $\mu$, that is, a sub-model of the Bayesian hierarchical model 225, to have parameters that "pool" knowledge about noise, that is they represent similarity in noise characteristics across multiple positions. Thus, positions of sequence reads may be pooled or grouped into latent classes by the model. Also advantageously, samples of any of these "pooled" positions can help train these shared parameters. A benefit of this is that the processing system 200 may determine a model of noise in healthy samples even if there is little to no direct evidence of alternate alleles having been observed for a given position previously (e.g., in the healthy tissue samples used to train the model).

The covariate $x_p$ (e.g., a predictor) encodes known contextual information regarding position p which may include, but is not limited to, information such as trinucleotide context, mappability, segmental duplication, distance closest to repeat, uniqueness, k-mer uniqueness, warnings for badly behaved regions of a sequence, or other information associated with sequence reads. Trinucleotide context may be based on a reference allele and may be assigned numerical (e.g., integer) representation. For instance, "AAA" is assigned 1, "ACA" is assigned 2, "AGA" is assigned 3, etc. Mappability represents a level of uniqueness of alignment of a read to a particular target region of a genome. For example, mappability is calculated as the inverse of the number of position(s) where the sequence read will uniquely map. Segmental duplications correspond to long nucleic acid sequences (e.g., having a length greater than approximately 1000 base pairs) that are nearly identical (e.g., greater than 90% match) and occur in multiple locations in a genome as result of natural duplication events (e.g., not associated with a cancer or disease).

The expected mean AD count of a SNV at position p is modeled by the parameter $\mu_p$. For sake of clarity in this description, the terms $\mu_p$ and $y_p$ refer to the position specific sub-models of the Bayesian hierarchical model 225. In one embodiment, $\mu_p$ is modeled as a Gamma-distributed random variable having shape parameter $\alpha_{z_p,x_p}$ and mean parameter $\beta_{z_p,x_p}$:

$$\mu_p \sim \text{Gamma}(\alpha_{z_p,x_p}, \beta_{z_p,x_p})$$

In other embodiments, other functions may be used to represent $\mu_p$, examples of which include but are not limited to: a log-normal distribution with log-mean $\gamma_{z_p}$ and log-standard-deviation $\sigma_{z_p,x_p}$, a Weibull distribution, a power law, an exponentially-modulated power law, or a mixture of the preceding.

In the example shown in FIG. 5A, the shape and mean parameters are each dependent on the covariate $x_p$ and the latent variable $z_p$, though in other embodiments, the dependencies may be different based on various degrees of information pooling during training. For instance, the model may alternately be structured so that $\alpha_{z_p}$ depends on the latent variable but not the covariate. The distribution of AD count of the SNV at position p in a human population sample i (of a healthy individual) is modeled by the random variable $y_{i_p}$. In one embodiment, the distribution is a Poisson distribution given a depth $d_{i_p}$ of the sample at the position:

$$y_{i_p} | d_{i_p} \sim \text{Poisson}(d_{i_p} \cdot \mu_p)$$

In other embodiments, other functions may be used to represent $y_{i_p}$, examples of which include but are not limited to: negative binomial, Conway-Maxwell-Poisson distribution, zeta distribution, and zero-inflated Poisson.

Figure 5B:
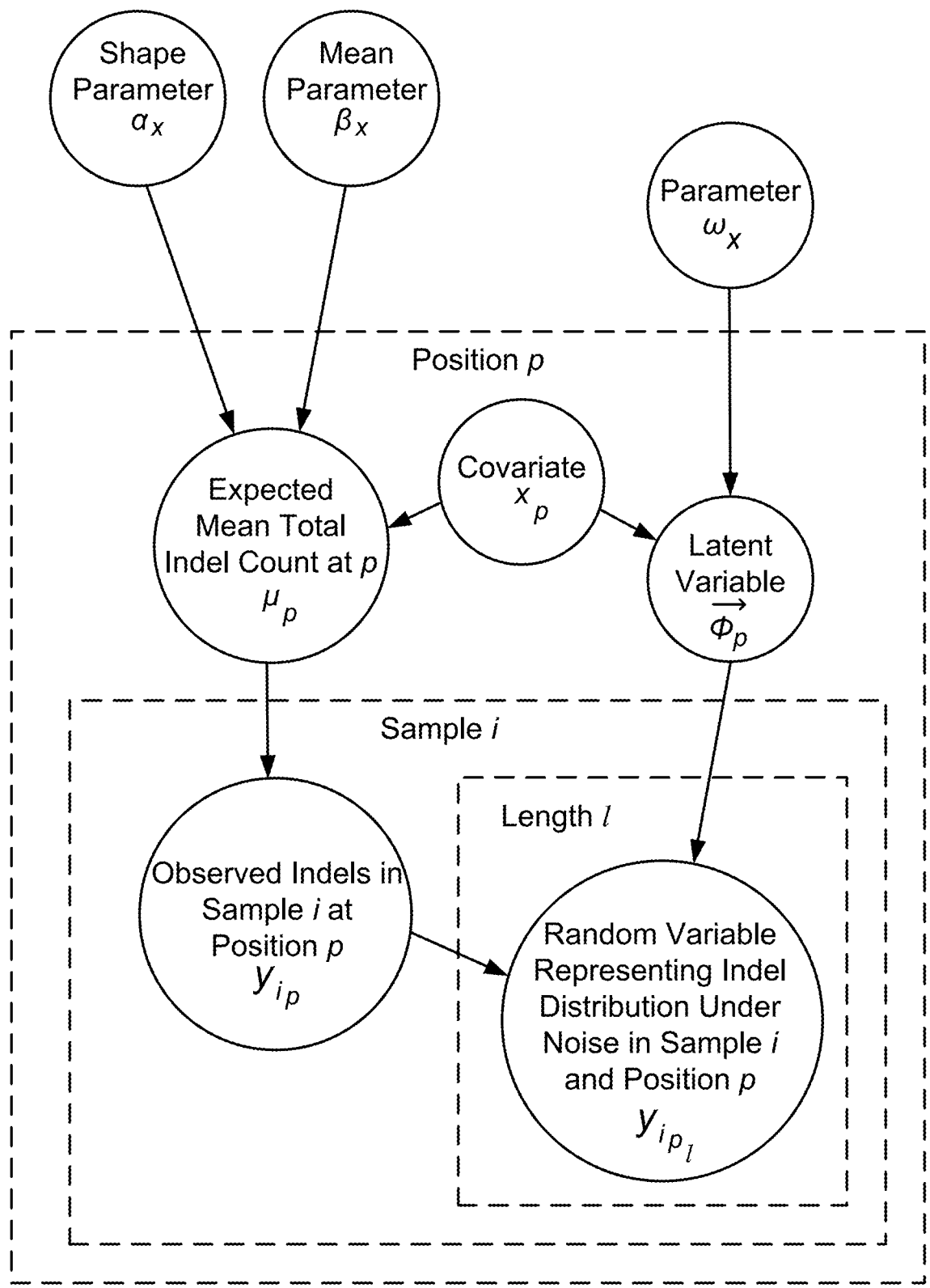
FIG. 5B shows dependencies between parameters and sub-models of a Bayesian hierarchical model for determining true insertions or deletions according to one embodiment.

FIG. 5B shows dependencies between parameters and sub-models of a Bayesian hierarchical model for determining true insertions or deletions according to one embodiment. In contrast to the SNV model shown in FIG. 5A, the model for indels shown in FIG. 5B includes different levels of hierarchy. The covariate $x_p$ encodes known features at position p and may include, e.g., a distance to a homopolymer, distance to a RepeatMasker repeat, or other information associated with previously observed sequence reads.

Latent variable $\vec{\phi}_p$ may be modeled by a Dirichlet distribution based on parameters of vector $\vec{\Omega}_x$, which represent indel length distributions at a position and may be based on the covariate. In some embodiments, $\vec{\Omega}_x$ is also shared across positions ($\vec{\Omega}_{x,p}$) that share the same covariate value(s). Thus for example, the latent variable may represent information such that homopolymer indels occur at positions 1, 2, 3, etc. base pairs from the anchor position, while trinucleotide indels occur at positions 3, 6, 9, etc. from the anchor position.

The expected mean total indel count at position p is modeled by the distribution $\mu_p$. In some embodiments, the distribution is based on the covariate and has a Gamma distribution having shape parameter $\alpha_{x_p}$ and mean parameter $\beta_{x_p,z_p}$:

$$\mu_p \sim \text{Gamma}(\alpha_{x_p}, \beta_{x_p,z_p})$$

In other embodiments, other functions may be used to represent $\mu_p$, examples of which include but are not limited to: negative binomial, Conway-Maxwell-Poisson distribution, zeta distribution, and zero-inflated Poisson.

The observed indels at position p in a human population sample i (of a healthy individual) is modeled by the distribution $y_{i_p}$. Similar to example in FIG. 5A, in some embodiments, the distribution of indel intensity is a Poisson distribution given a depth $d_{i_p}$ of the sample at the position:

$$y_{i_p} | d_{i_p} \sim \text{Poisson}(d_{i_p} \cdot \mu_p)$$

In other embodiments, other functions may be used to represent $y_{i_p}$, examples of which include but are not limited to: negative binomial, Conway-Maxwell-Poisson distribution, zeta distribution, and zero-inflated Poisson.

Due to the fact that indels may be of varying lengths, an additional length parameter is present in the indel model that is not present in the model for SNVs. As a consequence, the example model shown in FIG. 5B has an additional hierarchical level (e.g., another sub-model), which is again not present in the SNV models discussed above. The observed count of indels of length l (e.g., up to 100 or more base pairs of insertion or deletion) at position p in sample i is modeled by the random variable $y_{i_{pl}}$, which represents the indel distribution under noise conditional on parameters. The distribution may be a multinomial given indel intensity $y_{i_p}$ of the sample and the distribution of indel lengths $\vec{\phi}_p$ at the position:

$$\vec{y}_{i_{pl}} | y_{i_p}, \vec{\phi}_p \sim \text{Multinom}(y_{i_p}, \vec{\phi}_p)$$

In other embodiments, a Dirichlet-Multinomial function or other types of models may be used to represent $y_{i_{p_l}}$.

By architecting the model in this manner, the machine learning engine 220 may decouple learning of indel intensity (i.e., noise rate) from learning of indel length distribution. Independently determining inferences for an expectation for whether an indel will occur in healthy samples and expectation for the length of the indel at a position may improve the sensitivity of the model. For example, the length distribution may be more stable relative to the indel intensity at a number of positions or regions in the genome, or vice versa.

Figure 6A:
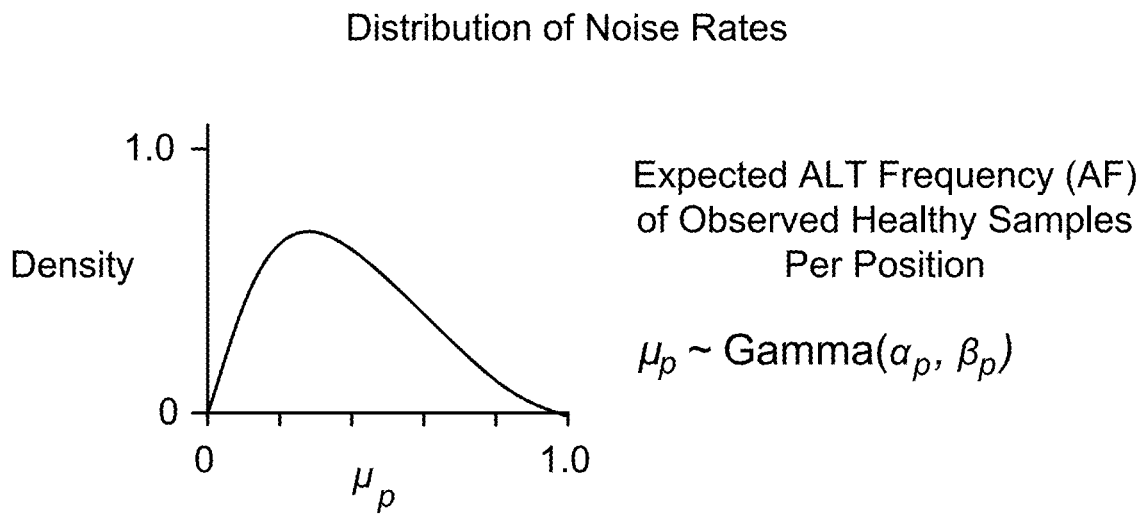
FIGS. 6A-B illustrate diagrams associated with a Bayesian hierarchical model according to one embodiment.
Figure 6B:
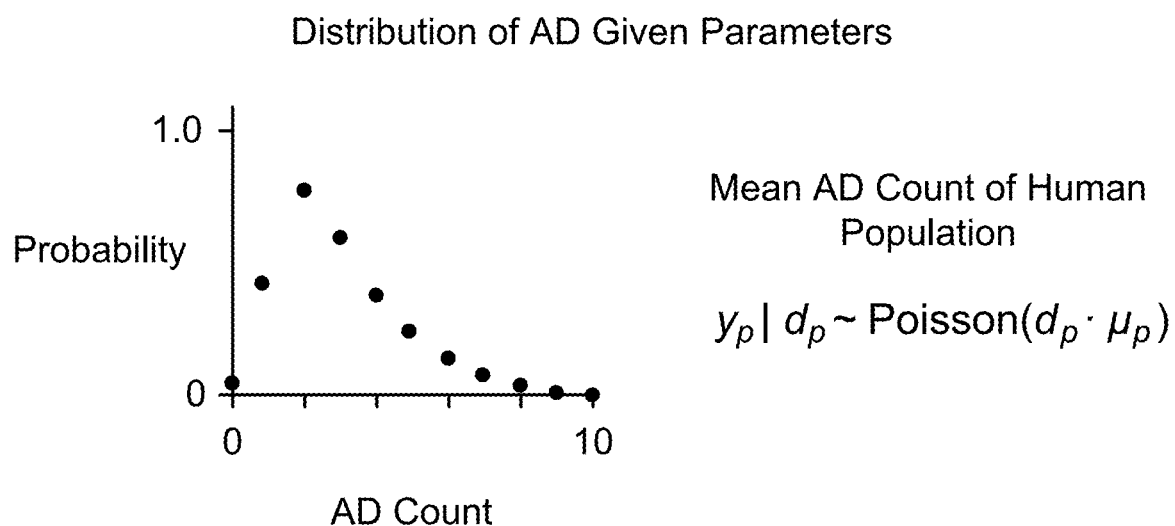

FIGS. 6A-B illustrate diagrams associated with a Bayesian hierarchical model 225 according to one embodiment. The graph shown in FIG. 6A depicts the distribution $\mu_p$ of noise rates, i.e., likelihood (or intensity) of SNVs or indels for a given position as characterized by a model. The continuous distribution represents the expected AF $\mu_p$ of non-cancer or non-disease mutations (e.g., mutations naturally occurring in healthy tissue) based on training data of observed healthy samples from healthy individuals (e.g., retrieved from the sequence database 210). Though not shown in FIG. 6A, in some embodiments, the shape and mean parameters of $\mu_p$ may be based on other variables such as the covariate $x_p$ or latent variable $z_p$. The graph shown in FIG. 6B depicts the distribution of AD at a given position for a sample of a subject, given parameters of the sample such as sequencing depth $d_p$ at the given position. The discrete probabilities for a draw of $\mu_p$ are determined based on the predicted true mean AD count of the human population based on the expected mean distribution $\mu_p$.

Figure 7A:
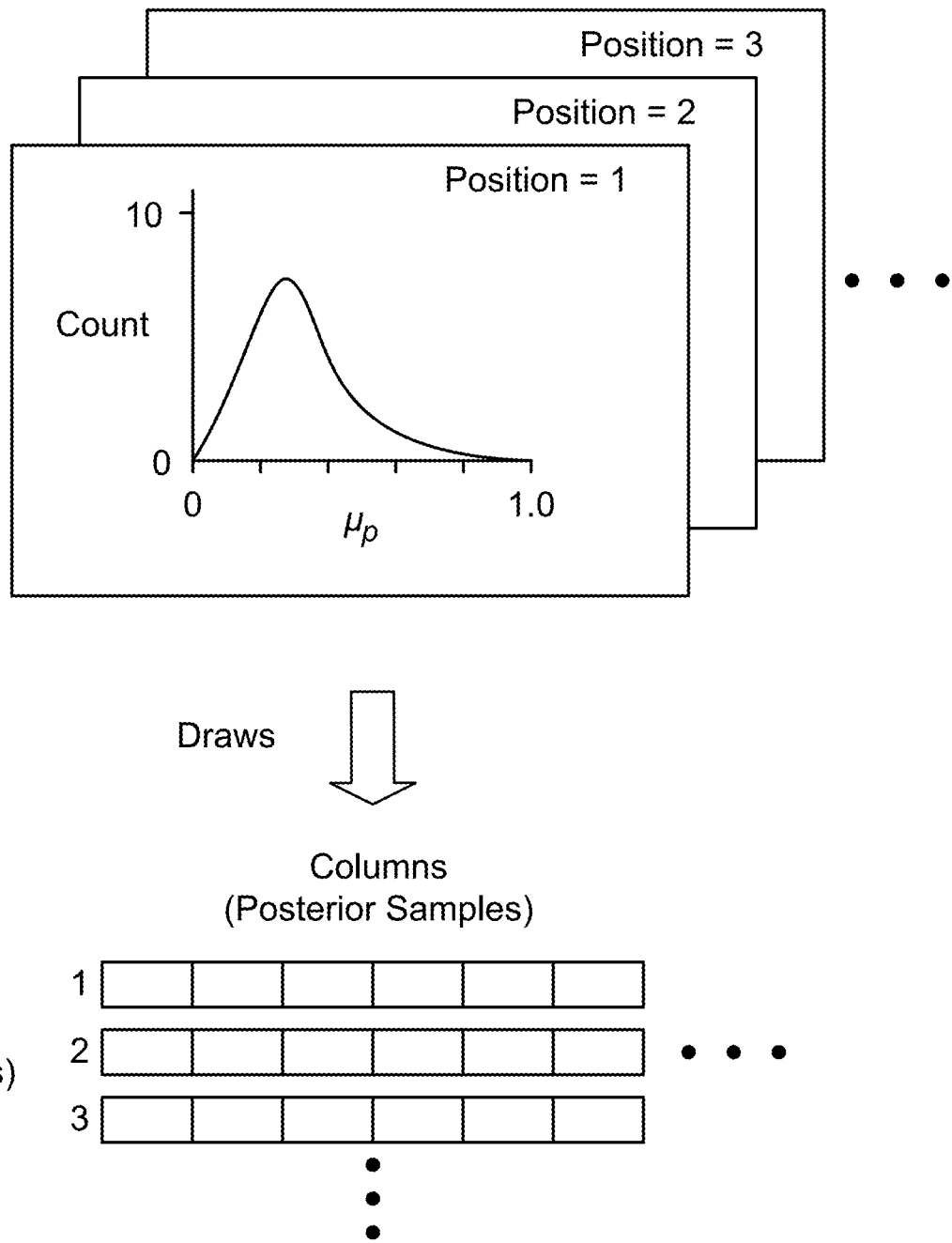
FIG. 7A is a diagram of determining parameters by fitting a Bayesian hierarchical model according to one embodiment.

FIG. 7A is a diagram of an example process for determining parameters by fitting a Bayesian hierarchical model 225 according to one embodiment. To train a model, the machine learning engine 220 samples iteratively from a posterior distribution of expected noise rates (e.g., the graph shown in FIG. 6B) for each position of a set of positions. The machine learning engine 220 may use Markov chain Monte Carlo (MCMC) methods for sampling, e.g., a Metropolis-Hastings (MH) algorithm, custom MH algorithms, Gibbs sampling algorithm, Hamiltonian mechanics-based sampling, random sampling, among other sampling algorithms. During Bayesian Inference training, parameters are drawn from the joint posterior distribution to iteratively update all (or some) parameters and latent variables of the model (e.g., $\vec{\theta}$, $z_p$, $\alpha_{z_p,x_p}$, $\beta_{z_p,x_p}$, $\mu_p$, etc.).

In one embodiment, the machine learning engine 220 performs model fitting by storing draws of $\mu_p$, the expected mean counts of AF per position and per sample, in the parameters database 230. The model is trained or fitted through posterior sampling, as previously described. In an embodiment, the draws of $\mu_p$ are stored in a matrix data structure having a row per position of the set of positions sampled and a column per draw from the joint posterior (e.g., of all parameters conditional on the observed data). The number of rows R may be greater than 6 million and the number of columns for N iterations of samples may be in the thousands. In other embodiments, the row and column designations are different than the embodiment shown in FIG. 7A, e.g., each row represents a draw from a posterior sample, and each column represents a sampled position (e.g., transpose of the matrix example shown in FIG. 7A).

Figure 7B:
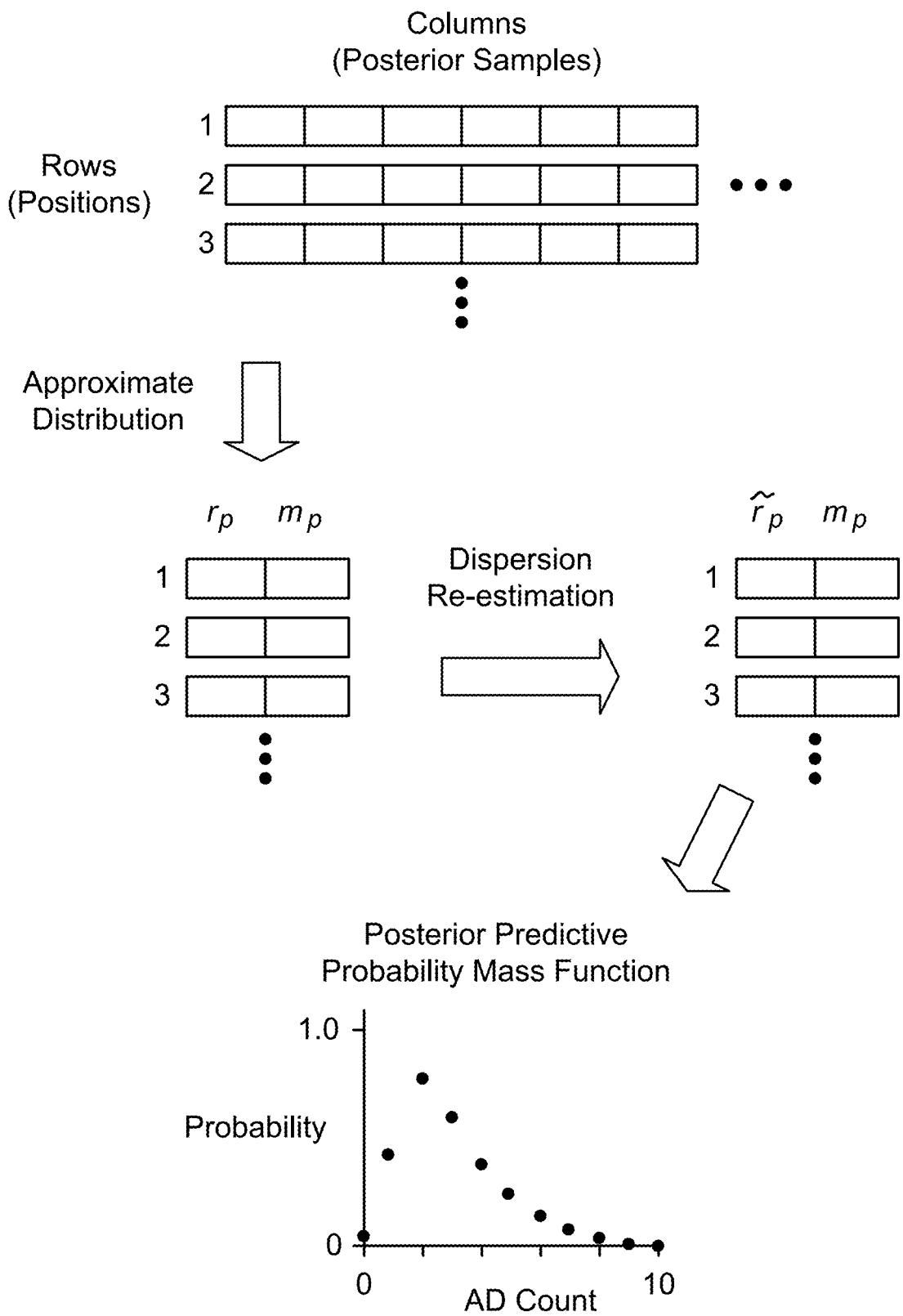
FIG. 7B is a diagram of using parameters from a Bayesian hierarchical model to determine a likelihood of a false positive according to one embodiment.

FIG. 7B is a diagram of using parameters from a Bayesian hierarchical model 225 to determine a likelihood of a false positive according to one embodiment. The machine learning engine 220 may reduce the R rows-by-N column matrix shown in FIG. 7A into an R rows-by-2 column matrix illustrated in FIG. 7B. In one embodiment, the machine learning engine 220 determines a dispersion parameter $r_p$ (e.g., shape parameter) and mean parameter $m_p$ (which may also be referred to as a mean rate parameter $m_p$) per position across the posterior samples $\mu_p$. The dispersion parameter $r_p$ may be determined as $$r_p = \frac{m_p^2}{v_p^2},$$

where $m_p$ and $v_p$ are the mean and variance of the sampled values of $\mu_p$ at the position, respectively. Those of skill in the art will appreciate that other functions for determining $r_p$ may also be used such as a maximum likelihood estimate.

The machine learning engine 220 may also perform dispersion re-estimation of the dispersion parameters in the reduced matrix, given the mean parameters. In one embodiment, following Bayesian training and posterior approximation, the machine learning engine 220 performs dispersion re-estimation by retraining for the dispersion parameters $\widetilde{r}_p$ based on a negative binomial maximum likelihood estimator per position. The mean parameter may remain fixed during retraining. In one embodiment, the machine learning engine 220 determines the dispersion parameters $r'_p$ at each position for the original AD counts of the training data (e.g., $y_{i_p}$ and $d_{i_p}$ based on healthy samples). The machine learning engine 220 determines $\widetilde{r}_p = \max(r_p, r'_p)$, and stores $\widetilde{r}_p$ in the reduced matrix. Those of skill in the art will appreciate that other functions for determining $\widetilde{r}_p$ may also be used, such as a method of moments estimator, posterior mean, or posterior mode.

During application of trained models, the processing system 200 may access the dispersion (e.g., shape) parameters $\widetilde{r}_p$ and mean parameters $m_p$ to determine a function parameterized by $\widetilde{r}_p$ and $m_p$. The function may be used to determine a posterior predictive probability mass function (or probability density function) for a new sample of a subject. Based on the predicted probability of a certain AD count at a given position, the processing system 200 may account for site-specific noise rates per position of sequence reads when detecting true positives from samples. Referring back to the example use case described with respect to FIG. 4, the PMFs shown for Mutations A and B may be determined using the parameters from the reduced matrix of FIG. 7B. The posterior predictive probability mass functions may be used to determine the probability of samples for Mutations A or B having an AD count at certain position.

V. Example Process Flows for Noise Models

Figure 8:
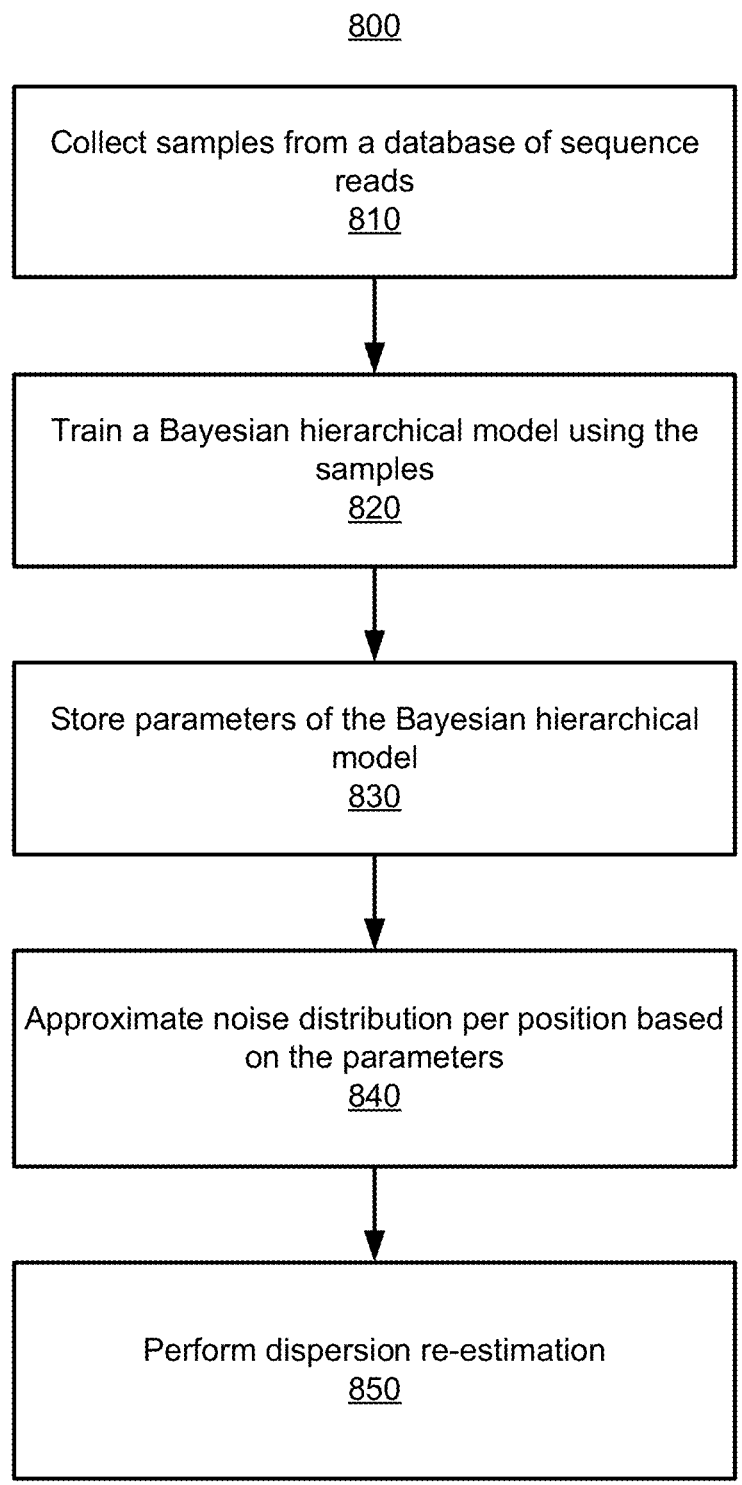
FIG. 8 is flowchart of a method for training a Bayesian hierarchical model according to one embodiment.

FIG. 8 is flowchart of a method 800 for training a Bayesian hierarchical model 225 according to one embodiment. In step 810, the machine learning engine 220 collects samples, e.g., training data, from a database of sequence reads (e.g., the sequence database 210). In step 820, the machine learning engine 220 trains the Bayesian hierarchical model 225 using the samples using a Markov Chain Monte Carlo method. During training, the model 225 may keep or reject sequence reads conditional on the training data. The machine learning engine 220 may exclude sequence reads of healthy individuals that have less than a threshold depth value or that have an AF greater than a threshold frequency in order to remove suspected germline mutations that are not indicative of target noise in sequence reads. In other embodiments, the machine learning engine 220 may determine which positions are likely to contain germline variants and selectively exclude such positions using thresholds like the above. In one embodiment, the machine learning engine 220 may identify such positions as having a small mean absolute deviation of AFs from germline frequencies (e.g., 0, ½, and 1).

The Bayesian hierarchical model 225 may update parameters simultaneously for multiple (or all) positions included in the model. Additionally, the model 225 may be trained to model expected noise for each ALT. For instance, a model for SNVs may perform a training process four or more times to update parameters (e.g., one-to-one substitutions) for mutations of each of the A, T, C, and G bases to each of the other three bases. In step 830, the machine learning engine 220 stores parameters of the Bayesian hierarchical model 225 (e.g., ensemble parameters output by the Markov Chain Monte Carlo method). In step 840, the machine learning engine 220 approximates noise distribution (e.g., represented by a dispersion parameter and a mean parameter) per position based on the parameters. In step 850, the machine learning engine 220 performs dispersion re-estimation (e.g., maximum likelihood estimation) using original AD counts from the samples (e.g., training data) used to train the Bayesian hierarchical model 225.

Figure 9:
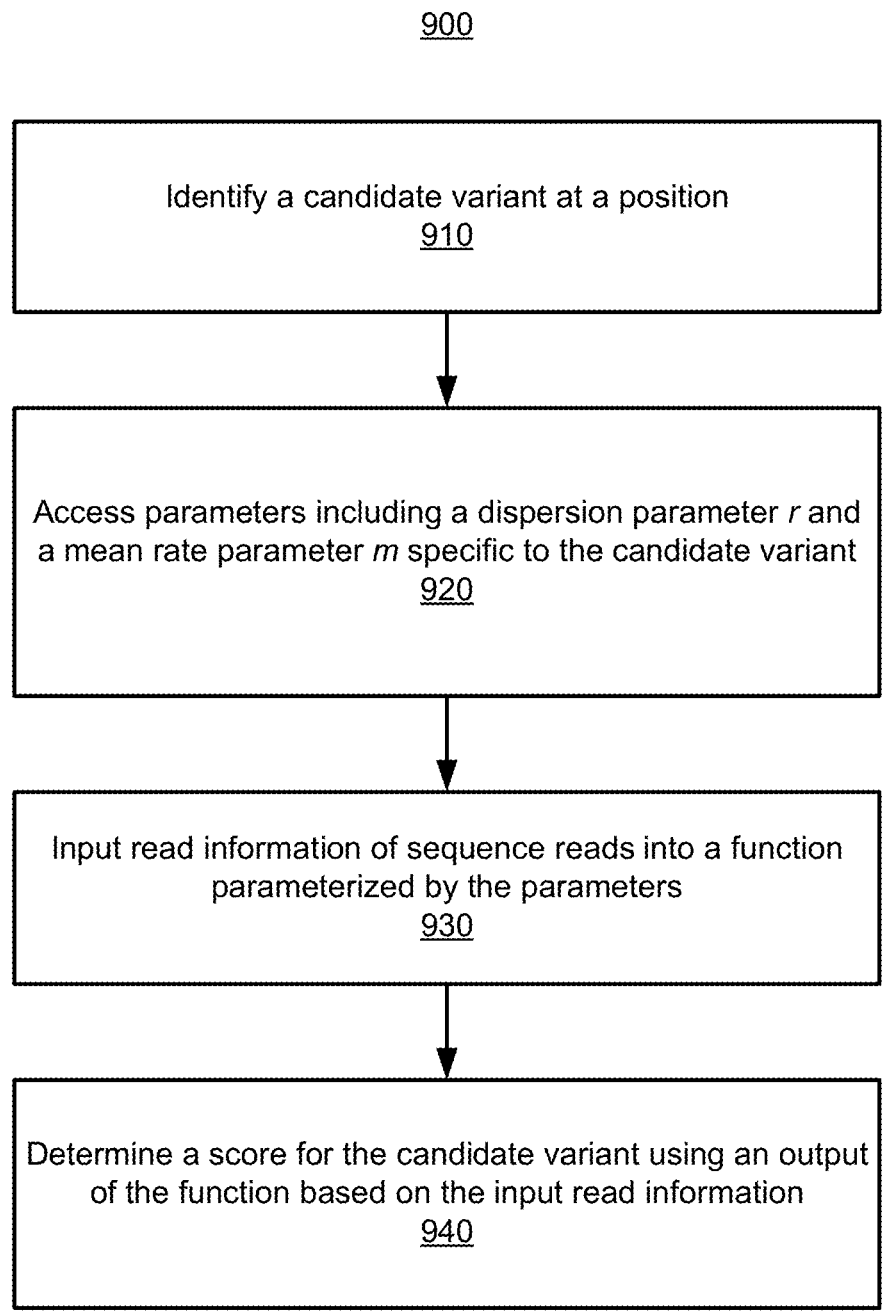
FIG. 9 is flowchart of a method for scoring candidate variants of a given nucleotide mutation according to one embodiment.

FIG. 9 is flowchart of a method 900 for determining a likelihood of a false positive according to one embodiment. At step 910, the processing system 200 identifies a candidate variant, e.g., at a position p of a sequence read, from a set of sequence reads, which may be obtained from a cfDNA sample obtained from an individual. At step 920, the processing system 200 accesses parameters, e.g., dispersion and mean rate parameters $\widetilde{r}_p$ and $m_p$, respectively, specific to the candidate variant, which may be based on the position p of the candidate variant. The parameters may be derived using a model, e.g., a Bayesian hierarchical model 225 representing a posterior predictive distribution with an observed depth of a given sequence read and a mean parameter $\mu_p$ at the position p as input. In an embodiment, the mean parameter $\mu_p$ is a gamma distribution encoding a noise level of nucleotide mutations with respect to the position p for a training sample.

At step 930, the processing system 200 inputs read information (e.g., AD or AF) of the set of sequence reads into a function (e.g., based on a negative binomial) parameterized by the parameters, e.g., $\widetilde{r}_p$ and $m_p$. At step 940, the processing system 200 (e.g., the score engine 235) determines a score for the candidate variant (e.g., at the position p) using an output of the function based on the input read information. The score may indicate a likelihood of seeing an allele count for a given sample (e.g., from a subject) that is greater than or equal to a determined allele count of the candidate variant (e.g., determined by the model and output of the function). The processing system 200 may convert the likelihood into a Phred-scaled score. In some embodiments, the processing system 200 uses the likelihood to determine false positive mutations responsive to determining that the likelihood is less than a threshold value. In some embodiments, the processing system 200 uses the function to determine that a sample of sequence reads includes at least a threshold count of alleles corresponding to a gene found in sequence reads from a tumor biopsy of an individual. Responsive to this determination, the processing system 200 may predict presence of cancer cells in the individual based on variant calls. In some embodiments, the processing system 200 may perform weighting based on quality scores, use the candidate variants and quality scores for false discovery methods, annotate putative calls with quality scores, or provision to subsequent systems.

The processing system 200 may use functions encoding noise levels of nucleotide mutations with respect to a given training sample for downstream analysis. In some embodiments, the processing system 200 uses the aforementioned negative binomial function parameterized by the dispersion and mean rate parameters $\widetilde{r}_p$ and $m_p$ to determine expected noise for a particular nucleic acid position within a sample, e.g., cfDNA or gDNA. Moreover, the processing system 200 may derive the parameters by training a Bayesian hierarchical model 225 using training data associated with the particular nucleic acid sample. The embodiments below describe another type of model referred to herein as a joint model 225, which may use output of a Bayesian hierarchical model 225.

VI. Example Joint Model

Figure 10:
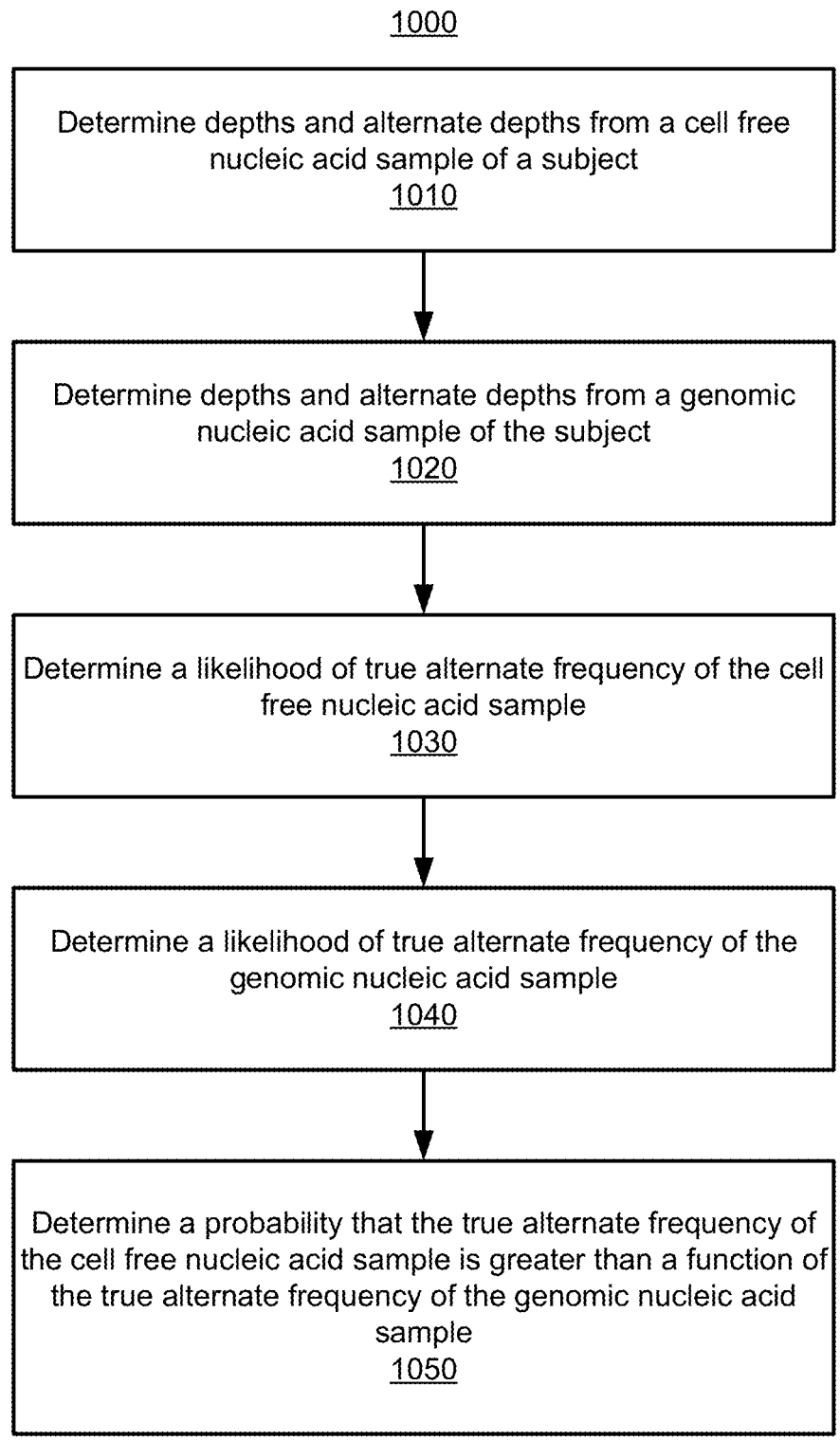
FIG. 10 is flowchart of a method for using a joint model to process cell free nucleic acid samples and genomic nucleic acid samples according to one embodiment.
Figure 11:
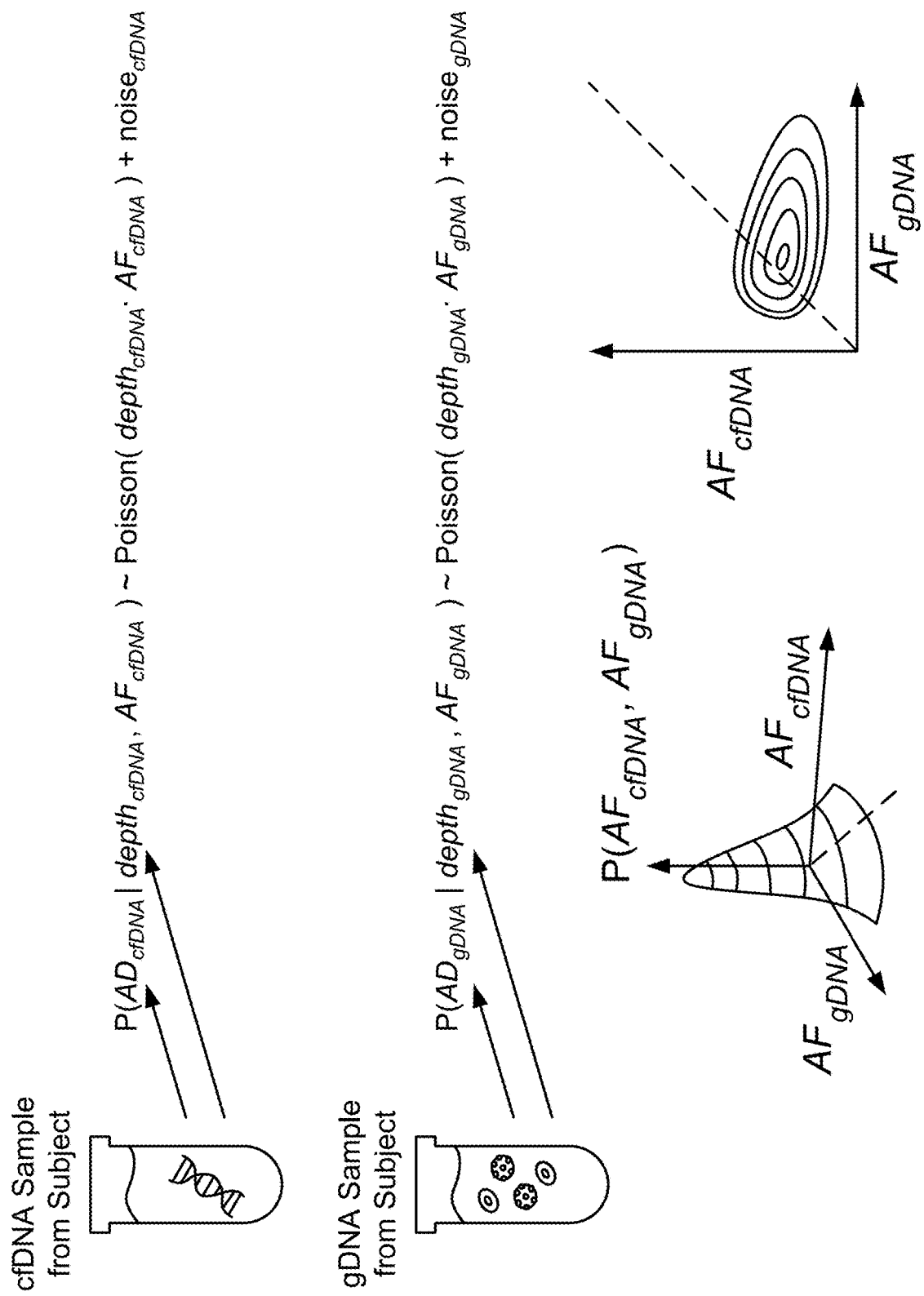
FIG. 11 is a diagram of an application of a joint model according to one embodiment.

FIG. 10 is flowchart of a method 1000 for using a joint model 225 to process cell free nucleic acid (e.g., cfDNA) samples and genomic nucleic acid (e.g., gDNA) samples according to one embodiment. The joint model 225 may be independent of positions of nucleic acids of cfDNA and gDNA. The method 1000 may be performed in conjunction with the methods 800 and/or 900 shown in FIGS. 8-9. For example, the methods 800 and 900 are performed to determine noise of nucleotide mutations with respect to cfDNA and gDNA samples of training data from health samples. FIG. 11 is a diagram of an application of a joint model according to one embodiment. Steps of the method 1000 are described below with reference to FIG. 11.

In step 1010, the sequence processor 205 determines depths and ADs for the various positions of nucleic acids from the sequence reads obtained from a cfDNA sample of a subject. The cfDNA sample may be collected from a sample of blood plasma from the subject. Step 1010 may include previously described steps of the method 100 shown in FIG. 1A.

In step 1020, the sequence processor 205 determines depths and ADs for the various positions of nucleic acids from the sequence reads obtained from a gDNA of the same subject. The gDNA may be collected from white blood cells or a tumor biopsy from the subject. Step 1020 may include previously described steps of the method 100 shown in FIG. 1A.

VI. A. Example Signal of Joint Model

In step 1030, a joint model 225 determines a likelihood of a "true" AF of the cfDNA sample of the subject by modeling the observed ADs for cfDNA. In one embodiment, the joint model 225 uses a Poisson distribution function, parameterized by the depths observed from the sequence reads of cfDNA and the true AF of the cfDNA sample, to model the probability of observing a given AD in cfDNA of the subject (also shown in FIG. 11). The product of the depth and the true AF may be the rate parameter of the Poisson distribution function, which represents the mean expected AF of cfDNA.

$P(AD_{cfDNA}|depth_{cfDNA}, AF_{cfDNA}) \sim$ Poisson $(depth_{cfDNA} \cdot AF_{cfDNA}) + noise_{cfDNA}$ The noise component $noise_{cfDNA}$ is further described below in section VI. B. Example Noise of Joint Model. In other embodiments, other functions may be used to represent $AD_{cfDNA}$, examples of which include but are not limited to: negative binomial, Conway-Maxwell-Poisson distribution, zeta distribution, and zero-inflated Poisson.

In step 1040, the joint model 225 determines a likelihood of a "true" AF of the gDNA sample of the subject by modeling the observed ADs for gDNA. In one embodiment, the joint model 225 uses a Poisson distribution function parameterized by the depths observed from the sequence reads of gDNA and the true AF of the gDNA sample to model the probability of observing a given AD in gDNA of the subject (also shown in FIG. 11). The joint model 225 may use a same function for modeling the likelihoods of true AF of gDNA and cfDNA, though the parameter values differ based on the values observed from the corresponding sample of the subject.

$$P(AD_{gDNA}|\text{depth}_{gDNA}, AF_{gDNA}) \sim \text{Poisson}$$
$$(\text{depth}_{gDNA} \cdot AF_{gDNA}) + \text{noise}_{gDNA}$$

The noise component $\text{noise}_{gDNA}$ is further described below in section VI. B. Example Noise of Joint Model. In other embodiments, other functions may be used to represent $AD_{gDNA}$, examples of which include but are not limited to: negative binomial, Conway-Maxwell-Poisson distribution, zeta distribution, and zero-inflated Poisson.

Since the true AF of cfDNA, as well as the true AF of gDNA, are inherent properties of the biology of a particular subject, it may not necessarily be practical to determine an exact value of the true AF from either source. Moreover, various sources of noise also introduce uncertainty into the estimated values of the true AF. Accordingly, the joint model 225 uses numerical approximation to determine the posterior distributions of true AF conditional on the observed data (e.g., depths and ADs) from a subject and corresponding noise parameters:

$$P(AF_{cfDNA}|\text{depth}_{cfDNA}, AD_{cfDNA}, \widetilde{r_p}_{cfDNA}, m_{p_{cfDNA}})$$

$$P(AF_{gDNA}|\text{depth}_{gDNA}, AD_{gDNA}, \widetilde{r_p}_{gDNA}, m_{p_{gDNA}})$$

The joint model 225 determines the posterior distributions using Bayes' theorem with a prior, for example, a uniform distribution. The priors used for cfDNA and gDNA may be the same (e.g., a uniform distribution ranging from 0 to 1) and independent from each other.

In an embodiment, the joint model 225 determines the posterior distribution of true AF of cfDNA using a likelihood function by varying the parameter, true AF of cfDNA, given a fixed set of observed data from the sample of cfDNA. Additionally, the joint model 225 determines the posterior distribution of true AF of gDNA using another likelihood function by varying the parameter, true AF of gDNA, given a fixed set of observed data from the sample of gDNA. For both cfDNA and gDNA, the joint model 225 numerically approximates the output posterior distribution by fitting a negative binomial (NB):

$$P(AF|\text{depth}, AD) \propto \sum_{i=0}^{AD} \frac{e^{-AF \cdot \text{depth}}(AF \cdot \text{depth})^i}{i!} \cdot NB(AD - i, \text{size} = r, \mu = m \cdot \text{depth})$$

In an embodiment, the joint model 225 performs numerical approximation using the following parameters for the negative binomial, which may provide an improvement in computational speed:

$$P(AF|\text{depth}, AD) \propto NB(AD, \text{size} = \underline{r}, \mu = \underline{m} \cdot \text{depth})$$

Where:

$$\underline{m} = AF + m$$

$$\underline{r} = r \cdot \underline{m}^2 / m_2$$

Since the observed data is different between cfDNA and gDNA, the parameters determined for the negative binomial of cfDNA will vary from those determined for the negative binomial of gDNA.

In step 1050, the variant caller 240 determines, using the likelihoods, a probability that the true AF of the cfDNA sample is greater than a function of the true AF of the gDNA sample. The function may include one or more parameters, for example, empirically-determined k and p values stored in the parameter database 230 and described with additional detail with reference to FIGS. 12-13. The probability represents a confidence level that at least some nucleotide mutations from the sequence reads of cfDNA are not found in sequence reads of reference tissue. The variant caller 240 may provide this information to other processes for downstream analysis. For instance, a high probability indicates that nucleotide mutations from a subject's sequence reads of cfDNA and that are not found in sequence reads of gDNA may have originated from a tumor or other source of cancer within the subject. In contrast, low probability indicates that nucleotide mutations observed in cfDNA likely did not originate from potential cancer cells or other diseased cells of the subject. Instead, the nucleotide mutations may be attributed to naturally occurring mutations in healthy individuals, due to factors such as germline mutations, clonal hematopoiesis (unique mutations that form subpopulations of blood cell DNA), mosaicism, chemotherapy or mutagenic treatments, technical artifacts, among others.

In an embodiment, the variant caller 240 determines that the posterior probability satisfies a chosen criteria based on the one or more parameters (e.g., k and p described below). The distributions of variants are conditionally independent given the sequences of the cfDNA and gDNA. That is, the variant caller 240 presumes that ALTs and noise present in one of the cfDNA or gDNA sample is not influenced by those of the other sample, and vice versa. Thus, the variant caller 240 considers the probabilities of the expected distributions of AD as independent events in determining the probability of observing both a certain true AF of cfDNA and a certain true AF of gDNA, given the observed data and noise parameters from both sources:

$$P(AF_{cfDNA}, AF_{gDNA}|\text{depth}, AD, \widetilde{r_p}, m_p) \propto$$

$$P(AF_{cfDNA}|\text{depth}_{cfDNA}, AD_{cfDNA}, \widetilde{r_p}_{cfDNA}, m_{p_{cfDNA}}) \cdot$$

$$P(AF_{gDNA}|\text{depth}_{gDNA}, AD_{gDNA}, \widetilde{r_p}_{gDNA}, m_{p_{gDNA}})$$

In the example 3D plot in FIG. 11, the probability $P(AF_{cfDNA}, AF_{gDNA})$ is plotted as a 3D contour for pairs of $AF_{cfDNA}$ and $AF_{gDNA}$ values. The example 2D slice of the 3D contour plot along the $AF_{cfDNA}$ and $AF_{gDNA}$ axis illustrates that the volume of the contour plot is skewed toward greater values of $AF_{gDNA}$ relative to the values of $AF_{cfDNA}$. In other embodiments, the contour plot may be skewed differently or have a different form than the example shown in FIG. 11. To numerically approximate the joint likelihood, the sequence processor 205 may calculate the volume defined by the 3D contour of $P(AF_{cfDNA}, AF_{gDNA})$ and a boundary line illustrated by the dotted line shown in the plots of FIG. 11. The sequence processor 205 determines the slope of the boundary line according to the k parameter value, and the boundary line intersects the origin point. The k parameter value may account for a margin of error in the determined true AF. Particularly, the margin of error may cover naturally occurring mutations in healthy individuals such as germline mutations, clonal hematopoiesis, loss of heterozygosity (further described below with reference to FIG. 13), and other sources as described above. Since the 3D contour is split by the boundary line, at least a portion of variants detected from the cfDNA sample may potentially be attributed to variants detected from the gDNA sample, while another portion of the variants may potentially be attributed to a tumor or other source of cancer.

In an embodiment, the sequence processor 205 determines that a given criteria is satisfied by the posterior probability by determining the portion of the joint likelihood that satisfies the given criteria. The given criteria may be based on the k and p parameter, where p represents a threshold probability for comparison. For example, the sequence processor 205 determines the posterior probability that true AF of cfDNA is greater than or equal to the true AF of gDNA multiplied by k, and whether the posterior probability is greater than p:

$$P(AF_{cfDNA} \geq k \cdot AF_{gDNA}) > p, \text{ where}$$

$$P(AF_{cfDNA} \geq k \cdot AF_{gDNA}) =$$

$$\int_0^1 \int_{k \cdot AF_{gDNA}}^1 f_{cfDNA}(AF_{cfDNA}) \cdot f_{gDNA}(AF_{gDNA}) dAF_{cfDNA} dAF_{gDNA} =$$

$$\int_0^1 f_{gDNA}(AF_{gDNA}) \left[ \int_{k \cdot AF_{gDNA}}^1 f_{cfDNA}(AF_{cfDNA}) \cdot dAF_{cfDNA} \right] dAF_{gDNA} =$$

$$\int_0^1 f_{gDNA}(AF_{gDNA})(1 - F_{cfDNA}(k \cdot AF_{gDNA})) dAF_{gDNA}$$

As shown in the above equations, the sequence processor 205 determines a cumulative sum $F_{cfDNA}$ of the likelihood of the true AF of cfDNA. Furthermore, the sequence processor 205 integrates over the likelihood function of the true AF of gDNA. In another embodiment, the sequence processor 205 may determine the cumulative sum for the likelihood of the true AF of gDNA, and integrates over the likelihood function of the true AF of cfDNA. By calculating the cumulative sum of one of the two likelihoods (e.g., building a cumulative distribution function), instead of computing a double integral over both likelihoods for cfDNA and gDNA, the sequence processor 205 reduces the computational resources (expressed in terms of compute time or other similar metrics) required to determine whether the joint likelihood satisfies the criteria and may also increase precision of the calculation of the posterior probability.

VI. B. Example Noise of Joint Model

To account for noise in the estimated values of the true AF introduced by noise in the cfDNA and gDNA samples, the joint model 225 may use other models of the processing system 200 previously described with respect to FIGS. 4-9. In an embodiment, the noise components shown in the above equations for $P(AD_{cfDNA}|depth_{cfDNA}, AF_{cfDNA})$ and $P(AD_{gDNA}|depth_{gDNA}, AF_{gDNA})$ are determined using Bayesian hierarchical models 225, which may be specific to a candidate variant (e.g., SNV or indel). Moreover, the Bayesian hierarchical models 225 may cover candidate variants over a range of specific positions of nucleotide mutations or indel lengths.

In one example, the joint model 225 uses a function parameterized by cfDNA-specific parameters to determine a noise level for the true AF of cfDNA. The cfDNA-specific parameters may be derived using a Bayesian hierarchical model 225 trained with a set of cfDNA samples, e.g., from healthy individuals. In addition, the joint model 225 uses another function parameterized by gDNA-specific parameters to determine a noise level for the true AF of gDNA. The gDNA-specific parameters may be derived using another Bayesian hierarchical model 225 trained with a set of gDNA samples, e.g., from the same healthy individuals. In an embodiment, the functions are negative binomial functions having a mean parameter m and dispersion parameter $\tilde{r}$, and may also depend on the observed depths of sequence reads from the training samples:

$$\text{noise}_{cfDNA} = NB(m_{cfDNA} \cdot depth_{cfDNA}, \tilde{r}_{cfDNA})$$

$$\text{noise}_{gDNA} = NB(m_{gDNA} \cdot depth_{gDNA}, \tilde{r}_{gDNA})$$

In other embodiments, the sequence processor 225 may use a different type of function and types of parameters for cfDNA and/or gDNA. Since the cfDNA-specific parameters and gDNA-specific parameters are derived using different sets of training data, the parameters may be different from each other and particular to the respective type of nucleic acid sample. For instance, cfDNA samples may have greater variation in AF than gDNA samples, and thus $\tilde{r}_{cfDNA}$ may be greater than $\tilde{r}_{gDNA}$. The methods described above with respect to FIGS. 8, 9, and 10 are, in various embodiments, performed on a computer, such as computing device 160 shown in FIG. 1A.

VII. Examples for Joint Models

The example results shown in the following figures were determined by the processing system 100 using one or more trained joint models 225. In various embodiments, the results were generated using a targeted sequencing assay utilizing GRAIL's (GRAIL, Inc., Menlo Park, CA) proprietary 508 cancer gene panel to evaluate and call variants from targeted sequencing data from circulating cell-free DNA (cfDNA) samples obtained from subjects in one of two studies, Study "A" and Study "B," as indicated in the figures. Study A included sequencing data from plasma samples obtained from 50 healthy subjects (no diagnosis of cancer) and 50 samples each from subjects with pre-metastatic breast cancer and pre-metastatic non-small cell lung cancer. Study B included evaluable sequencing data from plasma samples obtained from 124 cancer patients (39 subjects with metastatic breast cancer (MBC), 41 subjects with non-small cell lung cancer (NSCLC), and 44 subjects with castration-resistant prostate cancer (CRCP).

Whole blood was drawn into STRECK Blood Collection Tubes (BCT®) from healthy individuals and cancer patients, separated into plasma and buffy coat, and stored at −80° C. Cell-free DNA (cfDNA) was extracted from the plasma using a modified QIAmp Circulating Nucleic Acid kit (QIAGEN®, Germantown, MD) and quantified using the Fragment Analyzer High Sensitivity NGS kit (ADVANCED ANALYTICAL TECHNOLOGIES®, Akneny IA). A sequencing library was prepared from extracted cfDNA with a modified Illumina TruSeq DNA Nano protocol (ILLUMINA®; San Diego, CA). The library preparation protocol included adapter ligation of sequencing adapters comprising unique molecular identifiers (UMIs) used for error correction as described above. Sequencing libraries were PCR amplified and quantified using the Fragment Analyzer Standard Sensitivity NGS kit.

Quantified DNA libraries underwent hybridization-based capture with GRAIL's proprietary research panel targeting 508 cancer related genes (GRAIL, Inc., Menlo Park, CA). Target DNA molecules were first captured using biotinlyated single-stranded DNA hybridization probes and then enriched using magnetic streptavidin beads. Non-target molecules were removed using subsequent wash steps. Enriched libraries were sequenced on a HiSex X using the HiSeq X Reagent Kit v2.5 (ILLUMINA®; San Diego, CA) at a nominal raw target coverage of 60,000×. Four libraries were pooled per flowcell and dual indexing primer mix was included to enable dual sample indexing reads. The read lengths were set to 150, 150, 8, and 8, respectively for read 1, read 2, index read 1, and index read 2. The first 6 base reads in read 1 and read 2 were the UMI sequences.

VII. A. Example Parameters for Joint Model

Figure 12:
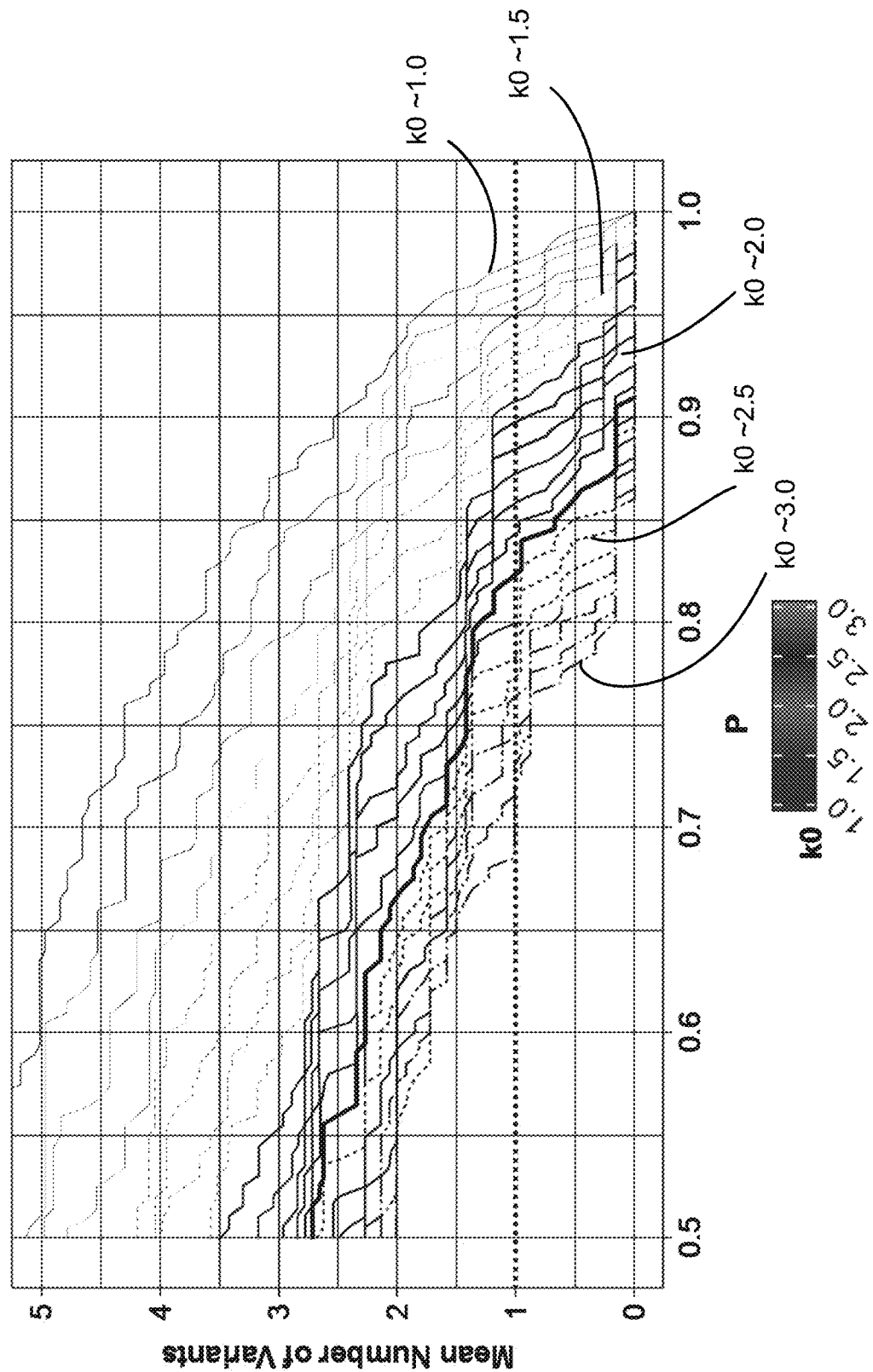
FIG. 12 is a diagram of observed counts of variants in samples from healthy individuals according to one embodiment.

FIG. 12 is a diagram of observed counts of variants in samples from healthy individuals according to one embodiment. Each data point corresponds to a position (across a range of nucleic acid positions) of a given one of the individuals. The parameters k and p used by the joint model 225 for joint likelihood computations may be selected empirically (e.g., to tune sensitivity thresholds) by cross-validating with sets of cfDNA and gDNA samples from healthy individuals and/or samples known to have cancer. The example results shown in FIG. 12 were obtained with study B and using blood plasma samples for the cfDNA and white blood cell samples for the gDNA. For given parameter values for k ("k0" as shown in FIG. 12) and p, the diagram plots a mean number of variants, which represents a computed upper confidence bound (UCB) of false positives for the corresponding sample. The diagram indicates that the number of false positives decreases as the value of p increases. In addition, the plotted curves have greater numbers of false positives for lower values of k, e.g., closer to 1.0. The dotted line indicates a target of one variant, though the empirical results show that the mean number of false positives mostly fall within the range of 1-5 variants, for k values between 1.0 and 5.0, and p values between 0.5 and 1.0.

The selection of parameters may involve a tradeoff between a target sensitivity (e.g., adjusted using k and p) and target error (e.g., the upper confidence bound). For given pairs of k and p values, the corresponding mean number of false positives may be similar in value, though the sensitivity values may exhibit greater variance. In some embodiments, the sensitivity is measured using percent positive agreement (PPA) values for tumor, in contrast to PPA for cfDNA, which may be used a measurement of specificity:

$$PPA_{tumor} = \frac{tumor + cfDNA}{tumor}$$

$$PPA_{cfDNA} = \frac{tumor + cfDNA}{cfDNA}$$

In the above equations, "tumor" represents the number of mean variant calls from a ctDNA sample using a set of parameters, and "cfDNA" represents the number of mean variant calls from the corresponding cfDNA sample using the same set of parameters.

In an embodiment, cross-validation is performed to estimate the expected fit of the joint model 225 to sequence reads (for a given type of tissue) that are different from the sequence reads used to train the joint model 225. For example, the sequence reads may be obtained from tissues having lung, prostate, and breast cancer, etc. To avoid or reduce the extent of overfitting the joint model 225 for any given type of cancer tissue, parameter values derived using samples of a set of types of cancer tissue are used to assess statistical results of other samples known to have a different type of cancer tissue. For instance, parameter values for lung and prostate cancer tissue are applied to a sample having breast cancer tissue. In some embodiments, one or more lowest k values from the lung and prostate cancer tissue data that maximizes the sensitivity is selected to be applied to the breast cancer sample. Parameter vales may also be selected using other constraints such as a threshold deviation from a target mean number of false positives, or 95% UCB of at most 3 per sample. The processing system 200 may cycle through multiple types of tissue to cross validate sets of cancer-specific parameters.

Figure 13:
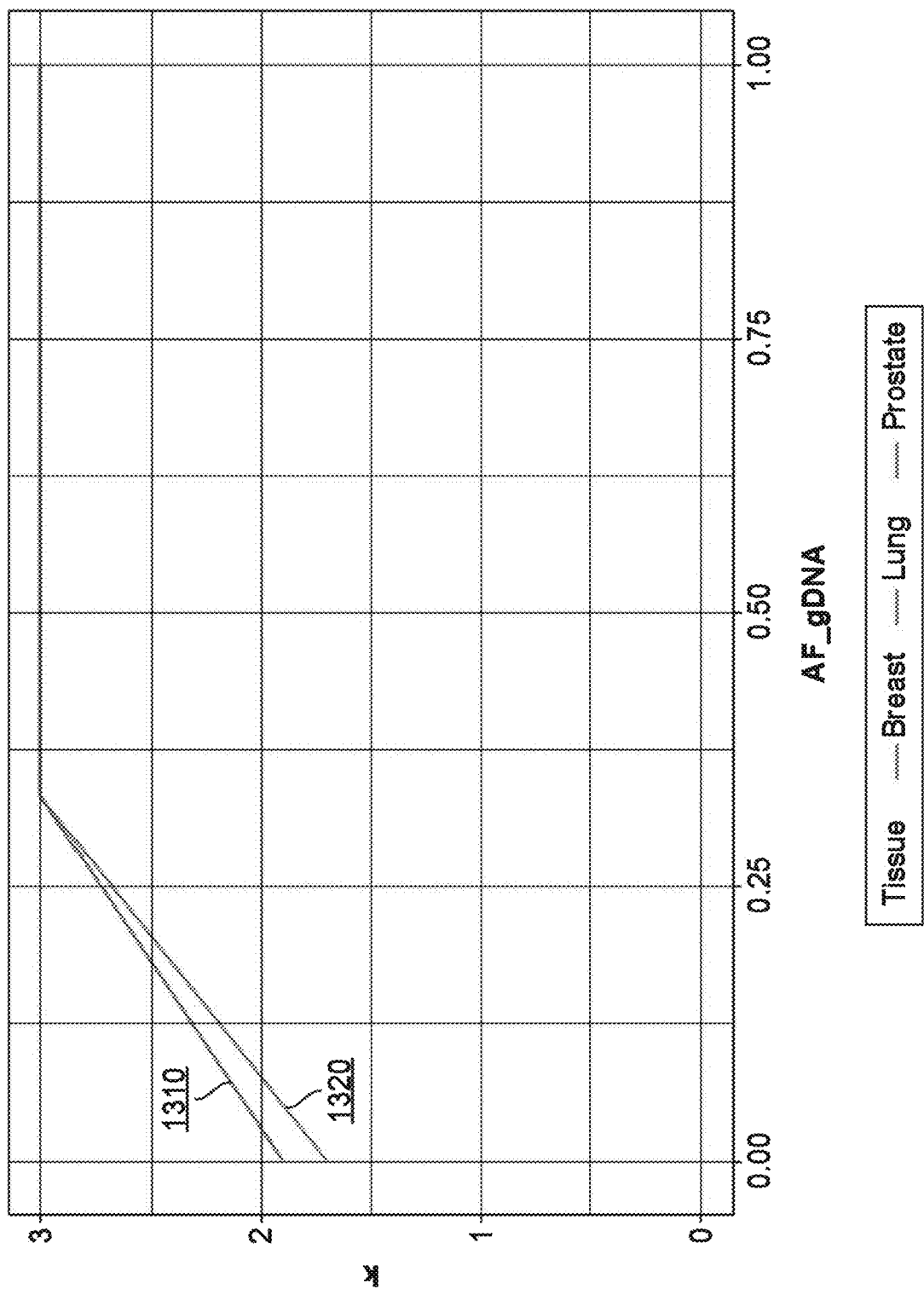
FIG. 13 is a diagram of example parameters for a joint model according to one embodiment.

FIG. 13 is a diagram of example parameters for a joint model 225 according to one embodiment. The parameter values for k may be determined as a function of AF observed in gDNA samples, and may vary based on a particular type of cancer tissue, e.g., breast, lung, or prostate as illustrated. The curve 1310 represents parameter values for breast and prostate cancer tissue, and the curve 1320 represents parameters values for lung cancer tissue. Although the examples thus far describe k and p generally and with reference to implementations where these parameters are fixed, in practice k and p may vary as any function of AF observed in the gDNA sample. In the example shown in the FIG. 13, the function is a hinge loss function with a hinge value (or lower threshold value), e.g., one-third. Specifically, the function specifies that k equal a predetermined upper threshold, e.g., 3, for $AF_{gDNA}$ values greater than or equal to the hinge value. For $AF_{gDNA}$ values less than the hinge value, the corresponding k values modulates with $AF_{gDNA}$. The example of FIG. 13 specifically illustrates that the k values for $AF_{gDNA}$ values less than one-third may be proportional to $AF_{gDNA}$ according to a coefficient (e.g., slope in the case of a linear relationship), which may vary between types of cancer tissue. In other embodiments, the joint model 225 can use another type of loss function such as square loss, logistic loss, cross entropy loss, etc.

The joint model 225 may alter k according to a hinge loss function or another function to guard against non-tumor or disease related effects where a fixed value for k would not accurately capture and categorize those events. The hinge loss function example is particularly targeted at handling loss of heterozygosity (LOH) events. LOH events are germline mutations that occur when a copy of a gene is lost from one of an individual's parents. LOH events may contribute to significant portions of observed AF of a gDNA sample. By capping the k values to the predetermined upper threshold of the hinge loss function, the joint model 225 may achieve greater sensitivity for detecting true positives in most sequence reads while also controlling the number of false positives that would otherwise be flagged as true positives due to the presence of LOH. In other embodiments, k and p may be selected based on training data specific to a given application of interest, e.g., having a target population or sequencing assay.

In some embodiments, the joint model 225 takes into account both the AF of a gDNA sample and a quality score of the gDNA sample to guard against underweighting low AF candidate variants. As previously described with reference to FIGS. 3, 4, and 9, the quality score generated by the score engine 235 for a noise model may be used to estimate the probability of error on a Phred scale. Additionally, the joint model 225 may use a modified piecewise function for the hinge function. For example, the piecewise function includes two or more additive components. One component is a linear function based on the AF of the gDNA sample, and another component is an exponential function based on the quality score of the gDNA sample. Given a quality score threshold and a maximum AF scaling factor $k_{max}$, the joint model 225 determines, using the exponential component of the piecewise function:

$$k_{max} \cdot P(\text{not error}) = \frac{1 - P(\text{error})}{P(\text{error})_{min}}$$

In the above calculation, P(not error) is the probability that an allele of the gDNA sample is not an error, P(error) is the probability that the allele of the gDNA sample is an error, and $P(\text{error})_{min}$ is a minimum probability of error. A minimum threshold for error rate may be empirically determined as the intersecting point for the quality score densities between the likely somatic and likely germline candidate variants of alleles of the gDNA sample.

VII. B. Example Variant Calls of Joint Model

Figure 14A:
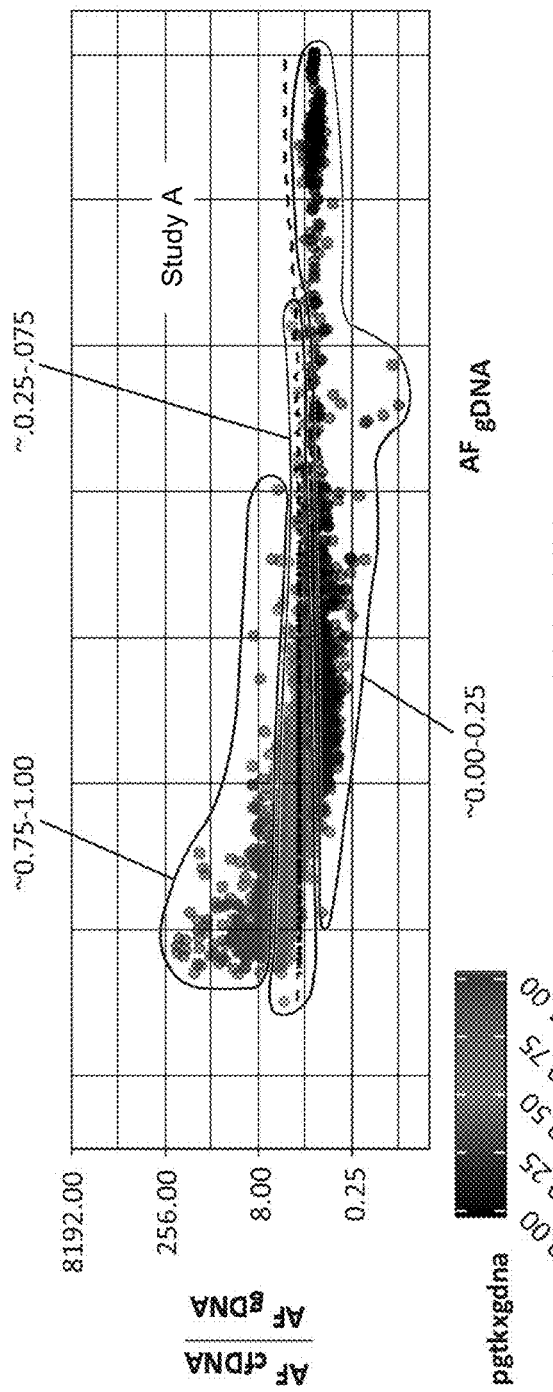
FIGS. 14A-B are diagrams of variant calls determined by a joint model according to one embodiment.
Figure 14B:
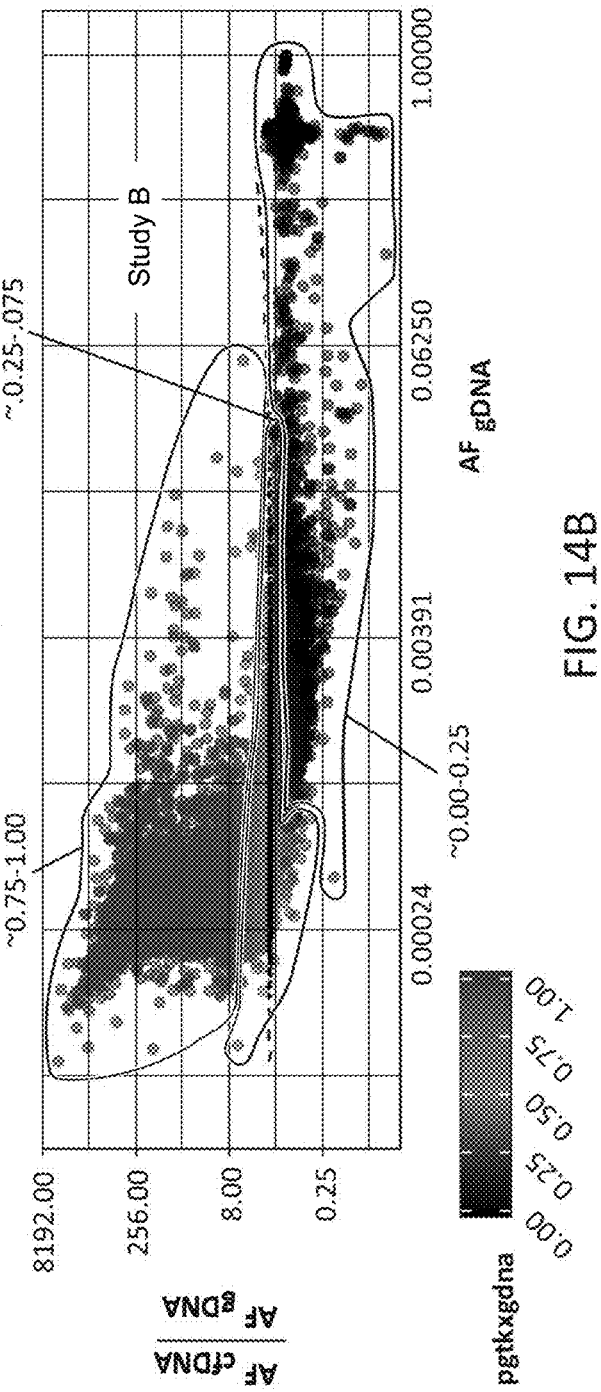

FIGS. 14A-B are diagrams of variant calls determined by a joint model according to one embodiment. The example results shown in FIG. 14A were obtained using study A and samples known to be affected by early stage cancer. The example results shown in FIG. 14B were obtained using study B and samples known to be affected by late stage cancer. The plots in FIGS. 14A-B share a common x-axis representing observed AF for gDNA. Further, the plots indicate that a variance of the ratio of observed AF of samples of cfDNA and gDNA is greater for late stage cancer than for early stage cancer. The variant caller 240 determines the posterior probability $P(AF_{cfDNA} \geq k \cdot AF_{gDNA})$ for pairs of $AF_{cfDNA}$ and $AF_{gDNA}$ data points, where the gradients of the plots represent the range of probabilities. Each data point represents a candidate cfDNA variant (e.g., for a given nucleic acid position) in an individual, and the plots include data points for multiple individuals in a data set. In the embodiment illustrated, the posterior probability is closer to 1.0 for ratios greater than 8.00 and $AF_{gDNA}$ values less than 0.00391, while the posterior probability is closer to 0.0 for ratios approaching 0.25.

Figure 15:
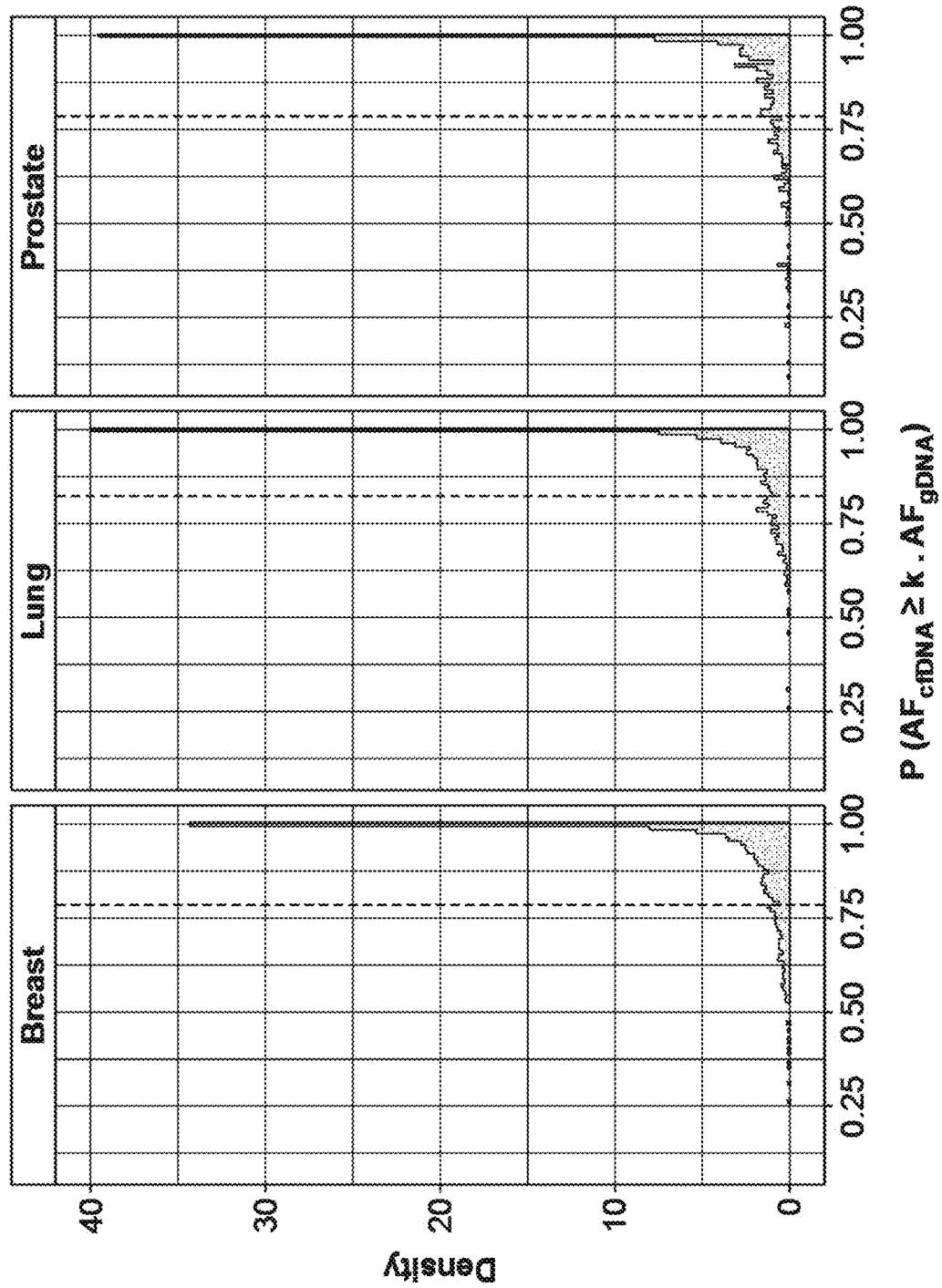
FIG. 15 is a diagram of probability densities determined by a joint model according to one embodiment.

FIG. 15 is a diagram of probability densities determined by a joint model 225 according to one embodiment. The example results shown in FIG. 15 were determined using sequence reads from breast, lung, and prostate tissue samples with an observed AF of gDNA that equals 0. FIG. 15 illustrates some general points about the joint model 225, regardless of the specific implementation. In such cases where no ALTs are observed ($AF_{gDNA}=0$), or where low numbers of ALTs are observed in gDNA, the processing system 200 may have a low confidence level regarding the source of ALTs observed in the corresponding cfDNA samples. These situations may occur due to background noise or low depth of the gDNA sample. Since the sequence processor 205 may not necessarily detect all of the ALTs of the gDNA sample, sequence reads of the cfDNA may still include false positives even when observed $AF_{gDNA}=0$. Additionally, the joint model 225 models $AF_{gDNA}$ as a distribution with noise, so the true $AF_{gDNA}$ may be modeled as a distribution over non-zero values of likelihood. As a consequence, in these conditions the variant caller 240 may filter out ALTs observed in cfDNA samples due to the low confidence of the source of the ALTs, for example, where it is uncertain whether the observed ALTs originated from gDNA or from cancer or diseased cells. In an embodiment, the variant caller 240 filters out data points having a probability less than a threshold probability, as illustrated by the dotted line in FIG. 15.

VII. C. Example Percent Positive Agreement of Joint Model

FIG. 16 is a diagram of sensitivity and specificity of a joint model 225 according to one embodiment. The variant caller 240 determines the sensitivity (e.g., $PPA_{tumor}$) and, specificity (e.g., $PPA_{cfDNA}$) measurements in studies A and B and with healthy samples, as well as samples known to have breast, lung, and prostate cancer. In comparison to the example results obtained using an empirical threshold, the example results obtained using the joint model 225 show a slight decrease in sensitivity, e.g., 0.14 decreased to 0.12 for $PPA_{tumor}$ of study A using lung tissue samples. However, the joint model 225 results show a greater increase in specificity, e.g., 0.12 increased to 0.22 for $PPA_{cfDNA}$ of study A using lung tissue samples.

VII. D. Example Detected Genes Using Joint Model

Figure 17:
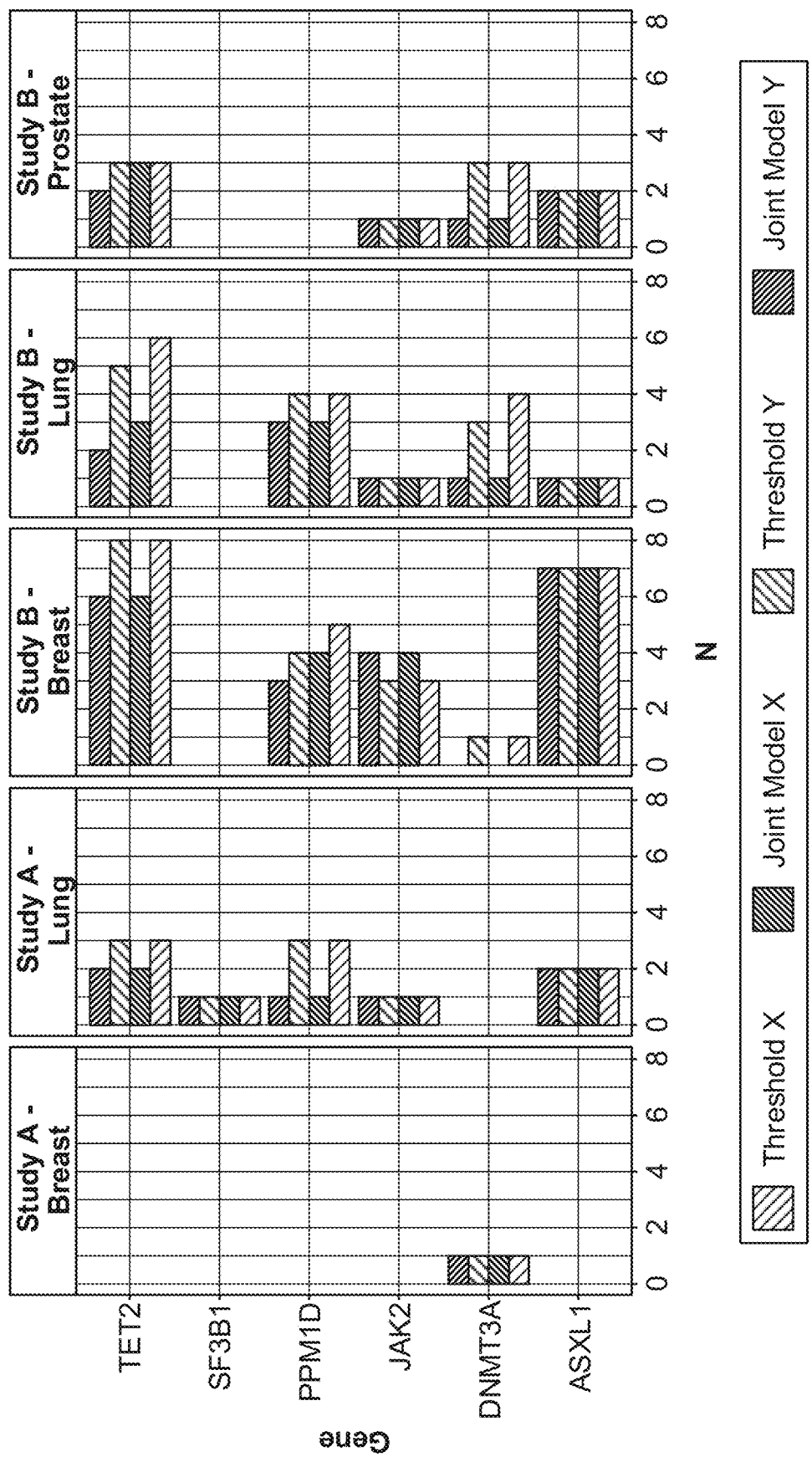
FIG. 17 is a diagram of a set of genes detected from targeted sequencing assays using a joint model according to one embodiment.
Figure 18:
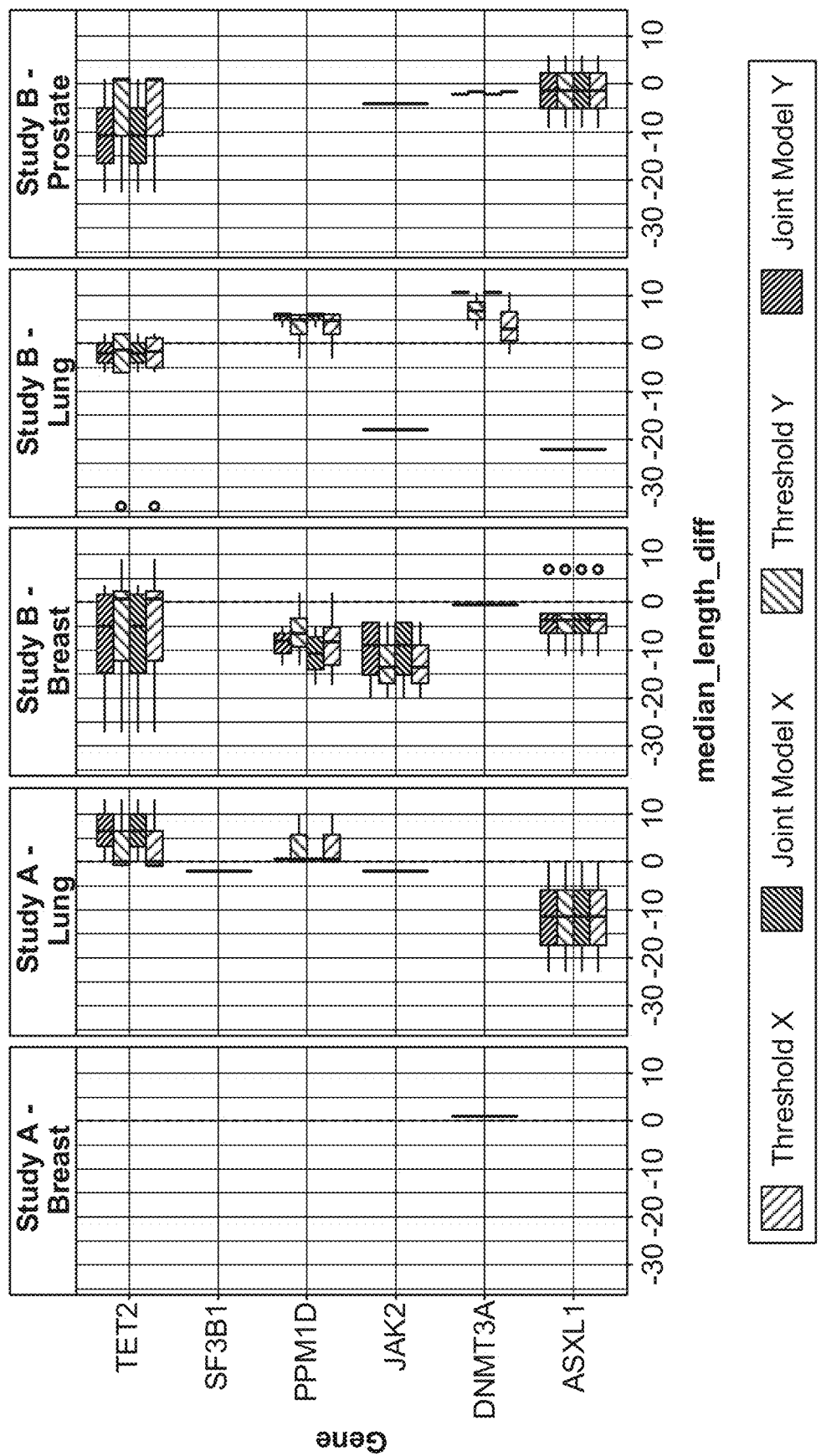
FIG. 18 is a diagram of length distributions of the set of genes shown in FIG. 17 detected from targeted sequencing assays using the joint model according to one embodiment.
Figure 19:
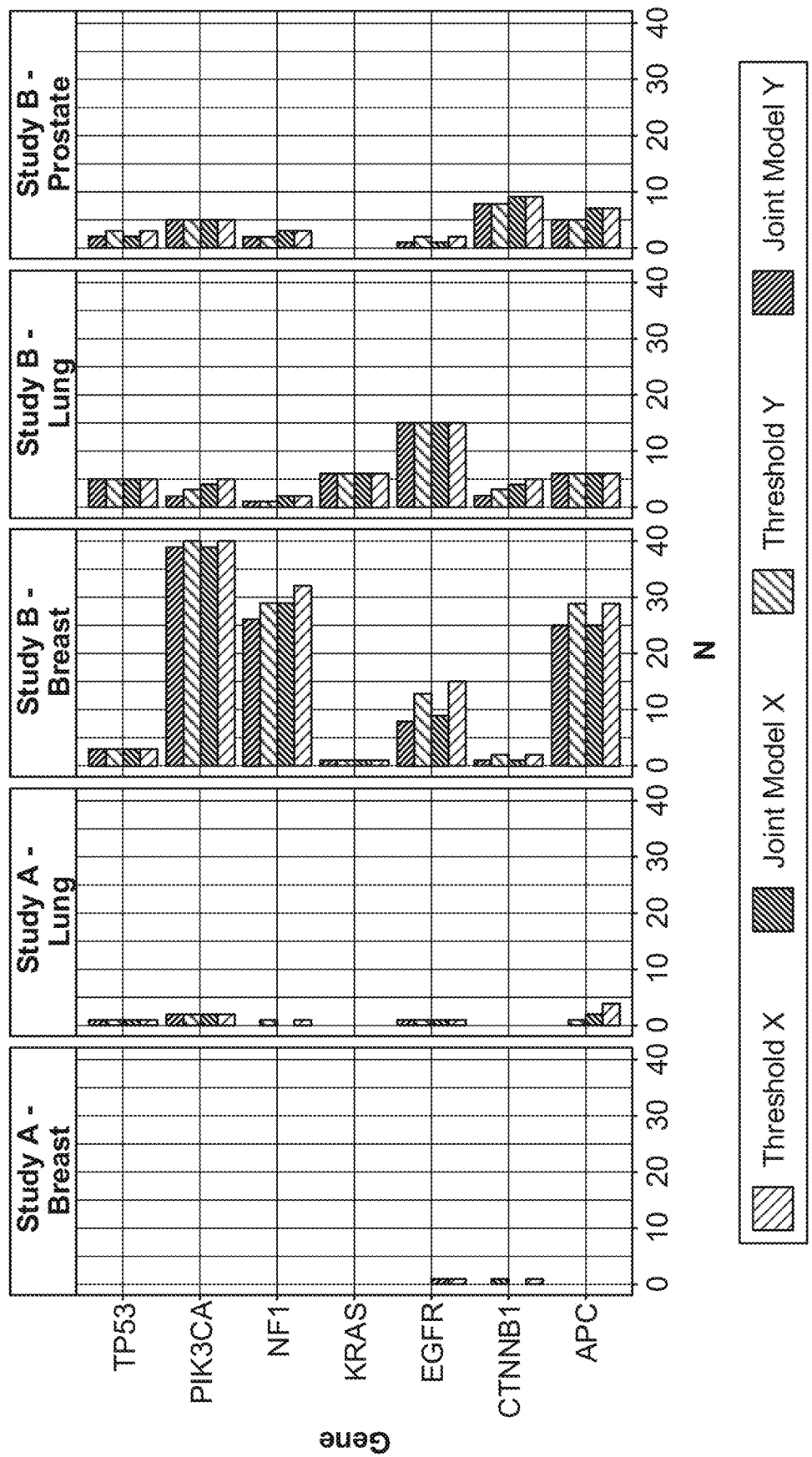
FIG. 19 is a diagram of another set of genes detected from targeted sequencing assays using a joint model according to one embodiment.

FIG. 17 is a diagram of a set of genes detected from targeted sequencing assays using a joint model 225 according to one embodiment. The set includes genes that are commonly mutated during clonal hematopoiesis. The sequence processor 205 determines the results in studies A and B and samples known to have breast, lung, and prostate cancer. The tests "Threshold X" and "Joint Model X" do not include nonsynonymous mutations, while the tests "Threshold Y" and "Joint Model Y" do include nonsynonymous mutations. The example results obtained using the joint model 225 reduces the counts (denoted as "n" on the x-axis as shown in FIGS. 17-19) of detected germline mutations from samples of various types of tissue, in comparison to the counts detected using an empirical threshold. For instance, as illustrated by the graph for study B with lung cancer, "Threshold X" and "Threshold Y" results in counts of 5 and 6 detected TET2 genes, respectively. The "Joint Model X" and "Joint Model Y" results in counts of 2 and 3 detected TET2 genes, respectively, which indicates that the joint model 225 provides improved sensitivity.

FIG. 18 is a diagram of length distributions of the set of genes shown in FIG. 17 detected from targeted sequencing assays using a joint model 225 according to one embodiment. Generally, nucleic acid fragments that originate from tumor or diseased cells have shorter lengths (e.g., of nucleotides) than those that originate from reference alleles. As shown in the box plot results for study B with the breast cancer sample, the median differences in length between detected ALTs and reference alleles for the TET2 gene are approximately zero for both "Threshold X" and "Threshold Y." In contrast, the median differences in length between detected ALTs and reference alleles for the TET2 gene are approximately −5 for both "Joint Model X" and "Joint Model Y." Thus, the variant caller 240 may determine with greater confidence that the detected ALTs potentially originated from a tumor or diseased cell, instead of a reference allele. Moreover, the example results indicate that the joint model 225 can perform variant calls of short fragments of sequence reads in samples with varying noise levels.

FIG. 19 is a diagram of another set of genes detected from targeted sequencing assays using a joint model 225 according to one embodiment. The example results indicate that the sensitivity for detecting driver genes of the joint model 225 is comparable to that of filters that do not use a model. That is, the joint model 225 does not significantly over filter the detected driver genes relative to the results obtained using an empirical threshold.

VIII. Example Tuning of Joint Model

FIG. 20 is flowchart of a method 2000 for tuning a joint model 225 to process cell free nucleic acid (e.g., cfDNA) samples and genomic nucleic acid (e.g., gDNA) samples according to one embodiment. The method 2000 may be performed in conjunction with the methods 800, 900, and/or 1000 shown in FIGS. 8-10, or another similar method. For example, the method 1000 is performed using a joint model 255 to determine the probability for step 2010 of the method 2000. The examples described with respect to FIGS. 20-22 reference blood (e.g., white blood cells) of a subject as the source of the gDNA sample, though it should be noted that in other embodiments, the gDNA may be from a different type of biological sample. The processing system 200 may implement at least a portion of the method 2000 as a decision tree to filter or process candidate variants in the cfDNA sample. For instance, the processing system 200 determines whether a candidate variant is likely associated or not with the gDNA sample, or if an association is uncertain. An association may indicate that the variant can be accounted for by a mutation in the gDNA sample (e.g., due to factors such as germline mutations, clonal hematopoiesis, artifacts, edge variants, human leukocyte antigens such as HLA-A, etc.) and thus likely not tumor-derived and not indicative of cancer or disease. The method 2000 may include different or additional steps than those described in conjunction with FIG. 20 in some embodiments or perform steps in different orders than the order described in conjunction with FIG. 20.

VIII. A. Example Quality Score and Ratio of Joint Model

In step 2010, the sequence processor 205 determines a probability that the true alternate frequency of a cfDNA sample is greater than a function of a true alternate frequency of a gDNA sample. Step 2010 may correspond to previously described step 1050 of the method 1000 shown in FIG. 10.

In step 2020, the sequence processor 205 determines whether the probability is less than a threshold probability. As an example, the threshold probability may be 0.8, however in practice the threshold probability may be any value between 0.5 and 0.999 (e.g., determined based on a desired filtering stringency), static or dynamic, vary by gene and/or set by position, or other macro factors, etc. Responsive to determining that the probability is greater than or equal to the threshold probability, the sequence processor 205 determines that the candidate variant is likely not associated with the gDNA sample such as a blood draw including white blood cells of a subject, i.e., not blood-derived. For example, the candidate variant is typically not present in sequence reads of the gDNA sample for a healthy individual. Accordingly, the variant caller 240 may call the candidate variant as a true positive that potentially associated with cancer or disease, e.g., potentially tumor-derived.

In step 2030, the sequence processor 205 determines whether the alternate depth of the gDNA sample is significantly the same as or different than zero. For instance, the sequence processor 205 performs an assessment using a quality score of the candidate variant determined by the score engine 235 using a noise model 225 as previously described with reference to FIGS. 3, 4, and 9. The sequence processor 205 may also compare the alternate depth against a threshold depth, e.g., determining whether the alternate depth is less than or equal to a threshold depth. As an example, the threshold depth may be 0 or 1 reads. Responsive to determining that the alternate depth of the gDNA sample is significantly different than zero, the sequence processor 205 determines that there is positive evidence that the candidate variant is associated with nucleotide mutations not caused by cancer or disease. For instance, the candidate variant is blood-derived based on mutations that may typically occur in sequence reads of healthy white blood cells.

Responsive to determining that the alternate depth of the gDNA sample is not significantly nonzero, the sequence processor 205 determines that the candidate variant is possibly associated with the gDNA sample, but does not make a determination of a source of the candidate variant without further checking by the score engine 235 as described below. In other words, the sequence processor 205 may be uncertain about whether the candidate variant is blood-derived or tumor-derived. In some embodiments, the sequence processor 205 may select one of multiple threshold depths for comparison with the alternate depth. The selection may be based on a type of processed sample, noise level, confidence level, or other factors.

In step 2040, the score engine 235 determines a gDNA depth quality score of sequence reads of the gDNA sample. In an embodiment, the score engine 235 calculates the gDNA depth quality score using the an alternate depth of the gDNA sample, where C is a predetermined constant (e.g., 2) to smooth the gDNA depth quality score using a weak prior, which avoids divide-by-zero computations:

$$AD_{gDNA} \text{ depth quality score} = \frac{AD_{gDNA}}{\sqrt{AD_{gDNA} + C}}$$

In step 2050, the score engine 235 determines a ratio of sequence reads of the gDNA sample. The ratio may represent the observed cfDNA frequency and observed gDNA frequency in the processed samples. In an embodiment, the score engine 235 calculates the ratio using the depths and alternate depths of the cfDNA sample and gDNA sample:

$$\text{ratio} = \frac{(AD_{cfDNA} + C_1)(depth_{gDNA} + C_2)}{(AD_{gDNA} + C_3)(depth_{cfDNA} + C_4)}$$

The score engine 235 may use the predetermined constants $C_1$, $C_2$, $C_3$, and $C_4$ to smooth the ratio by a weak prior. As examples, the constants may be: $C_1=2$, $C_2=4$, $C_3=2$, and $C_4=4$. Thus, the score engine 235 may avoid a divide-by-zero computation if one of the depths or alternate depths in the ratio denominator equals zero. Thus, the score engine 235 may use the predetermined constants to steer the ratio to a certain value, e.g., 1 or 0.5.

In step 2060, the sequence processor 205 determines whether the gDNA depth quality score is greater than or equal to a threshold score (e.g., 1) and whether the ratio is less than a threshold ratio (e.g., 6). Responsive to determining that the gDNA depth quality score is less than the threshold score or that the ratio is greater than or equal to the threshold ratio, the sequence processor 205 determines that there is uncertain evidence regarding association of the candidate variant with the gDNA sample. Stated differently, the sequence processor 205 may be uncertain about whether the candidate variant is blood-derived or tumor-derived because the candidate variant appears "bloodish" but there is not definitive evidence that a corresponding mutation is found in healthy blood cells.

In step 2070, responsive to determining that the gDNA depth quality score is greater than or equal to the threshold score and that the ratio is less than the threshold ratio, the sequence processor 205 determines that the candidate variant is likely associated with a nucleotide mutation of the gDNA sample. In other words, the sequence processor 205 determines that although there is not definitive evidence that a corresponding mutation is found in healthy blood cells, the candidate variant appears "bloodier" than normal.

Thus, the sequence processor 205 may use the ratio and gDNA depth quality score to tune the joint model 225 to provide greater granularity in determining whether certain candidate variants should be filtered out as false positives (e.g., initially predicted as tumor-derived, but actually blood-derived), true positives, or uncertain due to insufficient evidence or confidence to classify into either category. For example, based on the result of the method 2000, the sequence processor 205 may modify one or more of the parameters (e.g., k parameter) for a hinge loss function of the joint model 225. In some embodiments, the sequence processor 205 uses one or more steps of the method 2000 to assign candidate variants to different categories, for instance, "definitively," "likely," or "uncertain" association with gDNA (e.g., as shown in FIGS. 21A-B).

VIII. B. Example Decision Tree

In various embodiments, the processing system 200 processes candidate variants using one or more filters in addition to the steps described with reference to the flowchart of the method 2000 shown in FIG. 20. The sequence processor 205 may implement the filters in a sequence as part of a decision tree, where the sequence processor 205 continues to check criteria of the filters until a given candidate variant "exits" the decision tree, e.g., because the given candidate variant is filtered upon satisfying at least one of the criteria. A filtered candidate variant may indicate that the candidate variant can be accounted for by a source or cause of mutations naturally occurring in healthy individuals (e.g., associated with white blood cell gDNA) or due to process errors.

In some embodiments, the sequence processor 205 filters candidate variants of sequence reads of a cfDNA sample responsive to determining that there is no quality score for the sequence reads. The score engine 235 may determine quality scores for candidate variants using a noise model 225 as previously described with reference to FIGS. 3, 4, and 9. The score engine 235 may determine the quality scores with no base alignment. In some embodiments, the quality score may be missing for some samples or candidate variants due to a lack of training data for the joint model 225 or poor training data that fails to produce useful parameters for a given candidate variant. For instance, high noise levels in sequence reads may lead to unavailability of useful training data. The score engine 235 may tune specificity and selectivity of the joint model 225 based on whether a single variant is processed or if the sequence processor 205 is controlling for a targeted panel. As other examples, the sequence processor 205 filters a candidate variant responsive to determining that the candidate variant is an edge variant artifact, has less than a threshold cfDNA depth (e.g., 200 sequence reads), has less than a threshold cfDNA quality score (e.g., 60), or corresponds to human leukocyte antigens (HLA), e.g., HLA-A. Since sequences associated with HLA-A may be difficult to align, the sequence processor 205 may perform a custom filtering or variant calling process for sequences in these regions.

In some embodiments, the sequence processor 205 filters candidate variants determined to be associated with germline mutations. The sequence processor 205 may determine that a candidate variant is germline by determining that the candidate variant occurs at an appropriate frequency corresponding to a given germline mutation event and is present at a particular one or more positions (e.g., in a nucleotide sequence) known to be associated with germline events. Additionally, the sequence processor 205 may determine a point estimate of gDNA frequency, where C is a constant (e.g., 0.5):

$$point_{afDNA} = \frac{AD_{gDNA}}{depth_{gDNA} + C}$$

The sequence processor 205 may determine that a candidate variant is germline responsive to determining that $point_{afDNA}$ is greater than a threshold point estimate threshold (e.g., 0.3). In some embodiments, the sequence processor 205 filters candidate variants responsive to determining that a number of variants associated with local sequence repetitions is greater than a threshold value. For example, an "AAAAAA" or "ATATATAT" local sequence repetition may be result of a polymerase slip that causes an increase in local error rates.

VIII. C. Examples for Tuned Joint Model

FIG. 21A is a table of example counts of candidate variants of cfDNA samples according one an embodiment. The example data in FIGS. 21A-B and FIG. 22 were generated using sequence reads obtained from a sample set of individuals of the cell free genome study described below with reference to FIGS. 33A-C. The cfDNA samples include samples from individuals known to have cancer or another type of disease. In the example shown in FIG. 21A, the processing system 200 uses the method 2000 of FIG. 20 to determine that 23805 of the candidate variants are "definitively" associated with gDNA (e.g., accounted for by germline mutations or clonal hematopoiesis in blood) and that 1360 of the candidate variants are "likely" associated with gDNA (e.g., "bloodier" or greater than a threshold confidence level). Thus, the processing system 200 may filter out these candidate variants from the joint model 225 or another pipeline, e.g., such that these candidate variants are classified as blood-derived. The processing system 200 may determine to neither categorize the count of 2607 "uncertain" (e.g., "bloodish") candidate variants as tumor-derived nor blood-derived. Thus, by tuning the joint model 225, for example, using the gDNA ratio and gDNA depth quality score from the method 2000, the processing system 200 improves granularity (e.g., different levels of confidence) in classifying sources of candidate variants. FIG. 21B is a table of example counts of candidate variants of cfDNA samples from healthy individuals according to an embodiment. The example counts shown in FIGS. 21A-B were determined by the processing system 200 using a threshold depth of 200 reads, threshold quality score of 60 (e.g., on a Phred scale), quality score at the corresponding position having a mean squared deviation from germline mutation frequency threshold of 0.005, threshold point estimate of gDNA frequency of 0.3, threshold artifact recurrence rate of 0.05, threshold local sequence repetition count of 7, threshold probability (e.g., that the true alternate frequency of a cfDNA sample is greater than a function of a true alternate frequency of a gDNA sample) of 0.8, threshold gDNA depth of 0, threshold gDNA depth quality score of 1, and threshold gDNA sample ratio of 6. Furthermore, the processing system 200 filtered out candidate variants with no quality score, somatic variants, and HLA-A regions.

Figure 22:
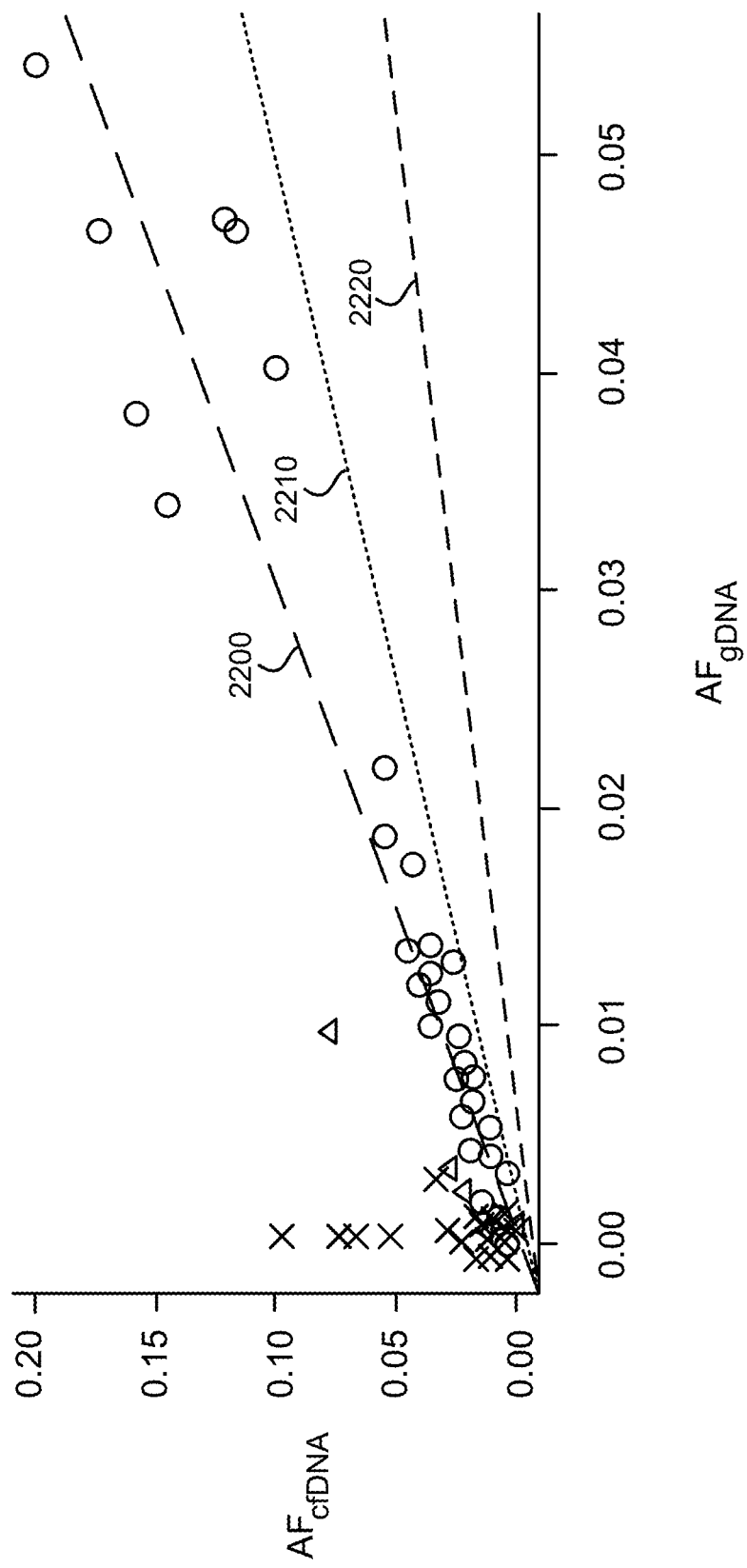
FIG. 22 is a diagram of candidate variants plotted based on ratio of cfDNA and gDNA according to one embodiment.

FIG. 22 is a diagram of candidate variants plotted based on ratio of cfDNA and gDNA according to one embodiment. For each of a number of plotted candidate variants of a subject, the x-axis value represents the AF observed in gDNA samples and the y-axis represents the AF observed in a corresponding cfDNA sample of the subject. The example shown in FIG. 22 includes candidate variants passed by a joint model 225 using a hinge function such as the curve 1310 or curve 1320 illustrated in FIG. 13. For this example data and the recited parameters above, the processing system 200 determines that the cluster of candidate variants depicted as cross marks toward the left of the plot, which have a relatively higher $AF_{cfDNA}$ to $AF_{gDNA}$ ratio, are likely to be not associated with nucleotide mutations naturally occurring in white blood cells, and thus predicted as tumor-derived. The dotted line 2220 is a reference line representing a 1:1 $AF_{cfDNA}$ to $AF_{gDNA}$ ratio. A hinge function is represented by the dotted graphic 2210, which may not necessarily be a line (e.g., may include multiple segments connected at one or more hinges). The cluster of candidate variants depicted as circles have relatively lower $AF_{cfDNA}$ to $AF_{gDNA}$ ratios, but were still passed by the joint model 225 when using the hinge function represented by 2210 (e.g., because several of the candidate variants are plotted above 2210. However, some of these candidate variants may actually be associated with gDNA, e.g., blood-derived, and should be filtered out instead of being called as tumor-derived. The dotted line 2200 is a regression line determined using robust fit regression on the clusters of data points depicted in the cross marks. By tuning the hinge function using the regression line 2200, the joint model 225 can filter out more of the candidate variants that may actually be blood-derived. In some embodiments, 2200, 2210, and 2220 each intersect the origin (0, 0). The processing system 200 determines that there is uncertain evidence as to whether the cluster of candidate variants depicted as triangles (located generally between the clusters of cross marks and circle-type candidate variants) are blood or tumor-derived.

To improve the accuracy of catching these candidate variants, the processing system 200 may use the filters as described above with reference to FIG. 20. Further, the processing system 200 may tune the joint model 225 by using more aggressive parameters for a hinge function under certain conditions. For example, the processing system 200 uses a greater probability threshold (e.g., for step 2020 of the method 2000 shown in FIG. 20) responsive to determining that the AD of the gDNA sample is greater than a threshold depth (e.g., 0), which is supportive evidence of nucleotide mutations in blood of healthy samples. In some embodiments, the processing system 200 determines a modified hinge function (or another type of function for classifying true and false positives) using the greater probability threshold. For instance, the modified function may have a sharper cutoff (e.g., relative to the curves 1310 and 1320 of FIG. 13) that would filter out at least some candidate variants of the cluster along the dotted diagonal lines in FIG. 22. The processing system 200 may also tune the modified function using the gDNA sample quality score or ratio as determined in steps 2040 and 2050 of the method 2000, respectively.

IX. Example Edge Filtering

Figure 23A:
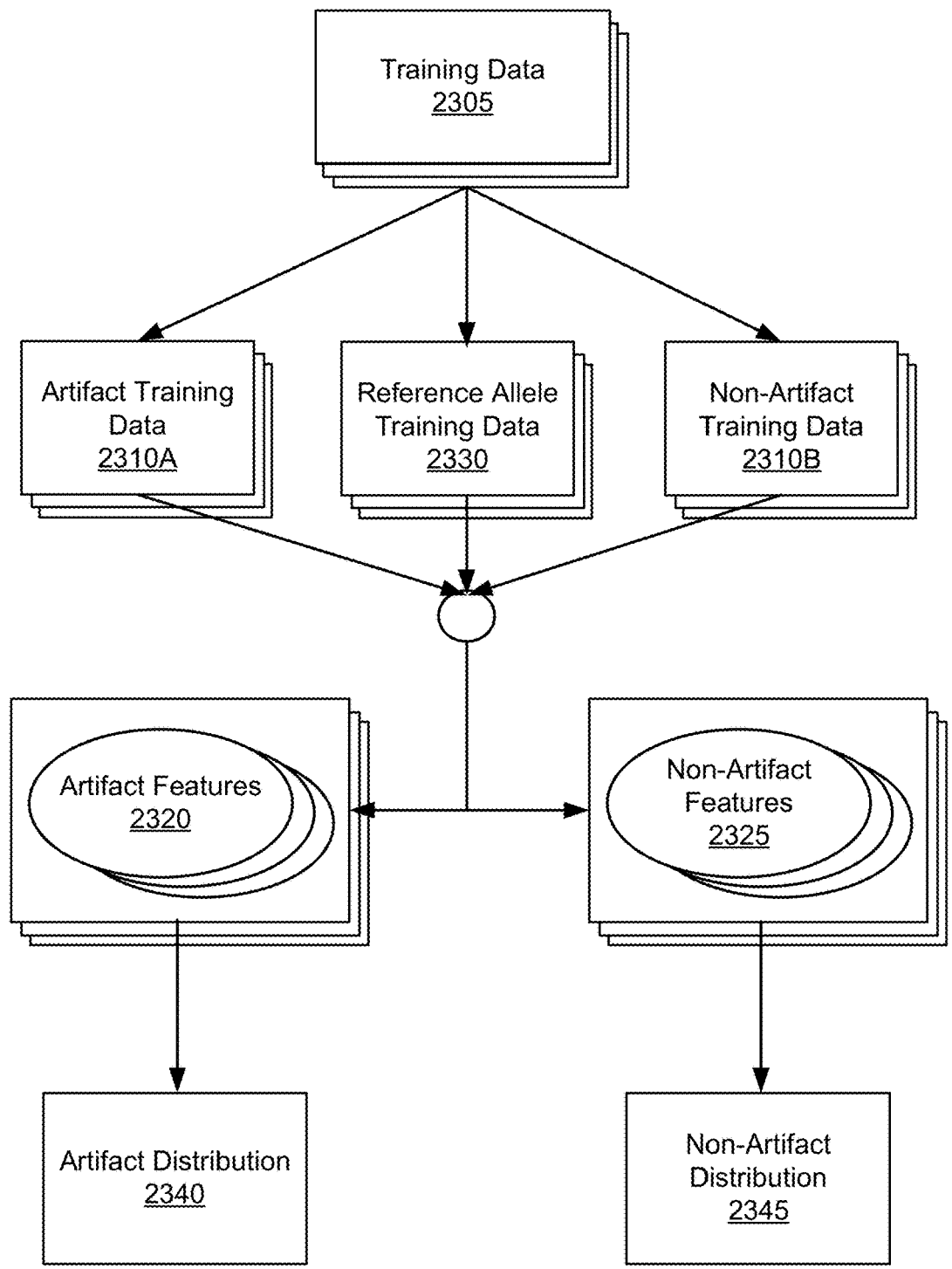
FIG. 23A depicts a process of generating an artifact distribution and a non-artifact distribution using training variants according to one embodiment.

IX. A. Example Training Distributions of Features from Artifact and Non-Edge Variants FIG. 23A depicts a process of generating an artifact distribution and a non-artifact distribution using training variants according to one embodiment. The edge filter 250 generates the artifact distribution 2340 and non-artifact distribution 2345 during a training process 2300 using training data 2305 from previous samples (e.g., training samples). Once generated, the artifact distribution 2340 and non-artifact distribution 2345 can each be stored (e.g., in the model database 215) for subsequent retrieval at a needed time.

Training data 2305 includes various sequence reads, such as sequence reads obtained from the enriched sequences 180 (see FIG. 1B). Sequence reads in the training data 2305 can correspond to various positions on the genome. In various embodiments, sequence reads in the training data 2305 are obtained from more than one training sample.

The edge filter 250 categorizes sequence reads in the training data 2305 into one of an artifact training data 2310A category, reference allele training data 2330 category, or non-artifact training data 2310B category. In various embodiments, sequence reads in the training data 2305 can also be categorized into a "no result" or a "no classification" category responsive to determining that the sequence reads do not satisfy the criteria to be placed in any of the artifact training data 2310A category, reference allele training data 2330 category, or non-artifact training data 2310B category.

As shown in FIG. 23A, there may be multiple groups of artifact training data 2310A, multiple groups of reference allele training data 2330, and multiple groups of non-artifact training data 2310B. Generally, sequence reads that are in a group cross over (overlap) a common position in the genome. In various embodiments, sequence reads in a group derive from a single training sample (e.g., a training sample obtained from a single individual) and cross over the common position in the genome. For example, given sequence reads from M different training samples obtained from M different individuals, there can be M different groups each including sequence reads from one of the M different training samples. Although the subsequent description refers to groups of sequence reads that cross over a common position on the genome, the description can be further expanded to other groups of sequence reads that cross over other positions on the genome.

Sequence reads that correspond to a common position on the genome include: 1) sequencing reads that include a nucleotide base at the position that is different from the reference allele (e.g., an ALT) and 2) sequencing reads that include a nucleotide base at the position that matches the reference allele. Referring again to FIG. 1B, a sequence read can be obtained from an enriched sequence 180 that includes an ALT (e.g., the thymine in enriched sequence 180A or 180C) or can include the reference allele (e.g., the cytosine in enriched sequence 180B).

The edge filter 250 categorizes sequence reads that include an ALT into one of the artifact training data 2310A or non-artifact training data 2310B. Specifically, sequence reads that satisfy one or more criteria are categorized as artifact training data 2310A. The criteria can be a combination of a type of mutation of the ALT and a location of the ALT on the sequence read. Referring to an example of a type of mutation, sequence reads categorized as artifact training data include an alternative allele that is either a cytosine to thymine (C>T) nucleotide base substitution or a guanine to adenine (G>A) nucleotide base substitution. Referring to an example of the location of the alternative allele, the alternative allele is less than a threshold number of base pairs from an edge of a sequence read. In one implementation, the threshold number of base pairs is 25 nucleotide base pairs, however, the threshold number may vary by implementation.

Figure 23B:
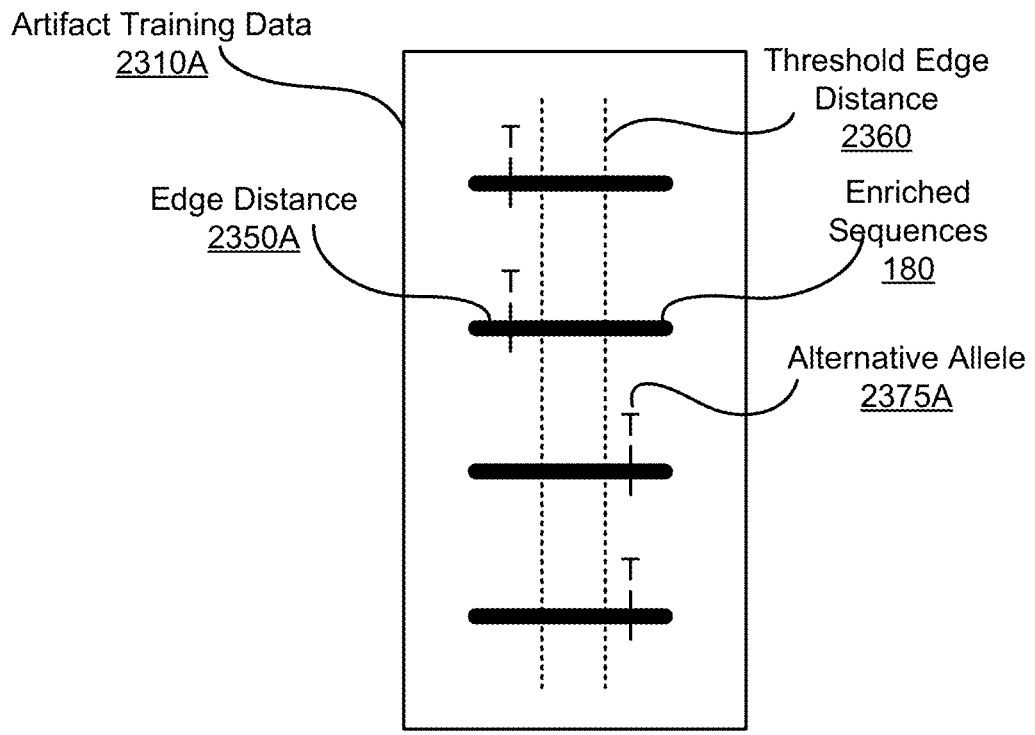
FIG. 23B depicts sequence reads that are categorized in an artifact training data category according to one embodiment.

FIG. 23B depicts sequence reads that are categorized in an artifact training data 2310A category according to one embodiment. Additionally, each of the sequence reads satisfy one or more criteria. For example, each sequence read includes an alternative allele 2375A that is a C>T nucleotide base substitution. Additionally, the alternative allele 2375A on each sequence read is located at an edge distance 2350A that is less than a threshold edge distance 2360.

Sequence reads with an alternative allele that are categorized into the non-artifact training data 2310B category are all other sequence reads with an alternative allele that do not satisfy the criteria of being categorized as artifact training data 2310A. For example, any sequence read that includes an alternative allele that is not one of a C>T or G>A nucleotide base substitution is categorized as a non-edge training variant. As another example, irrespective of the type of nucleotide mutation, any sequence read that includes an alternative allele that is located greater than a threshold number of base pairs from an edge of a sequence read is categorized as non-artifact training data 2310B. In one implementation, the threshold number of base pairs is 25 nucleotide base pairs, however, the threshold number may vary by implementation.

Figure 23C:
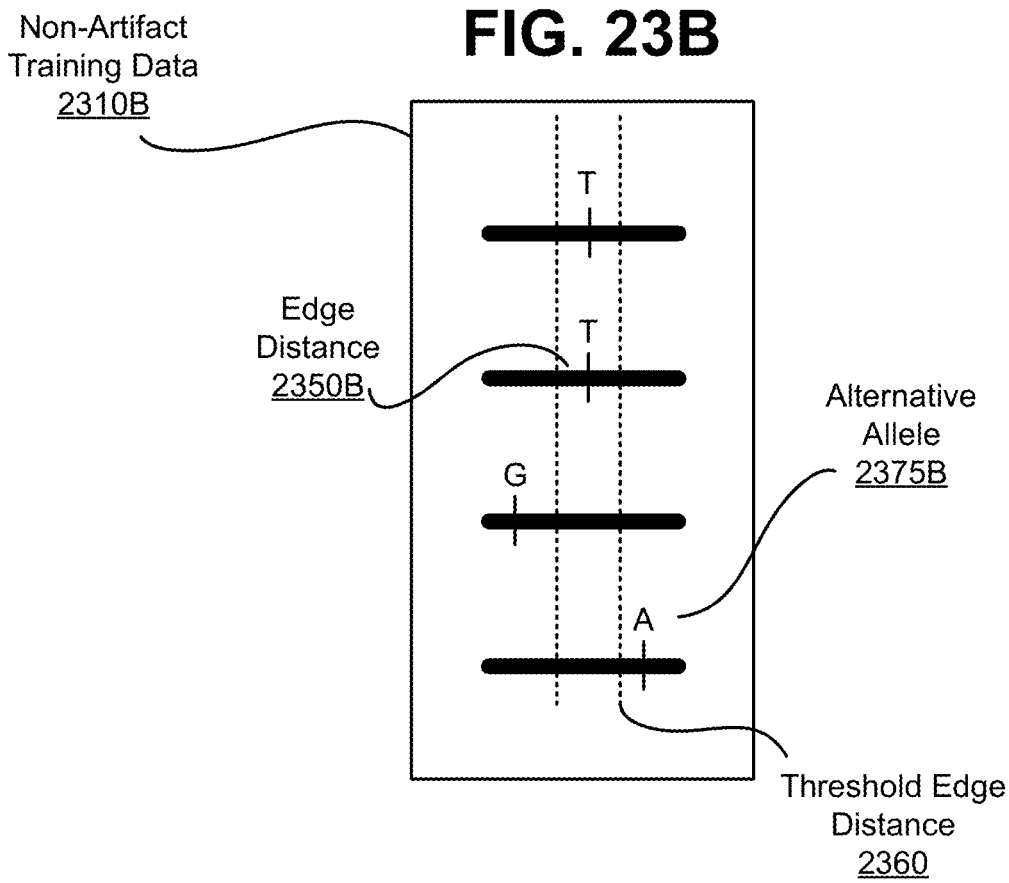
FIG. 23C depicts sequence reads that are categorized in the non-artifact training data category according to one embodiment.

FIG. 23C depicts sequence reads that are categorized in the non-artifact training data 2310B category according to one embodiment. Here, each of the sequence reads includes an alternative allele 2375B that does not satisfy both criteria. For example, each alternative allele 2375B can either be a non C>T or non G>A nucleotide base substitution, irrespective of the location of the alternative allele 2375B. As another example, each alternative allele 2375B is a C>T or G>A nucleotide base substitution, but is located with an edge distance 2350B that is greater than the threshold edge distance 2360.

Figure 23D:
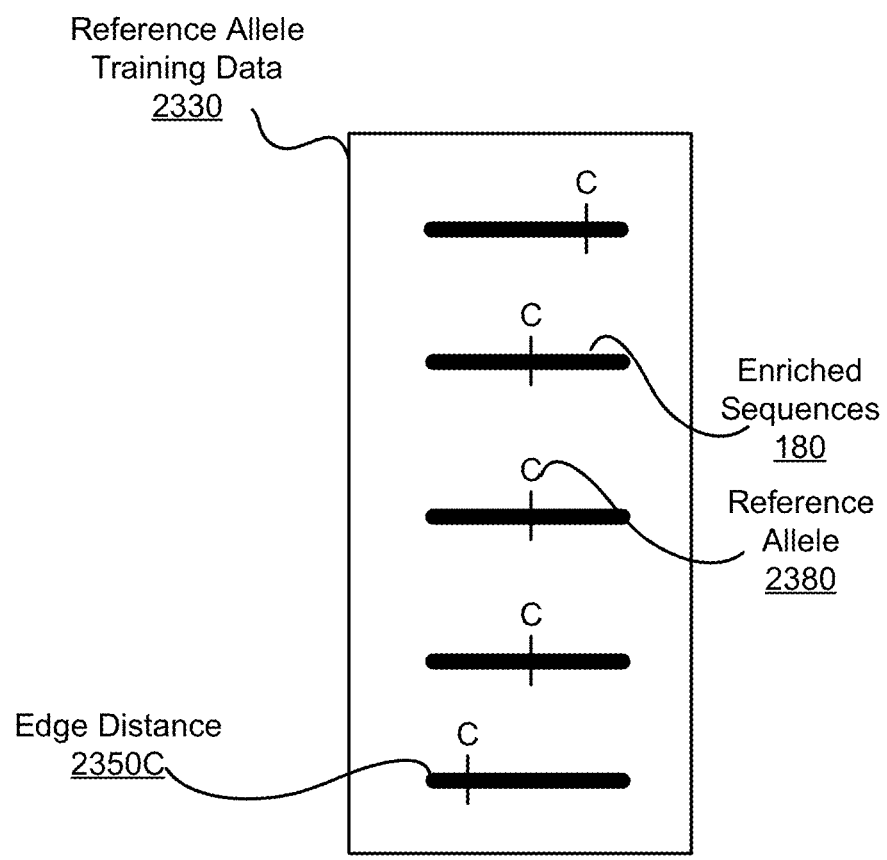
FIG. 23D depicts sequence reads that are categorized in the reference allele training data category according to one embodiment.

Referring now to the reference allele training data 2330 category, sequence reads that include the reference allele are categorized in the reference allele training data 2330 category. FIG. 23D depicts sequence reads corresponding to the same position in the genome that are categorized in the reference allele training data 2330 category according to one embodiment. As an example, the sequence reads shown in FIG. 23D each include the reference allele 2380 (which matches the cytosine nucleotide base 162 shown in FIG. 1B). Additionally, these sequence reads that include the reference allele 2380 are categorized in the reference allele training data 2330 irrespective of the edge distance 2350C between the reference allele and the edge of the sequence read.

Returning to FIG. 23A, the edge filter 250 extracts features from groups of sequencing reads categorized in each of the artifact training data 2310A, non-artifact training data 2310B, and reference allele training data 2330. Each group of sequencing reads corresponds to the same position in the genome. Specifically, artifact features 2320 and non-artifact features 2325 are extracted from sequence reads in one, two, or all three of the artifact training data 2310A, non-artifact training data 2310B, and reference allele training data 2330. Examples of artifact features 2320 and non-artifact features 2325 include a statistical distance from edge feature, a significance score feature, and an allele fraction feature. Each of these features are described in further detail below in relation to FIGS. 23E-23G.

Figure 23E:
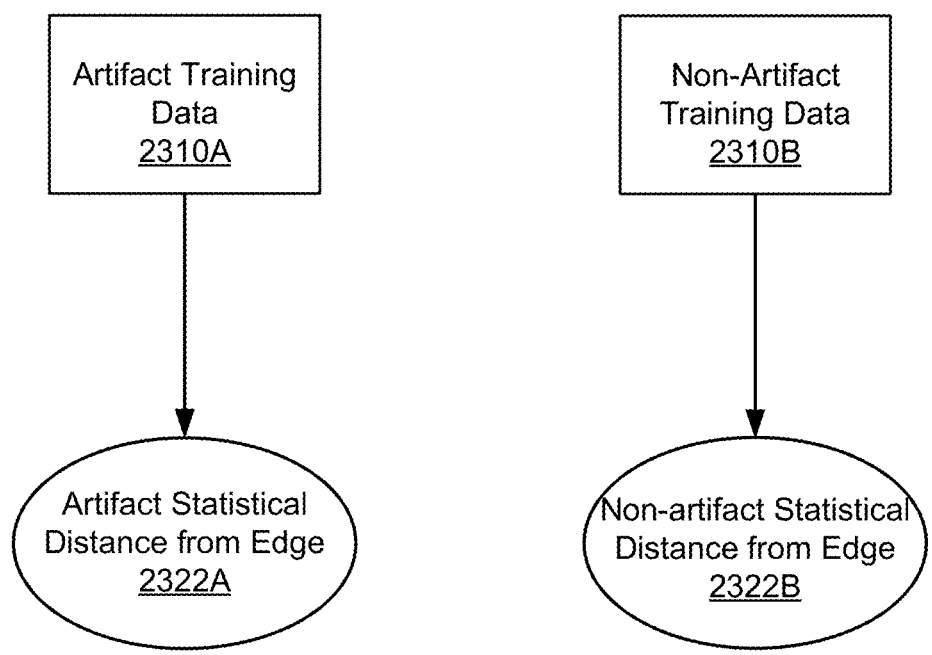
FIG. 23E is an example depiction of a process for extracting a statistical distance from edge feature according to one embodiment.

FIG. 23E is an example depiction of a process for extracting a statistical distance from edge feature according to one embodiment. Here, the edge filter 250 extracts the artifact and non-artifact statistical distance from edge 2322A and 2322B features from a group of sequence reads in the artifact training data 2310A and a group of sequence reads in the non-artifact training data 2310B, respectively. Each statistical distance from edge 2322A and 2322B feature can represent one of a mean, median, or mode of the distance (e.g., number of nucleotide base pairs) between alternative alleles 2375 on sequence reads and the corresponding edge of sequence reads. More specifically, artifact statistical distance from edge 2322A represents the combination of edge distances 2350A (see FIG. 23B) across sequence reads in a group of the artifact training data 2310A. Similarly, non-artifact statistical distance from edge 2322B represents the combination of edge distances 2350B (see FIG. 23C) across sequence reads in a group of the artifact training data 2310B.

Figure 23F:
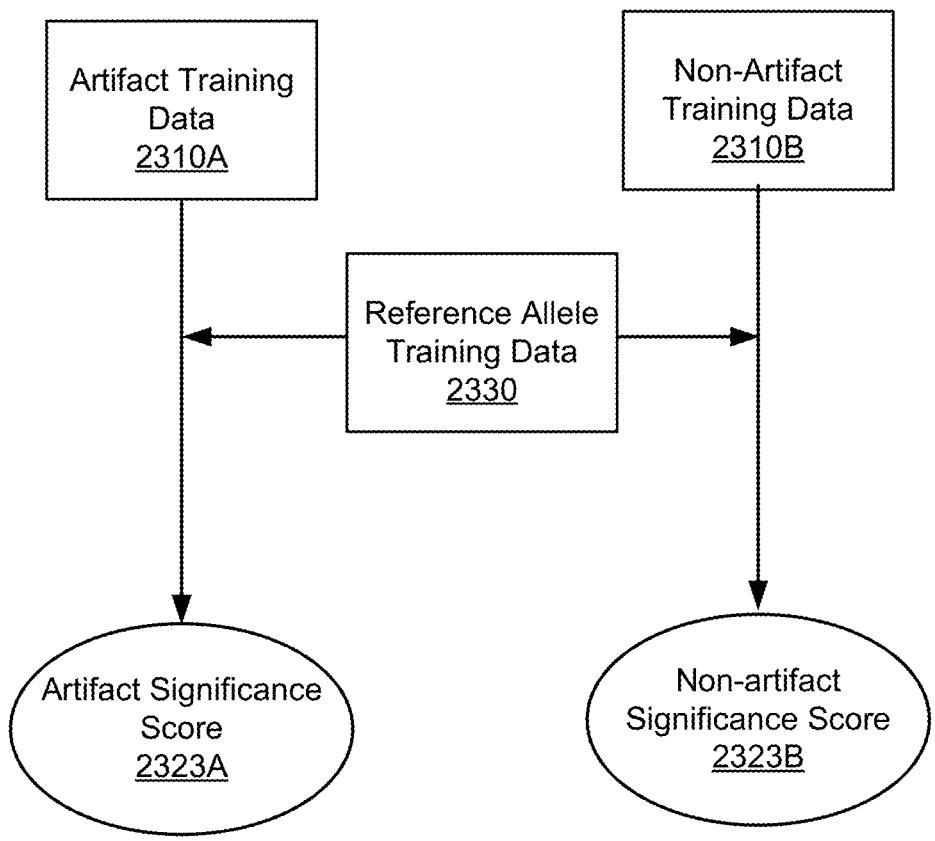
FIG. 23F is an example depiction of a process for extracting a significance score feature according to one embodiment.

FIG. 23F is an example depiction of a process for extracting a significance score feature according to one embodiment. The edge filter 250 extracts the artifact significance score 2323A feature from a combination of a group of sequence reads in the artifact training data 2310A and a group of sequence reads in the reference allele training data 2330. Similarly, the edge filter 250 extracts non-artifact significance score 2323B feature from a combination of a group of sequence reads in the non-artifact training data 2310B and a group of sequence reads in the reference allele training data 2330. Generally, the groups of sequence reads from the artifact training data 2310A, non-artifact training data 2310B, and reference allele training data 2330 correspond to a common position on the genome. Therefore, for each position, there can be an artifact significance score 2323A and a non-artifact significance score 2323B for that position. Although the subsequent description refers to the process of extracting an artifact significance score 2323A, the same description applies to the process of extracting a non-artifact significance score 2323B.

The artifact significance score 2323A feature is a representation of whether the location of alternative alleles 2375A (e.g., in terms of distance from edge of a sequence read or another measure) on a group of sequence reads in the artifact training data 2310A is sufficiently different, to a statistically significant degree, from the location of reference alleles 2380 on a group of sequencing reads in the reference allele training data 2330. Specifically, artifact significance score 2323A is a comparison between edge distances 2350A of alternative alleles 2375A (see FIG. 23B) in the artifact training data 2310A and edge distances 2350C of reference alleles 2380 (see FIG. 23D) in the reference allele training data 2330.

In various embodiments, the edge filter 250 performs a statistical significance test for the comparison between edge distances. As one example, the statistical significance test is a Wilcoxon rank-sum test. Here, the edge filter 250 assigns each sequence read in the artifact training data 2310A and each sequence read in the reference allele training data 2330 a rank depending on the magnitude of each edge distance 2350A and 2350C, respectively. For example, a sequence read that has the greatest edge distance 2350A or 2350C can be assigned the highest rank (e.g., rank=1), the sequence read that has the second greatest edge distance 2350A or 2350C can be assigned the second highest rank (e.g., rank=2), and so on. The edge filter 250 compares the median rank of sequence reads in the artifact training data 2310A to the median rank of sequence reads in the reference allele training data 2330 to determine whether the locations of alternative alleles 2375 in the artifact training data 2310A significantly differ from locations of reference alleles 2380 in the reference allele training data 2330A. As an example, the comparison between the median ranks can yield a p-value, which represents a statistical significance score as to whether the median ranks are significantly different. In various embodiments, the artifact significance score 2223A is represented by a Phred score, which can be expressed as:

$$\text{Phred Score} = -10 \log_{10} P$$

where P is the p-value score. Altogether, a low artifact significance score 2323A signifies that the difference in median ranks is not statistically significant whereas a high artifact significance score 2323A signifies that the difference in median ranks is statistically significant.

Figure 23G:
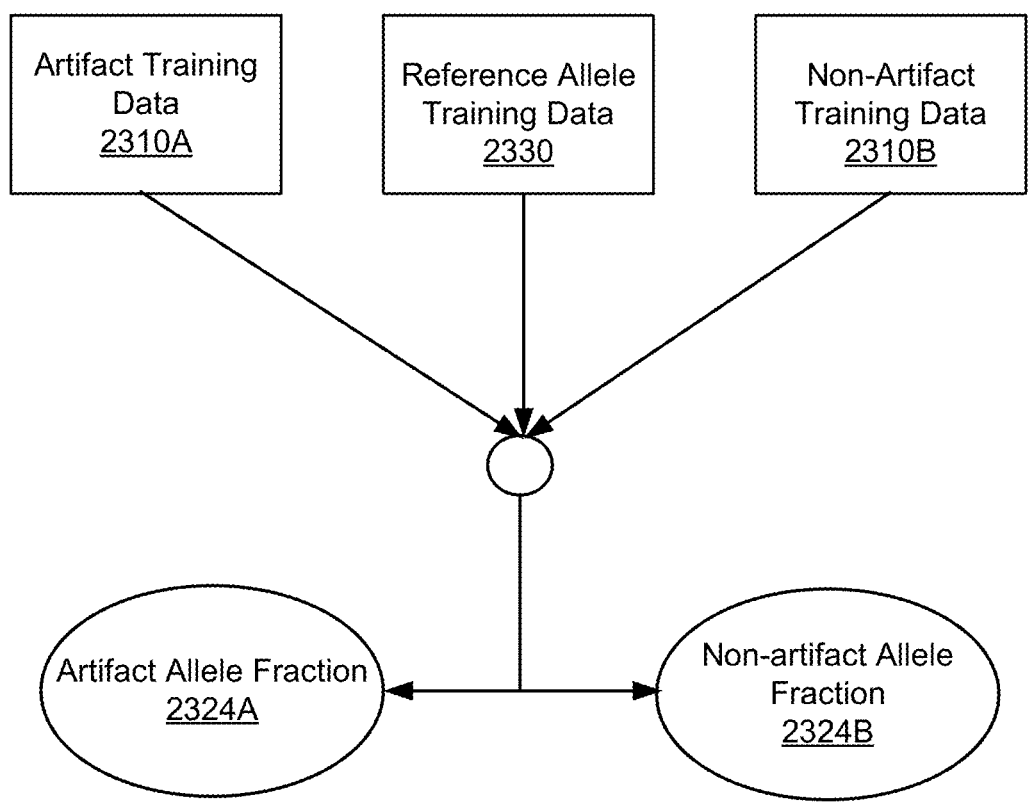
FIG. 23G is an example depiction of a process for extracting an allele fraction feature according to one embodiment.

FIG. 23G is an example depiction of a process for extracting an allele fraction feature according to one embodiment. The allele fraction feature refers to the allele fraction of alternative alleles 2375A or 2375B. Specifically, artifact allele fraction 2324A refers to the allele fraction of alternative allele 2375A (see FIG. 23B) whereas non-artifact allele fraction 2324B refers to the allele fraction of alternative allele 2375B (see FIG. 23C). The allele fraction represents the fraction of sequence reads corresponding to the position in the genome that includes the alternative allele. For example, there may be X total sequence reads in the artifact training data 2310A that include the alternative allele 2375A. There may also be Y total sequence reads in the non-artifact training data 2310B that include the alternative allele 2375B. Additionally, there may be Z total sequence reads in the reference allele training data 2330 with the reference allele. Therefore, the artifact allele fraction 2324A of the alternative allele 2375A can be denoted as $$\text{Allele Fraction (2324A)} = \frac{X}{X+Y+Z}.$$

Additionally, the non-artifact allele fraction 2324B of the alternative allele 2375B can be denoted as $$\text{Allele Fraction (2324B)} = \frac{Y}{X+Y+Z}.$$

Returning to FIG. 23A, the edge filter 250 compiles extracted artifact features 2320 from groups of sequence reads across various positions of the genome to generate an artifact distribution 2340. Additionally, the edge filter 250 compiles extracted non-artifact features 2325 from groups of sequence reads across various positions of the genome to generate a non-artifact distribution 2345. FIG. 23A depicts one particular embodiment where three different features 2320A are used to generate an artifact distribution 2340 and three different features 2320B are used to generate a non-artifact distribution 2345. In other embodiments, fewer or more of each type of feature 2320A or 2320B are used to generate an artifact distribution 2340 or non-artifact distribution 2345.

Figure 23H:
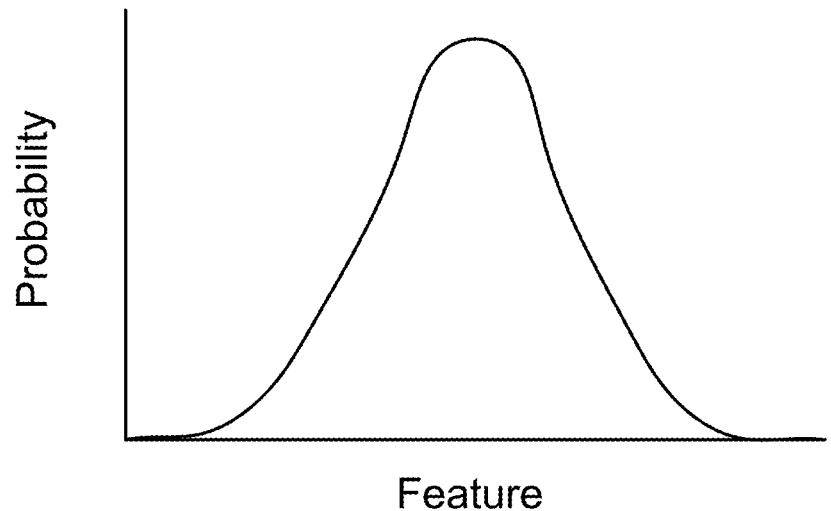
FIGS. 23H and 23I depict example distributions used for identifying edge variants according to various embodiments.
Figure 23I:
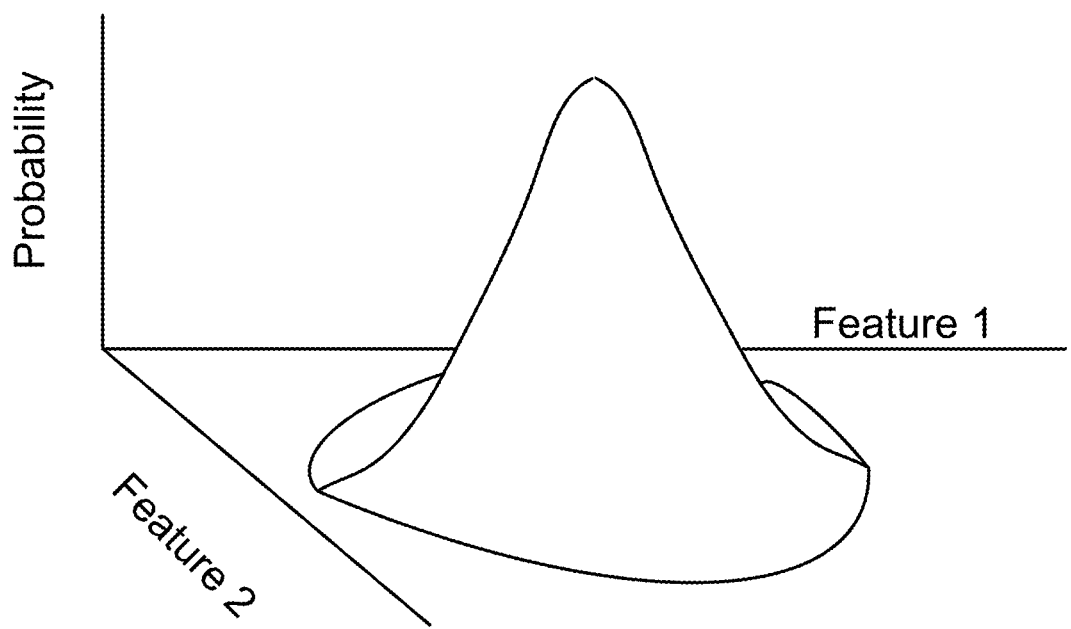

FIGS. 23H and 23I depict example distributions used for identifying edge variants, according to various embodiments. Specifically, FIG. 23H depicts a distribution 2340 or 2345 generated from one type of artifact feature 2320 or non-artifact feature 2325. Although FIG. 23G depicts a normal distribution for sake of illustration, in practice, distributions 2340 and 2345 will vary depending on the values of the feature 2320 or 2325.

In another embodiment, the edge filter 250 may use multiple artifact features 2320 or non-artifact features 2325 to generate a single distribution 2340 or 2345. For example, FIG. 23I depicts a distribution 2340 or 2345 generated from two types of artifact features 2320 or two types of non-artifact features 2325. Here, the distribution 2340 or 2345 describes a relationship between a first feature and a second feature. In further embodiments, a distribution 2340 or 2345 can represent relationships between three or more types of artifact features 2320 or non-artifact features 2325.

Figure 24A:
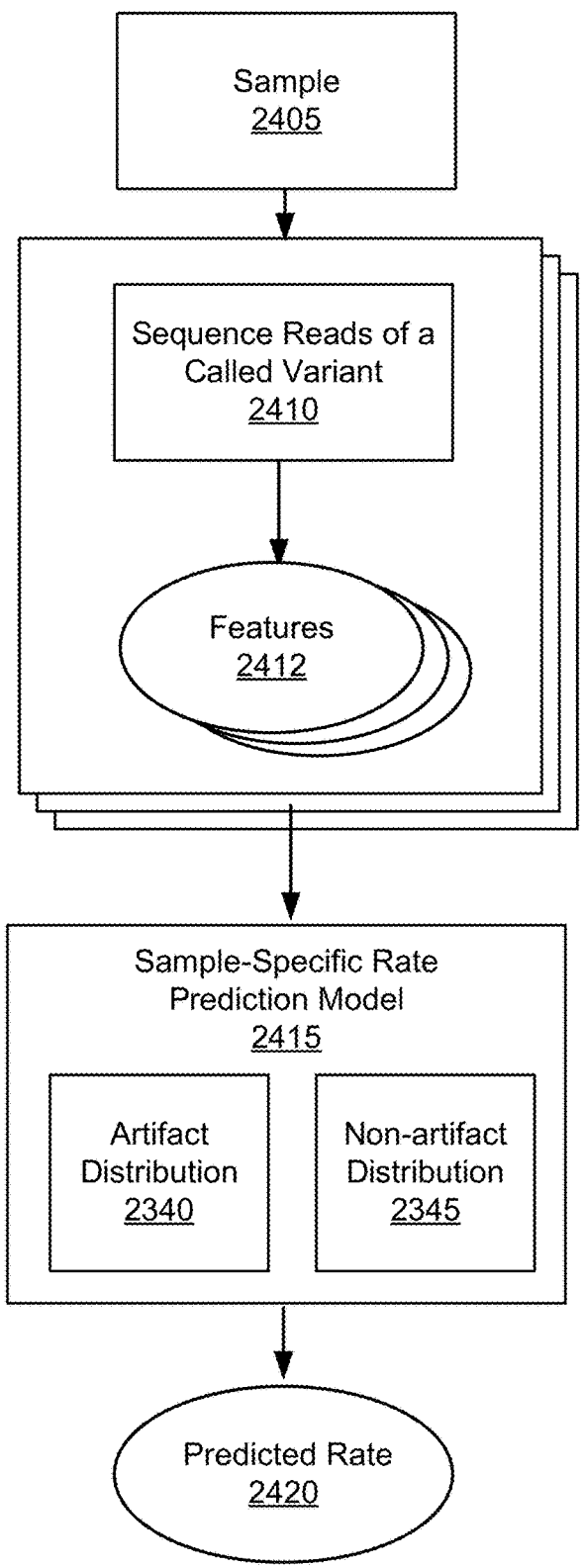
FIG. 24A depicts a block diagram flow process for determining a sample-specific predicted rate according to one embodiment.

IX. B. Example Determining of a Sample-Specific Rate for Identifying Edge Variants FIG. 24A depicts a block diagram flow process 2400 for determining a sample-specific predicted rate according to one embodiment. Generally, the edge filter 250 conducts a sample-wide analysis of called variants in the sample 2405 to determine the predicted rate 2420 that is specific for the sample 2405. In other words, the process 2400 shown in FIG. 24A can be conducted once for each sample 2405.

Sequence reads of a called variant 2410 are obtained from a sample 2405. As described above in relation to FIGS. 1A and 3, the steps for identifying called variants from a sample 2405 can include one or more steps of the method 100 or 300. Generally, the sequence reads of a called variant 2410 refer to a group of sequence reads that cross over the position in the genome to which the called variant corresponds.

For each called variant, the edge filter 250 extracts features 2412 from the sequence reads of the called variant 2410. Each feature 2412 extracted from sequence reads of a called variant 2410 can be a statistical distance from edge of alternative alleles in the sequence reads, an allele fraction of an alternative allele, a significance score, another type of feature, or some combination thereof. The edge filter 250 applies features 2412 extracted across called variants of the sample 2405 as input to a sample-specific rate prediction model 2415 (e.g., one of the models 225 shown in FIG. 2) that determines a predicted rate 2420 for the sample 2405. The predicted rate 2420 for the sample 2405 refers to an estimated proportion of called variants that are edge variants. In various embodiments, the predicted rate 2420 is a value between 0 and 1, e.g., inclusive.

As shown in FIG. 24A, the sample-specific rate prediction model 2415 uses both the previously generated artifact distribution 2340 and non-artifact distribution 2345. The sample-specific rate prediction model 2415 determines the predicted rate 2420 by analyzing the features 2412 extracted from sequence reads of called variants in the sample 2405 in view of the artifact distribution 2340 and non-artifact distribution 2345. As an example, the sample-specific rate prediction model 2415 performs a goodness of fit to determine a predicted rate 2420 that explains the observed features 2412, given the artifact distribution 2340 and non-artifact distribution 2345. In one implementation, the sample-specific rate prediction model 2415 performs a maximum likelihood estimation to estimate the predicted rate 2420 that maximizes the likelihood of observing the features 2412 in view of the artifact distribution 2340 and non-artifact distribution 2345. However, other implementations may use other processes.

In one embodiment, the likelihood equation for the estimation can be expressed as:

$$L(w|x) = w*(L(x)|d_1) + (1-w)*((L(x)|d_2)) \quad (1)$$

where w is the predicted rate 2420, x represents the features 2412, $d_1$ represents the artifact distribution 2340, and $d_2$ represents the non-artifact distribution 2345. In other words, Equation 1 is the weighted sum of a likelihood of observing the features 2412 in view of the artifact distribution 2340 and a likelihood of observing the features 2412 in view of the non-artifact distribution 2345. Therefore, the maximum likelihood estimation determines the predicted rate 2420 (e.g., rate w) that maximizes this overall likelihood given a certain set of conditions.

As shown in FIG. 24A, the edge filter 250 can extract multiple features 2412 from sequence reads of a called variant 310 and provide the features 2412 to the rate prediction model 2415. For example, there may be three types of features (e.g., statistical distance from edge of alternative alleles in the sequence reads, an allele fraction of an alternative allele, or a significance score). Generalizing further, assuming that n different types of features 2412 (e.g., $x_1, x_2, \ldots x_n$) are provided to the rate prediction model 2415, Equation 1 can be expressed as:

$$L(w|x_1, x_2 \ldots x_n) = w*(\pi_1{}^n L(x_n)|d_1) + (1-w)*(\pi_1{}^n L(x_n)|d_2) \quad (2)$$

Altogether, responsive to determining that the distribution of features 2412 extracted from sequence reads of the called variants in the sample 2405 are more similar to the artifact distribution 2340 than the non-artifact distribution 2345, the rate prediction model 2415 determines a high predicted rate 2420, which indicates that a high estimated proportion of called variants are likely edge variants. Alternatively, responsive the distribution of features 2412 extracted from sequence reads of variants in the sample 2405 are more similar to the non-artifact distribution 2345 than the artifact distribution 2340, the rate prediction model 2415 determines a low predicted rate 2420, which indicates that a low estimated proportion of called variants are likely edge variants. As discussed below, the predicted rate 2420 can be used to control for the level of "aggressiveness" in which edge variants are identified in a sample. Therefore, a sample that is assigned a high predicted rate 2420 can be aggressively filtered (e.g., using broader criteria to filter out a greater number of possible edge variants) whereas a sample that is assigned a low predicted rate 2420 can be less aggressively filtered.

IX. C. Example Variant Specific Analysis for Identifying an Edge Variant

Figure 24B:
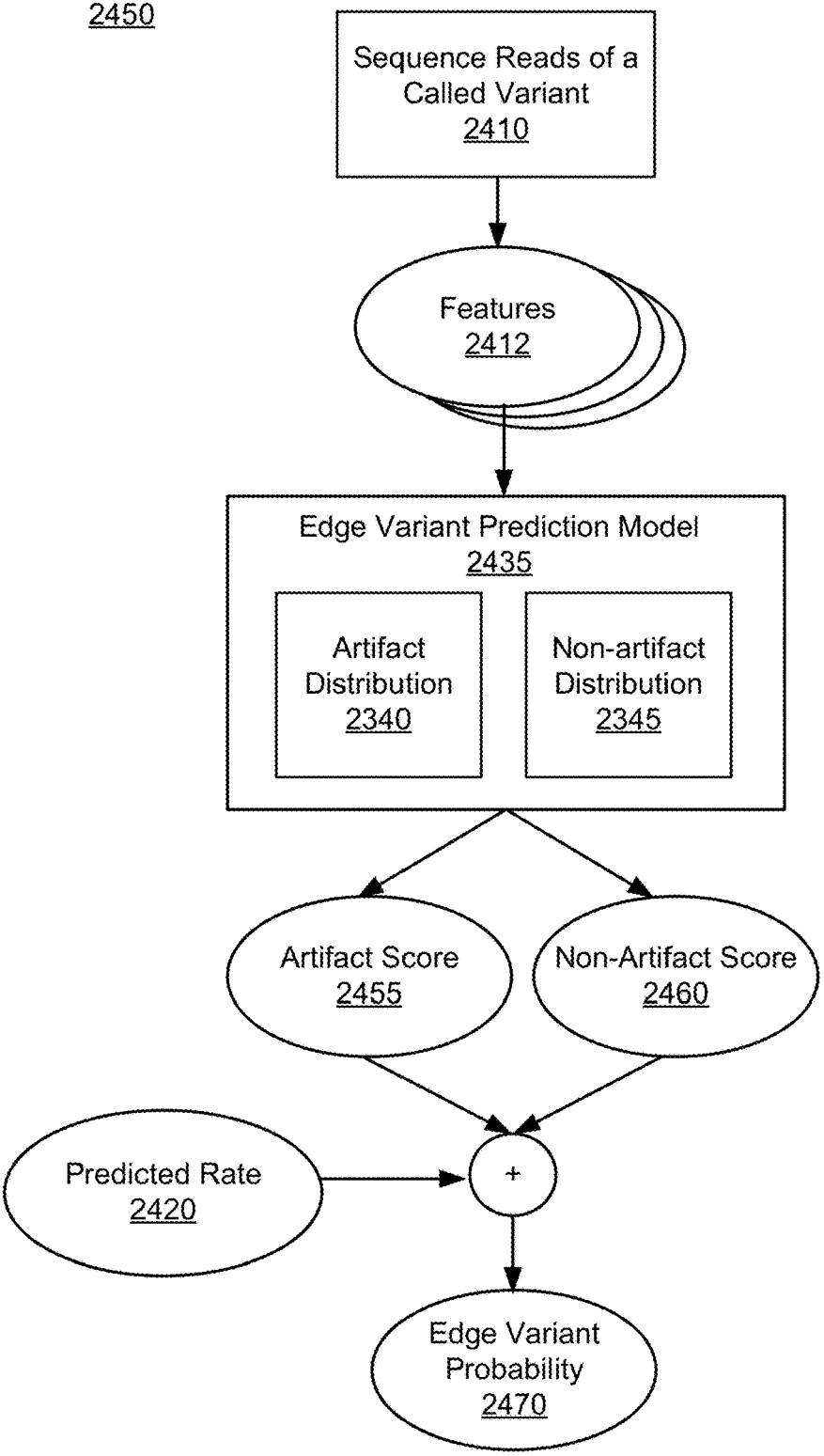
FIG. 24B depicts the application of an edge variant prediction model for identifying edge variants according to one embodiment.

FIG. 24B depicts the application of an edge variant prediction model 2435 for identifying edge variants according to one embodiment. In a variant specific analysis 2450, the edge filter 250 analyzes sequence reads of a called variant 2410 to determine whether the called variant is an edge variant. The process depicted in FIG. 24B can be conducted for each called variant or a subset of called variants that were detected for a single sample 2405.

In one embodiment, the edge filter 250 filters called variants based on a type of mutation of the called variant. Here, a called variant that is not of the C>T or G>A mutation type can be automatically characterized as a non-edge variant. Alternatively, any called variant that is of the C>T or G>A is further analyzed in the subsequent steps described hereafter.

As shown in FIG. 24B, the edge filter 250 extracts features 2412 from the sequence reads of a called variant 2410. The extracted features 2412 of the sequence reads of a called variant 2410 can be the same features 2412 extracted from the sequence reads of a called variant 2410 as shown in FIG. 24A. Namely, the features 2412 can be one or more of: a statistical distance from edge of alternative alleles in the sequence reads, an allele fraction of an alternative allele, or a significance score, among other types of features.

The edge filter 250 provides the extracted features 2412 as input to the edge variant prediction model 2435 (e.g., one of the models 225 shown in FIG. 2). As shown in FIG. 24B, the edge variant prediction model 2435 uses both the previously generated artifact distribution 2340 and the non-artifact distribution 2345. The edge variant prediction model 2435 generates multiple scores, such as an artifact score 2455 that represents a likelihood that the called variant is an edge variant as well as a non-artifact score 2460 that represents a likelihood that the called variant is a non-edge variant.

Specifically, the edge variant prediction model 2435 determines the probability of observing the features 2412 of the sequence reads of a called variant 2410 in view of the artifact distribution 2340 and the non-artifact distribution 2345. In one embodiment, the edge variant prediction model 2435 determines the artifact score 2455 by analyzing the features 2412 in view of the artifact distribution 2340 and determines the non-artifact score 2460 by analyzing the features 2412 in view of the non-artifact distribution 2345.

As a visual example, referring back to the example distribution shown in FIG. 23H, the edge variant prediction model 2435 identifies a probability based on where along the x-axis a feature 2412 falls. In this example, the identified probability can be the score, such as the artifact score 2455 or non-artifact score 2460, outputted by the edge variant prediction model 2435.

As shown in FIG. 24B, the edge filter 250 combines the artifact score 2455 and non-artifact score 2460 with the sample-specific predicted rate 2420 (as described in FIG. 24A). The combination yields the edge variant probability 2470, which represents the likelihood that the called variant is a result of a processing artifact.

In one embodiment, edge variant probability 2470 can be expressed as the posterior probability of the called variant being an edge variant in view of the features 2412 extracted from sequence reads of the called variant 2410. The combination of the artifact score 2455, the non-artifact score 2460, and the sample-specific predicted rate 2420 can be expressed as:

$$\text{Edge Variant Probability} = \frac{w * \text{artifact score}}{(w * \text{artifact score}) + (1 - w) * (\text{nonartifact score})} \quad (3)$$

The edge filter 250 may compare the edge variant probability 2470 against a threshold value. Responsive to determining that the edge variant probability 2470 is greater than the threshold value, the edge filter 250 determines that the called variant is an edge variant. Responsive to determining that the edge variant probability 2470 is less than the threshold value, the edge filter 250 determines that the called variant is a non-edge variant.

IX. D. Example Variant Specific Analysis for Identifying an Edge Variant

Figure 25:
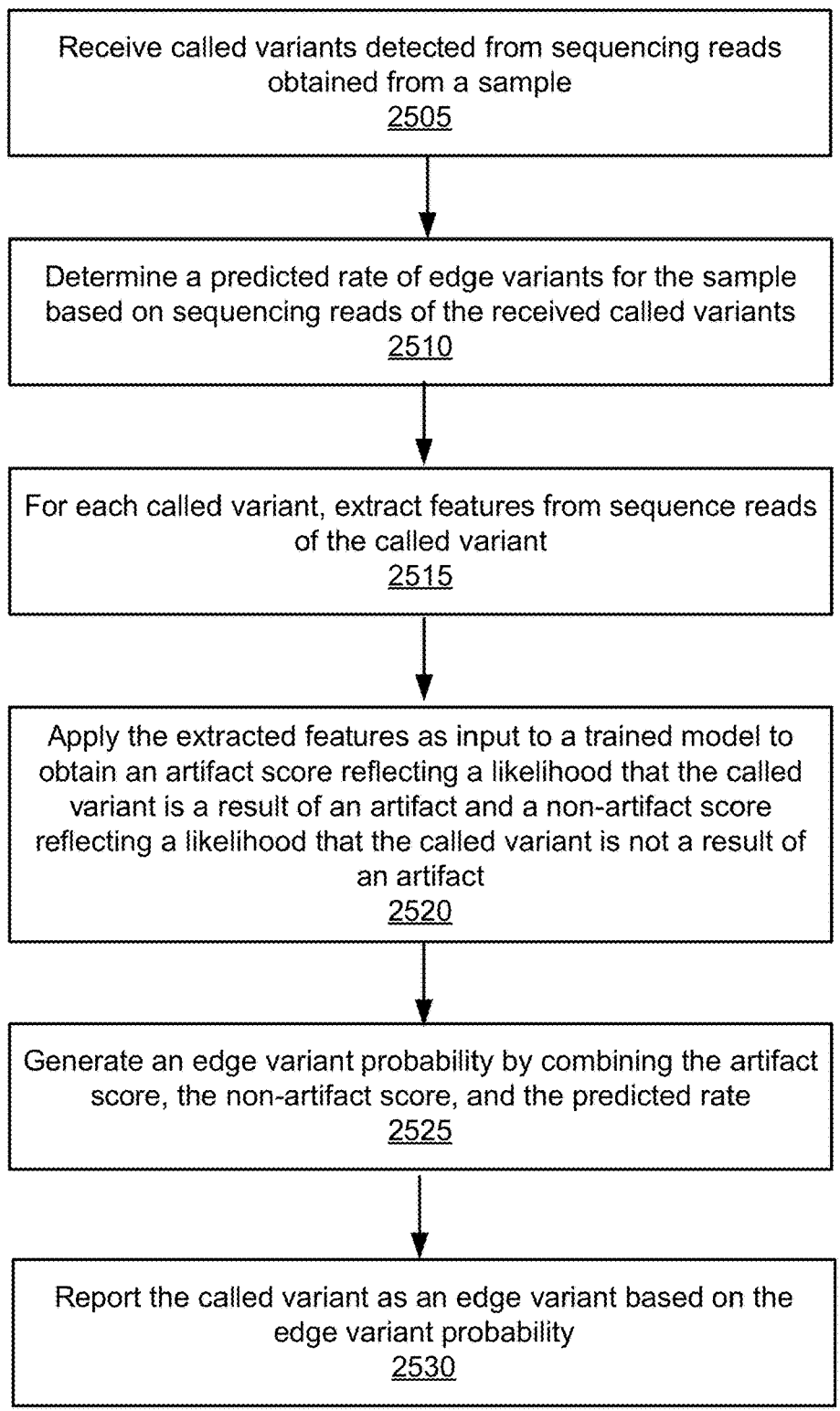
FIG. 25 depicts a flow process of identifying and reporting edge variants detected from a sample according to one embodiment.

FIG. 25 depicts a flow process 2500 of identifying and reporting edge variants detected from a sample according to one embodiment. One or more steps of the process 2500 may be performed by components of the processing system 200, e.g., the edge filter 250 or one of the models 225. Called variants from various sequencing reads are received 2505 from a sample. A sample-specific predicted rate is determined 2510 for the sample based on sequencing reads of the called variants from the sample. As one example, a predicted rate is determined by performing a maximum likelihood estimation. Here, the predicted rate is a parameter value that maximizes (e.g., given certain conditions) the likelihood of observing features 2412 of sequence reads of the called variants in view of previously generated distributions.

For each called variant, one or more features 2412 are extracted 2515 from the sequence reads of the variant. The extracted features 2412 are applied 2520 as input to a trained model 225 to obtain an artifact score 2455. The artifact score 2455 represents a likelihood that the called variant is an edge variant (e.g., result of a processing artifact). The trained model 225 further outputs a non-artifact score 2460 which represents a likelihood that the called variant is a non-edge variant (e.g., not a result of a processing artifact).

For each called variant, an edge variant probability 2470 is generated 2525 by combining the artifact score 2455 for the called variant, non-artifact score 2460 for the called variant, and the sample-specific predicted rate 2420. Based on the edge variant probability 2470, the called variant can be reported 2530 as an edge variant (e.g., variants that were called as a result of a processing artifact).

IX. E. Examples of Edge Filtering

The following examples are put forth so as to provide those of ordinary skill in the art with a complete disclosure and description of how to make and use the disclosed embodiments, and are not intended to limit the scope of what is regarded as the invention. Efforts have been made to ensure accuracy with respect to the numbers used (e.g. amounts, temperature, concentrations, etc.) but some experimental errors and deviations should be allowed for. It will be appreciated by those of skill in the art that, in light of the present disclosure, numerous modifications and changes can be made in the particular embodiments exemplified without departing from the intended scope of the invention.

IX. E. I. Categorizing Artifact and Clean Training Samples

Figure 26A:
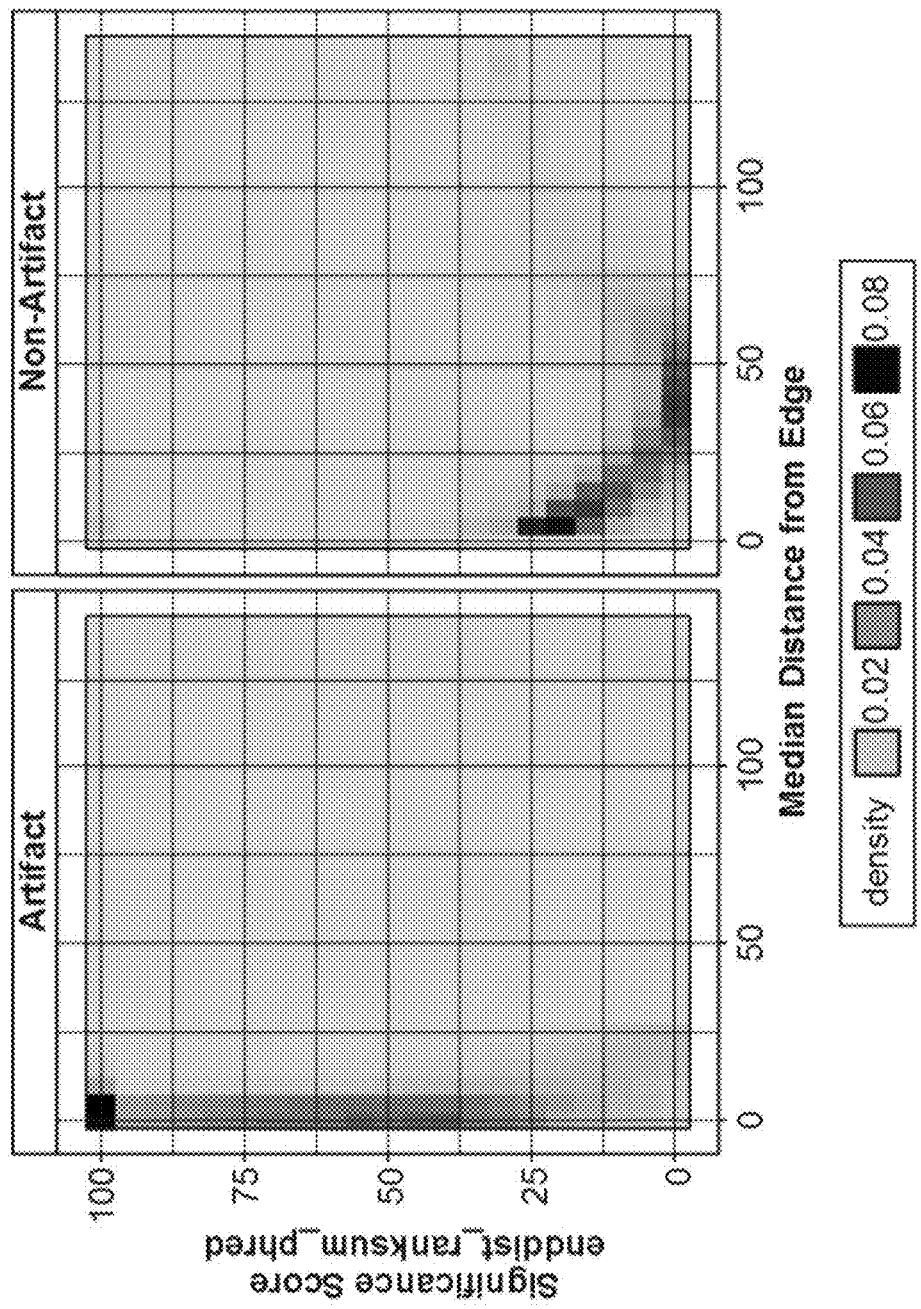
FIGS. 26A, 26B, and 26C each depict the features of example training variants that are categorized in one of the artifact or non-artifact categories according to various embodiments.
Figure 26B:
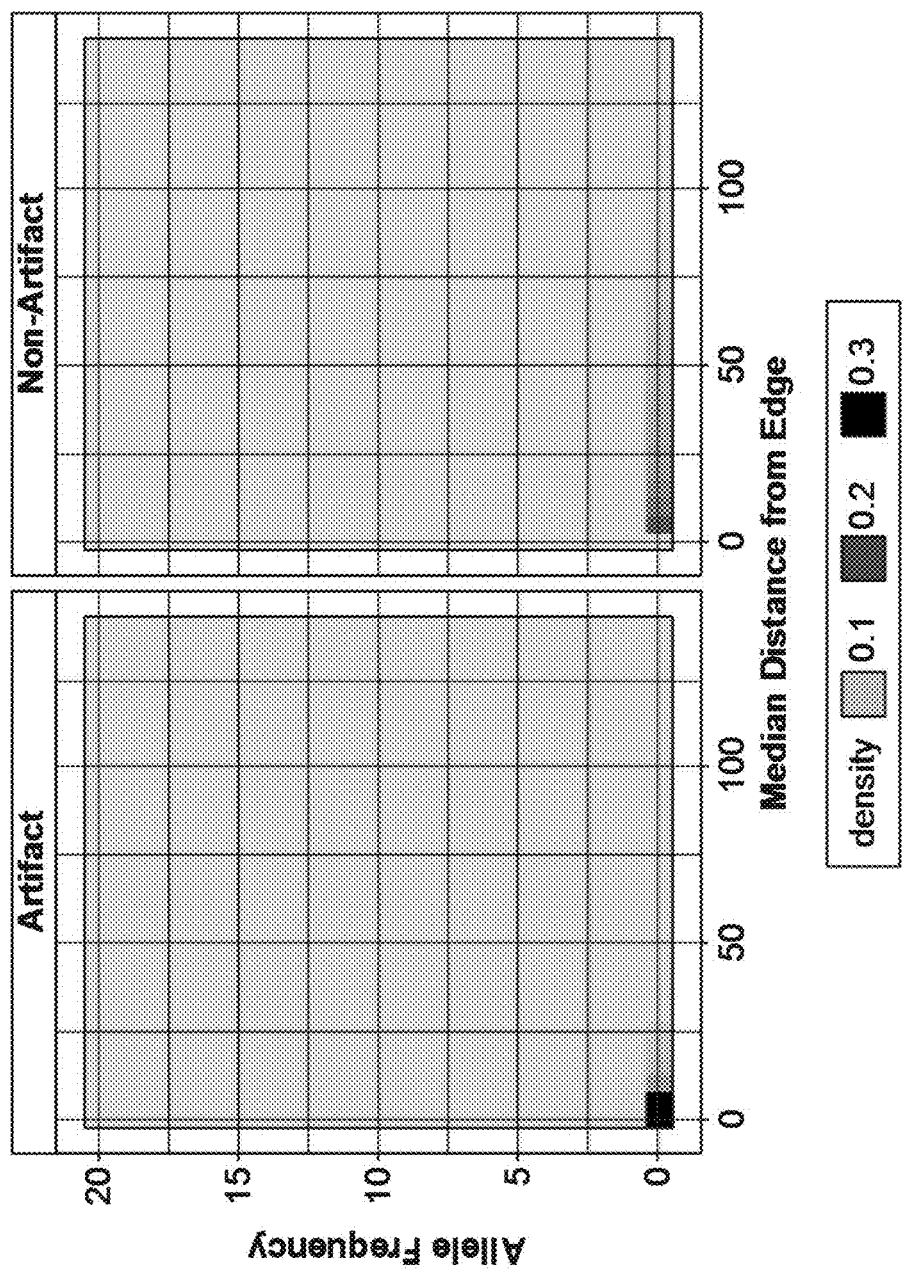
Figure 26C:
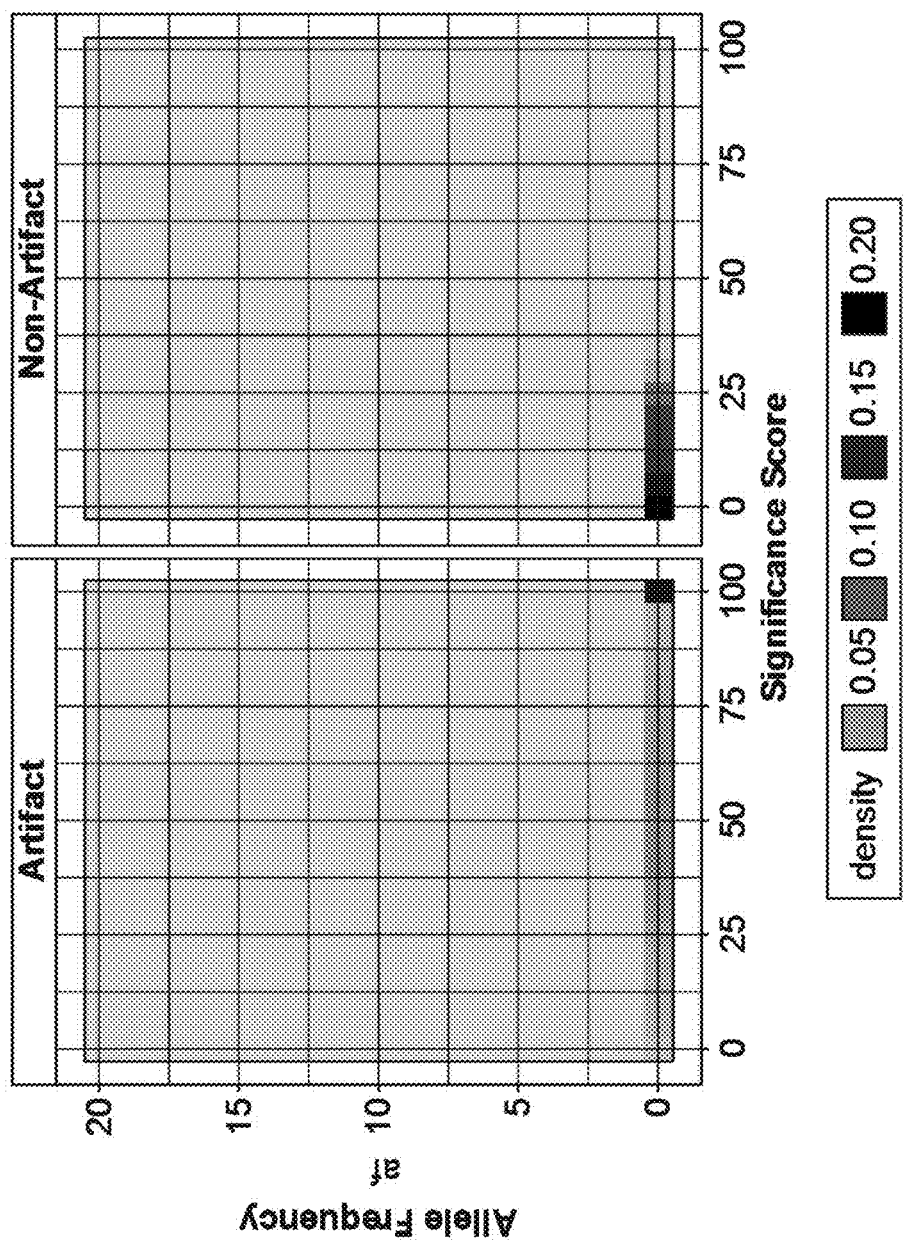

FIGS. 26A, 26B, and 26C each depict the features of example training variants that are categorized in one of the artifact or non-artifact categories according to various embodiments. The examples shown in FIGS. 26A, 26B, and 26C include artifact distributions and non-artifact distributions determined using the process 2300 shown in FIG. 23A.

Cell free DNA samples were obtained from subjects with one of breast cancer, lung cancer, or prostate cancer through a blood draw. The sample set includes at least 50 subjects for each type of cancer (breast, lung, and prostate cancer). For all participating subjects, blood was drawn contemporaneously within six weeks of (prior to or after) biopsy.

The cfDNA samples were analyzed for variants according to one or more steps of the process workflow shown in FIG. 1A and/or FIG. 3 to obtain filtered called variants following step 130. For each of the called variants, the sequence reads that led to the identification of the called variant are analyzed. For example, the edge filter 250 categorizes sequence reads that include an alternative allele for a particular site on the genome into artifact and non-artifact groups, as is described below. Additionally, the sequence reads that include the reference allele for the particular site on the genome are included as reference allele data to be later used to determine features of the sequence reads.

The edge filter 250 categorizes sequence reads that include the alternative allele into the artifact or non-artifact category based on two criteria. A first criteria includes a threshold distance of 25 nucleotide base pairs. Therefore, sequence reads categorized in the artifact category include an alternative allele that is within 25 nucleotide base pairs from the edge of the sequence read. A second criteria is a type of nucleotide base mutation. Specifically, sequence reads categorized into the artifact category include an alternative allele that is one of a C>T or G>A mutation. The edge filter 250 categorizes sequence reads that include an alternative allele that does not satisfy these two criteria into the non-artifact category.

The edge filter 250 extracts features from sequence reads of a called variant, including sequence reads that include an alternative allele as well as sequence reads that include the reference allele. Here, the three types of features extracted include: 1) median distance of alternative alleles from the edge of the sequence read, 2) allele fraction of the alternative allele, and 3) significance score. The three types of extracted features are compiled and used to generate the artifact distributions and non-artifact distributions shown in FIGS. 26A-C.

FIGS. 26A-C each show an artifact distribution (left) and non-artifact distribution (right). Each distribution depicts a relationship between two features extracted from sequencing reads that are categorized as artifact training data or non-artifact training data. Specifically, FIG. 26A depicts a relationship between the significance score and median distance from edge. FIG. 26B depicts a relationship between the distribution of the allele fraction and median distance from edge. FIG. 26C depicts a relationship between the distribution of the allele fraction and significance score.

Several trends are observed across the artifact distributions and non-artifact distributions shown in FIGS. 26A-C. Notably, edge variants in the artifact category tend to have high significance scores (e.g., high concentration of edge variants at a significance score of 100 as shown in FIG. 26A and FIG. 26C) whereas non-edge variants in the non-artifact category tend to have far lower significance scores. Additionally, a lower median distance from the edge is correlated with a higher concentration of edge variants. For example, both FIG. 26A and FIG. 26B depict a higher concentration of edge variants with an alternative allele at or near a median distance of zero nucleotide bases from an edge as opposed to a median distance of 25 nucleotide bases from an edge. Of note, a large number of non-edge variants also include an alternative allele that is within 25 nucleotide bases from the edge of a sequencing read (see FIG. 26A and FIG. 26B).

This indicates that there is a population of non C>T and non G>A nucleotide base substitutions that are identified as called variants.

IX. E. II. Detecting Edge Variants in Human MSK-VP-0058

Figure 27A:
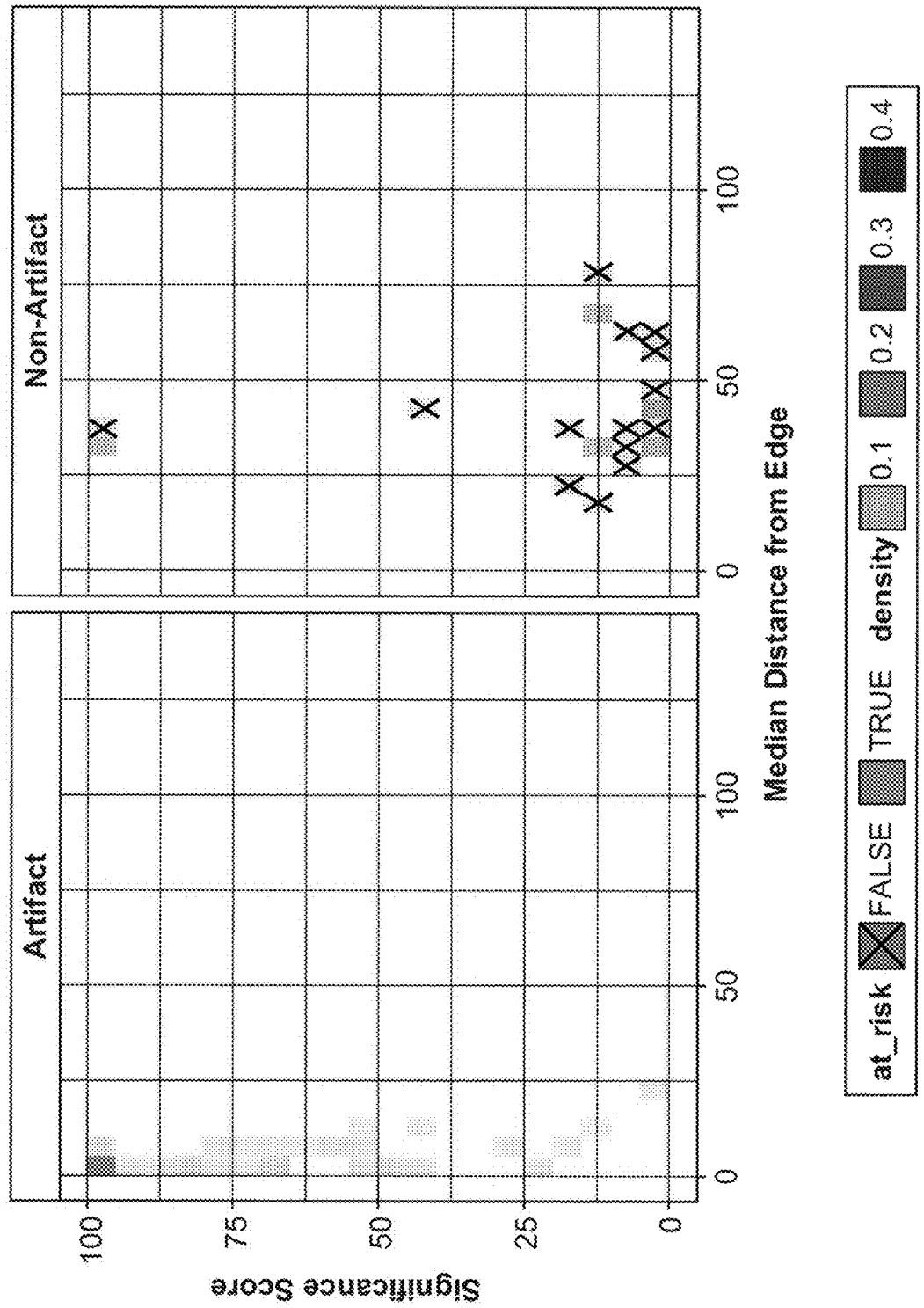
FIGS. 27A, 27B, and 27C each depict the detection of edge and non-edge variants in an example cancer sample obtained from a subject according to various embodiments.
Figure 27B:
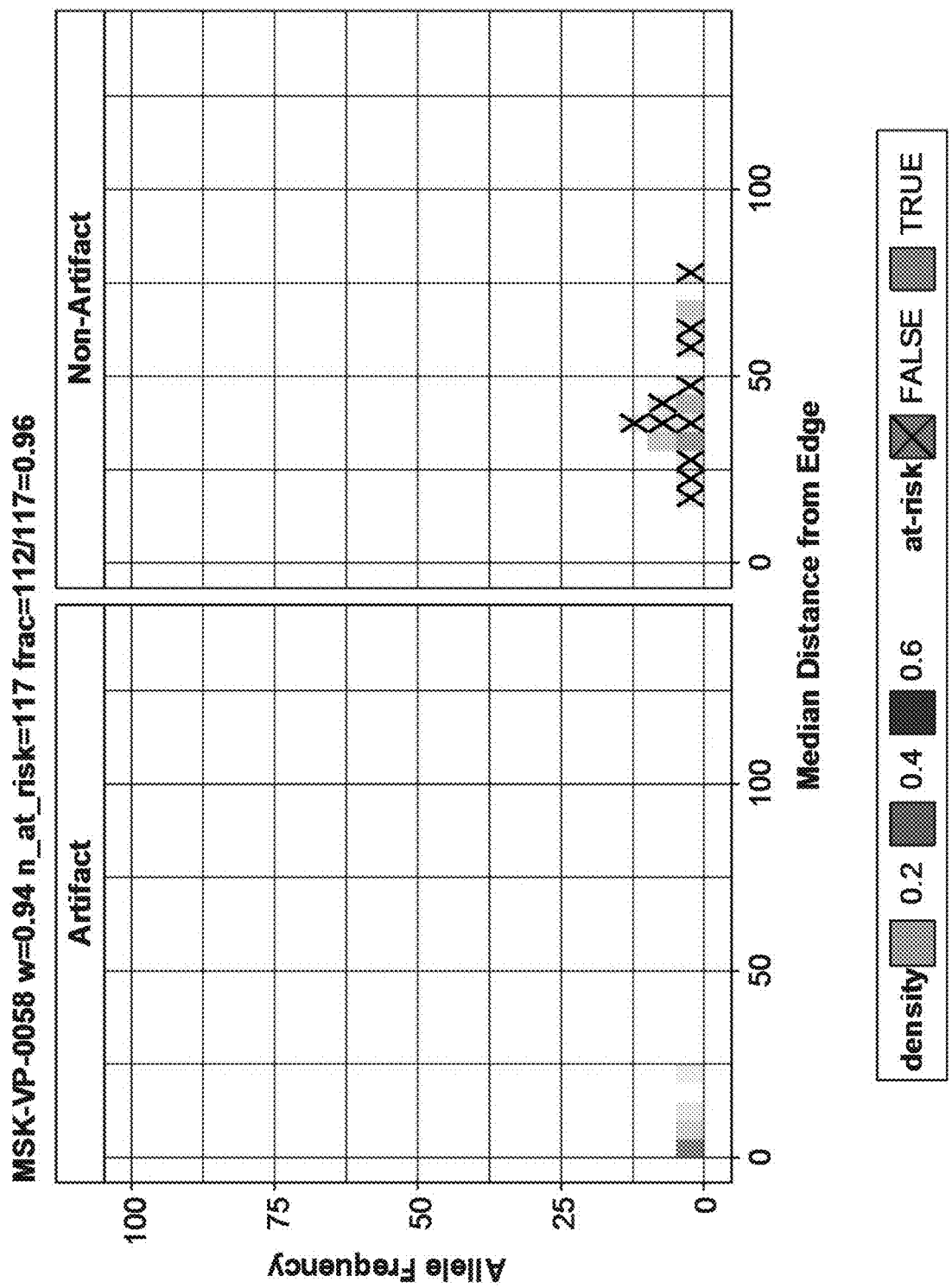
Figure 27C:
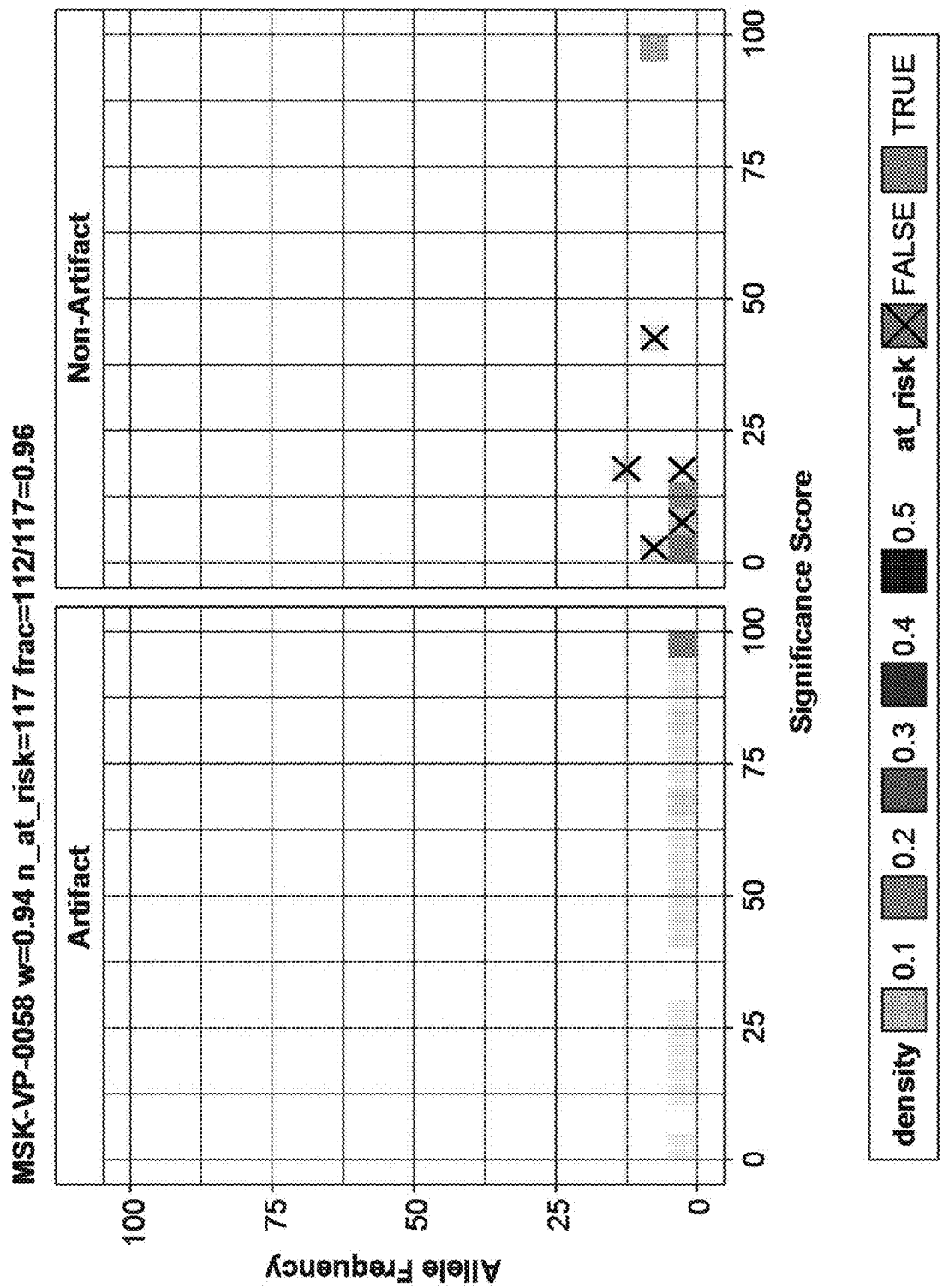

FIGS. 27A, 27B, and 27C each depict the detection of edge and non-edge variants in an example cancer sample obtained from a subject according to various embodiments. A sample (MSK-VP-0058) was processed as described above in relation to the example shown in FIGS. 26A-C. Briefly, a cfDNA sample from the subject was analyzed for variants according to one or more steps of the process workflow shown in FIG. 1A and/or FIG. 3. Sequence reads were obtained from the cfDNA sample and categorized by the edge filter 250 into groups such that sequence reads in a group each cross a common position in the genome. The edge filter 250 extracted features from groups of sequence reads.

A sample specific analysis was conducted using the observed features extracted from the sequence reads of the sample to determine a predicted rate for the sample. Specifically, the features extracted from groups of sequence reads across all called variants (e.g., all 117 called variants detected in the sample) were analyzed in view of the artifact distribution and non-artifact distribution shown in FIGS. 26A-C. A maximum likelihood estimation was performed using Equation (1), which identified a predicted rate of w=0.94. Here, as the value of the predicted rate is high (e.g., close to 1 on a scale from 0 to 1), and therefore, the edge filter 250 aggressively filters this sample filtered to remove edge variants.

To identify edge variants, each called variant was individually analyzed. The edge filter 250 automatically categorized called variants that were non C>T and non G>A nucleotide base mutations as non-edge variants. As shown in FIGS. 27A-C, these are non-edge variants labeled as "FALSE" (e.g., called variants that are depicted with an "X"). Called variants that were either C>T or G>A nucleotide base mutations were further analyzed. For each called variant, the edge filter 250 extracted features from sequence reads of the called variant. The edge filter 250 applied the extracted features as input to an edge variant prediction model that analyzes the features in view of the artifact distribution and non-artifact distribution. The model outputs an artifact score and a non-artifact score that represent the likelihood that the called variant is an edge variant and non-edge variant, respectively. The edge filter 250 calculates the edge variant probability of the called variant according to Equation (3) which uses the artifact score, non-artifact score, and the sample-specific predicted rate of w=0.94. The edge filter 250 compares the edge variant probability of each called variant to a threshold probability of 1%.

The edge filter 250 categorized called variants having an edge variant probability greater than 1% as edge variants (e.g., left panel shown in FIGS. 27A-C). The edge filter 250 categorized called variants having an edge variant probability less than 1% as non-edge variants (e.g., right panel shown in FIGS. 27A-C). Generally, called variants categorized as edge variants exhibited high significance scores (see FIG. 27A and FIG. 27C), low median distance from edge (see FIG. 27A and FIG. 27B), and low allele frequencies (see FIGS. 27B and 27C).

IX. E. III. Detecting Edge Variants in Human MSK-VB-0023

Figure 28A:
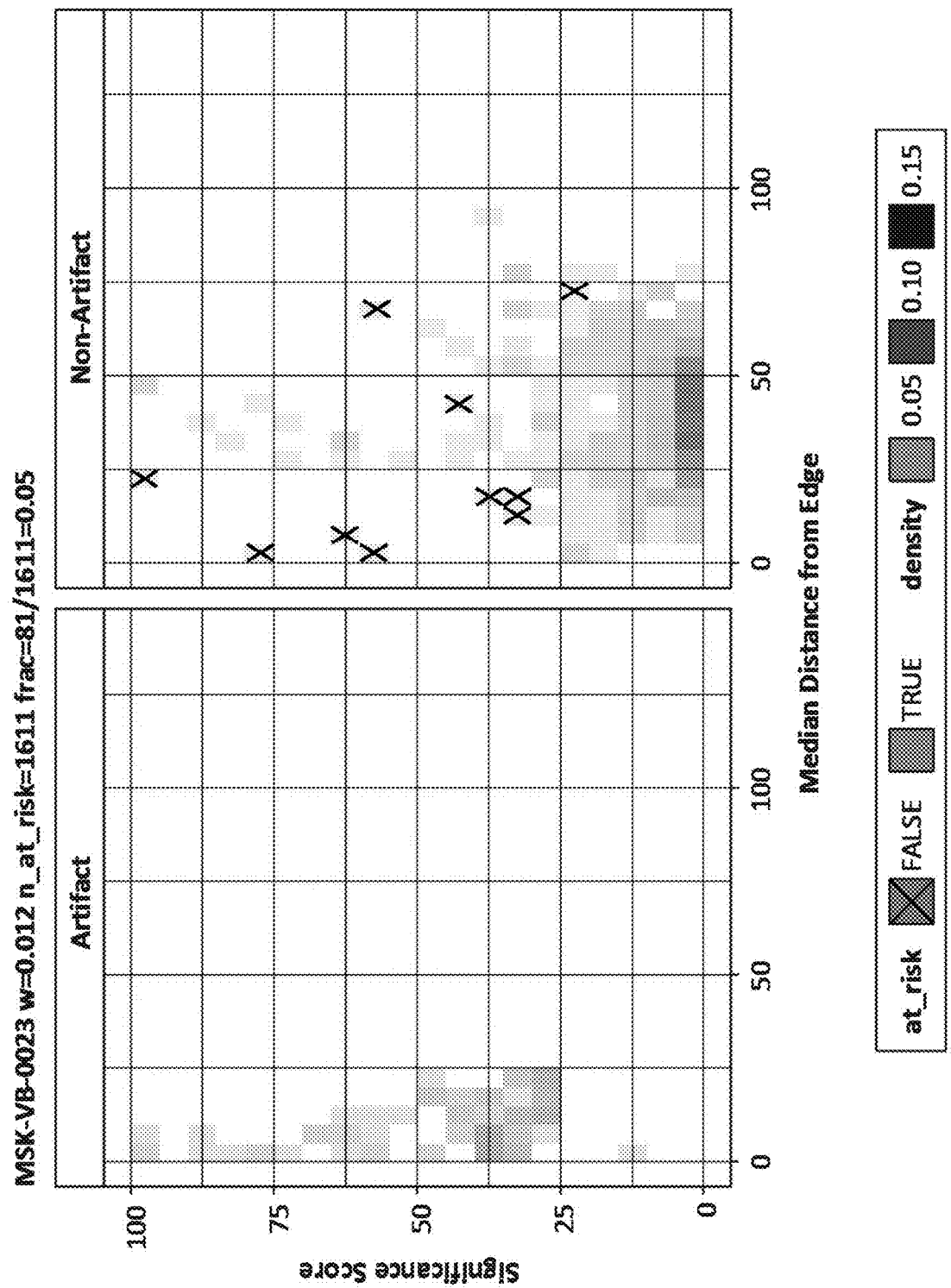
FIGS. 28A, 28B, and 28C each depict the detection of edge and non-edge variants in another example cancer sample obtained from a subject according to various embodiments.
Figure 28B:
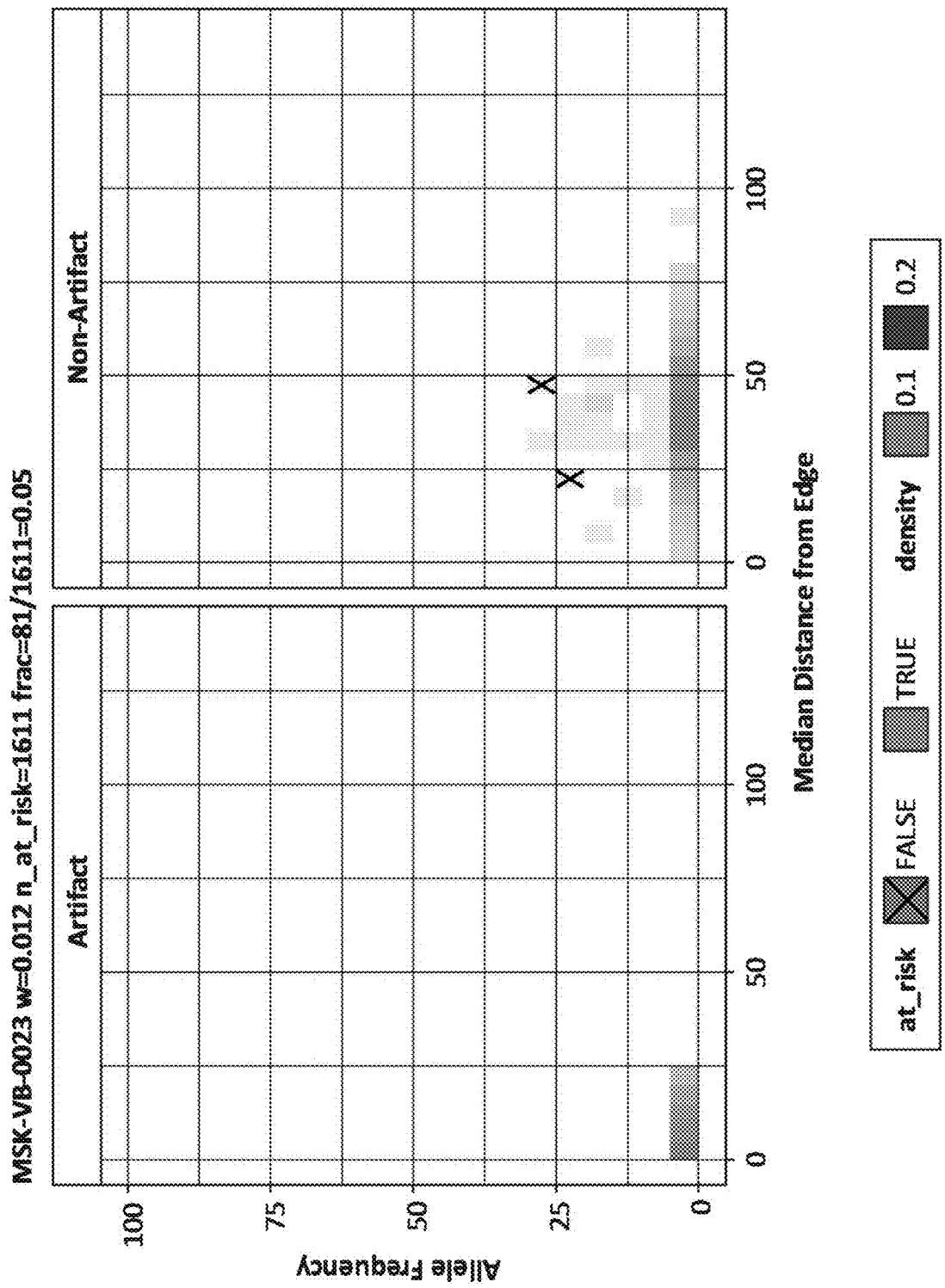
Figure 28C:
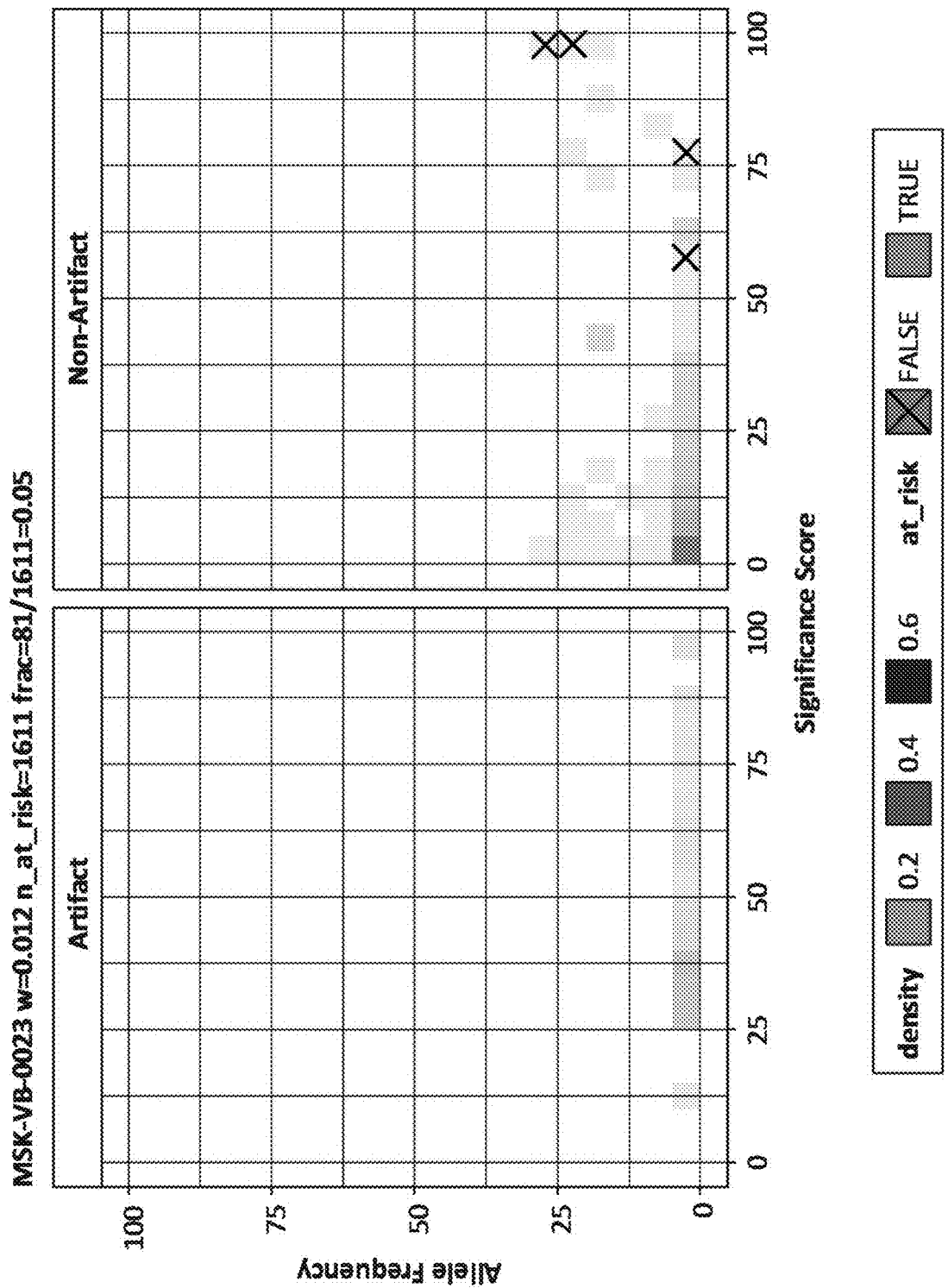

FIGS. 28A, 28B, and 28C each depict the detection of edge and non-edge variants in another example cancer sample obtained from a subject according to various embodiments. A sample (MSK-VB-0023) was processed as described above in relation to the examples shown in FIGS. 26A-C and FIGS. 27A-C.

In this example, a sample specific analysis was conducted to determine a predicted rate for the sample. Specifically, the features extracted by the edge filter 250 from sequence reads of called variants called from the sample (e.g., all 1611 called variants detected in the sample) were analyzed in view of the artifact distribution and non-artifact distribution shown in FIGS. 26A-C. The edge filter 250 performed a maximum likelihood estimation using Equation (1), which resulted in a predicted rate of w=0.012. Here, a low predicted rate value indicates the likelihood that a large number of the called variants detected in the sample are unlike previously observed edge variants. Thus, the low predicted rate is used by the edge filter 250 to perform a less aggressive filtering of edge variants.

Each called variant was analyzed to determine whether the called variant was an edge variant or a non-edge variant. The edge filter 250 automatically categorized called variants that were non C>T and non G>A nucleotide base mutations as non-edge variants. These non-edge variants are shown in FIG. 28A-C and labeled as "FALSE" (e.g., called variants that are depicted with an "X"). Called variants that were either C>T or G>A nucleotide base mutations were further analyzed. For each called variant, the edge filter 250 extracted features from sequence reads of the called variant. The edge filter 250 applied the extracted features as input to an edge variant prediction model that analyzes the features in view of the artifact distribution and non-artifact distribution. The model outputs an artifact score and a non-artifact score that represent the likelihood that the called variant is an edge variant and non-edge variant, respectively. The edge filter 250 calculates an edge variant probability of the called variant calculated according to Equation (3), which uses the artifact score, non-artifact score, and the sample-specific predicted rate of w=0.012. The edge filter 250 compares the edge variant probability of each called variant to a threshold probability of 1%.

The edge filter 250 categorized called variants having an edge variant probability greater than 1% as edge variants (e.g., left panel shown in FIGS. 28A-C). The edge filter 250 categorized called variants having an edge variant probability less than 1% as non-edge variants (e.g., right panel shown in FIGS. 28A-C).

In this example, the edge filter 250 determines a large number of called variants to be non-edge variants. Further investigation revealed that this subject exhibited hypermutator characteristics. Specifically, the subject exhibited apolipoprotein B mRNA editing catalytic polypeptide family of enzyme (APOBEC) mutational signature, which manifested as a large number of C>T mutations. Therefore, given that these called variants are not edge variants, the edge filter 250 categorized these called variants as non-edge variants.

This example demonstrates the ability of the edge filter 250 to adapt filtering processes based on the distribution of observed variants in a particular sample. As a large number of these variants likely arise due to the fact that the subject likely includes a hypermutator, the filtering process performed by the edge filter 250 can be less aggressive in identifying and removing edge variants.

IX. E. IV. Sample Specific Adaptation for Detecting Edge Variants

Figure 29:
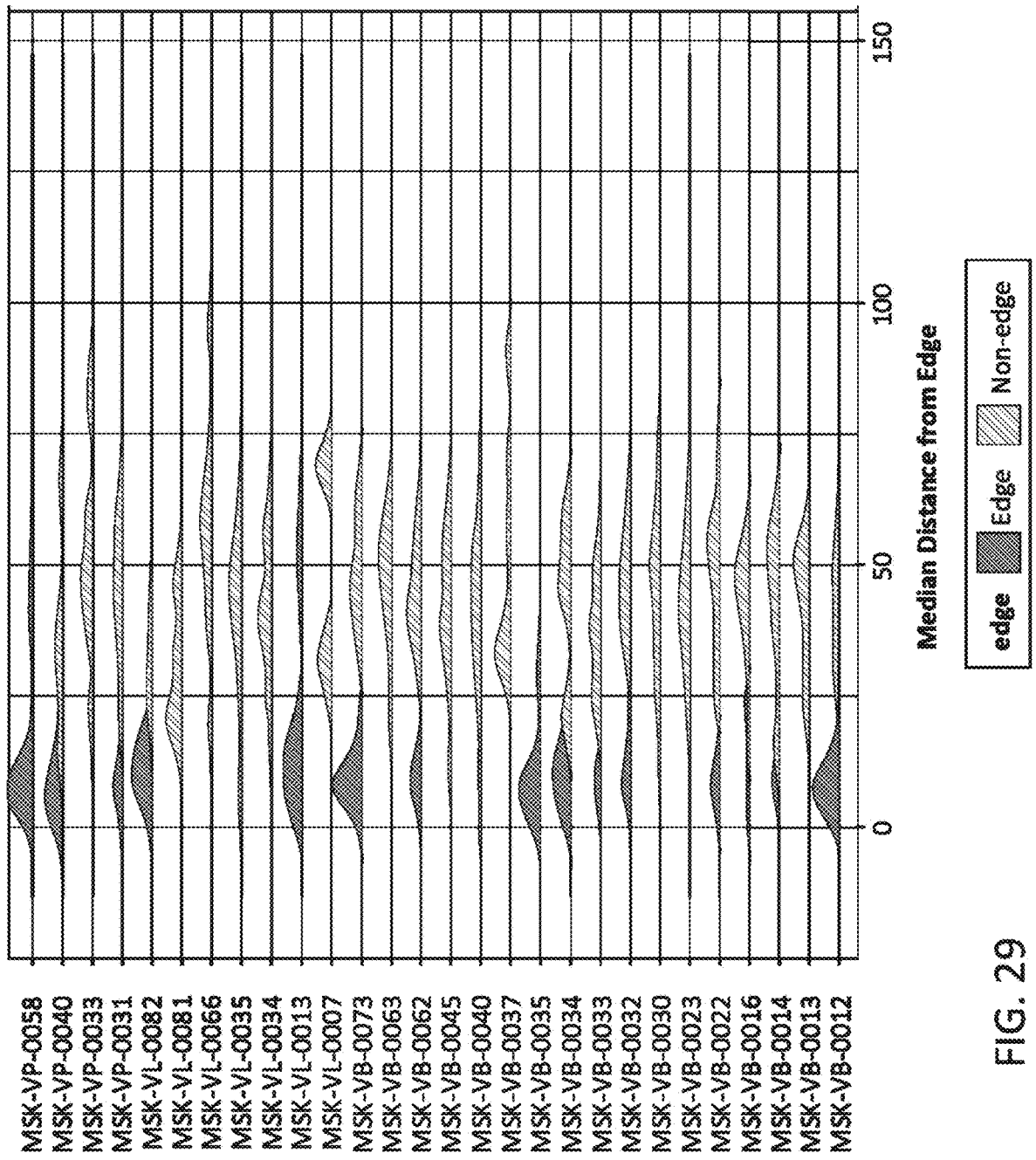
FIG. 29 depicts the identification of edge variants across various subject samples according to one embodiment.

FIG. 29 depicts the identification of edge variants across various subject samples according to one embodiment. FIG.

29 includes data from subject samples MSK-VP-0058 and MSK-VB-0023 described above with reference to FIGS. 26A-C and FIGS. 27A-C as well as many other subject samples. The example results shown in FIG. 29 may be determined using one or more steps of the workflow process shown in FIG. 1A or FIG. 3. For example, the edge variants and non-edge variants of each sample that were determined at step 320 of the process 300 were used to generate the results shown in FIG. 29.

Specifically, FIG. 29 depicts distributions of identified edge variants and non-edge variants of subject samples (the y-axis) as a function of the median distance from the edge of sequencing reads (the x-axis).

FIG. 29 demonstrates that for each subject sample, the filtering method of the edge filter 250 can differently identify edge variants and non-edge variants. For example, MSK-VP-0082 (e.g., the fifth sample from the top) includes a large number of edge variants that exhibit a median distance from the edge between 10 and 25 nucleotide base pairs. In addition, MSK-VP-VL-0081 (e.g., the sixth sample from the top) includes a significant number of non-edge variants that exhibit a median distance from the edge between 10 and 25 nucleotide base pairs. This sample-specific filtering enables more accurate identification and removal of edge variants in comparison to filters that employ the same filtering method across all samples. Examples of non-sample specific filters can employ a fixed cutoff based on a feature such as allele frequency such that if the allele frequency of an alternative allele is greater than a fixed threshold amount, then the called variant corresponding to the alternative allele is categorized as an edge variant.

IX. E. V. Sensitivity and Specificity of Edge Variant Filtering Method

FIG. 30 depicts concordant variants called in both solid tumor and in cfDNA following the removal of edge variants using different edge filters as a fraction of the variants called in cfDNA according to one embodiment. FIG. 31 depicts concordant variants called in both solid tumor and in cfDNA following the removal of edge variants using different edge filters as a fraction of the variants called in solid tumor according to one embodiment. In particular, both FIG. 30 and FIG. 31 depict concordance numbers that vary depending on the edge variant filter that is applied (e.g., no edge variant filter, simple edge variant filter, or sample-specific edge variant filter).

For the datasets shown in FIG. 30 and FIG. 31, samples were obtained from subjects and processed using the assay process described above with reference to the examples of FIGS. 26A-C to obtain an initial set of called variants following step 320 in FIG. 3. These called variants included in the initial set have not undergone further filtering to remove edge variants.

In two separate scenarios, these called variants in the initial set were further filtered by the edge filter 250 to identify and remove edge variants. A first scenario included the application of a first filter, hereafter referred to as a simple edge variant filter. The simple edge variant filter removes called variants that exhibit a median distance from edges of sequence reads that fall below a threshold distance. Here, the threshold distance is determined based on the location of edge variants in training sequence reads that are categorized in the artifact training data category. Specifically, the threshold distance is expressed as the summation of the median distance of the edge variants from edges of sequence reads and the median absolute deviation of the median distance of the edge variants from edges of sequence reads. The simple edge variant filter is a simple indiscriminant filter that removes all variants that satisfy this threshold distance criteria. The second filter refers to the edge filtering process described with reference to the examples of FIGS. 26A-C, 27A-C, 28A-C, and 29, and further described below with reference to FIG. 32. Here, the sample specific edge variant filter identifies edge variants while considering the distribution of called variants observed for the sample.

The non-edge variants that remain after removing edge variants using either the simple edge variant filter or the sample specific edge variant filter are retained for analysis in comparison to a conventional method. As referred to hereafter, the conventional method refers to the identification of genomic variations from solid tumor samples using a conventional process, specifically the Memorial Sloan Kettering Integrated Mutation Profiling of Actionable Cancer Targets (MSK-IMPACT) Pipeline (Cheng, D., et al, *Memorial Sloan Kettering-Integrated Mutation Profiling of Actionable Cancer Targets (MSK-IMPACT), A Hybridization Capture-Based Next-Generation Sequencing Clinical Assay for Solid Tumor Molecular Oncology*, Journal of Molecular Diagnostics, 17(3), p. 251-264).

Here, called variants that are both non-edge variants and detected by the conventional method are referred to as concordant variants.

FIG. 30 depicts the concordant variants detected in a cfDNA sample following the application of an edge filter (or non-application of an edge filter) and called variants detected in solid tumor tissue as a fraction of the non-edge variants detected in cfDNA. This proportion can be expressed as:

$$\frac{\text{(True Variants detected in } cfDNA) \cap \text{(Variants detected in solid tumor tissue)}}{\text{(True Variants detected in } cfDNA)}$$

FIG. 31 depicts the concordant variants detected in a cfDNA sample following the application of an edge filter (or non-application of an edge filter) and called variants detected in solid tumor tissue as a fraction of the called variants detected in solid tumor tissue. This proportion can be expressed as:

$$\frac{\text{(True Variants detected in } cfDNA) \cap \text{(Variants detected in solid tumor tissue)}}{\text{(True Variants detected in solid tumor tissue)}}$$

The percentage of concordant variants shown in FIG. 30 and FIG. 31 depict several trends of interest. A significantly greater percentage of concordant variants is shown in FIG. 31 in comparison to the percentage of concordant variants depicted in FIG. 30. As an example, the percentage of concordant variants detected in breast cancer as a fraction of called variants detected solely in cfDNA is 9.8%, which is significantly lower than the 73% of concordant variants detected in breast cancer as a fraction of called variants detected in solid tumor tissue. This indicates that the identification of non-edge variants in cfDNA samples (irrespective of type of cancer) achieves higher sensitivity in comparison to the conventional method that calls variants in solid tumor tissue.

Referring to the simple edge variant filter in FIG. 30, the application of the simple edge variant filter increases the specificity of the called variants. For example, in comparison to the no edge variant filter, the application of the simple edge variant filter increases the specificity of called variants detected in breast cancer (e.g., 9.5% to 11%), in lung cancer (e.g., 45% to 49%), and in prostate cancer (e.g., 22% to 27%). However, this increase in specificity comes at a cost of sensitivity, as shown in FIG. 31. In comparison to the no edge variant filter, the application of the simple edge variant filter decreases the sensitivity of called variants detected in breast cancer (e.g., 73% to 69%), in lung cancer (e.g., 73% to 70%), and in prostate cancer (e.g., 76% to 71%).

Comparatively, the application of a sample specific edge variant filter improves specificity without sacrificing sensitivity. As shown in FIG. 30, in comparison to the no edge variant filter, the application of the sample-specific edge variant filter increases the specificity of called variants detected in breast cancer (e.g., 9.5% to 9.8%), in lung cancer (e.g., 45% to 47%), and in prostate cancer (e.g., 22% to 27%). Additionally, as shown in FIG. 31, in comparison to the no edge variant filter, the application of the sample-specific edge variant filter maintains the sensitivity of called variants detected in breast cancer (e.g., maintained at 73%), in lung cancer (e.g., maintained at 73%), and in prostate cancer (e.g., maintained at 76%).

X. Example Variant Caller

X. A. Example Combination of Different Filters and Scoring

Figure 32:
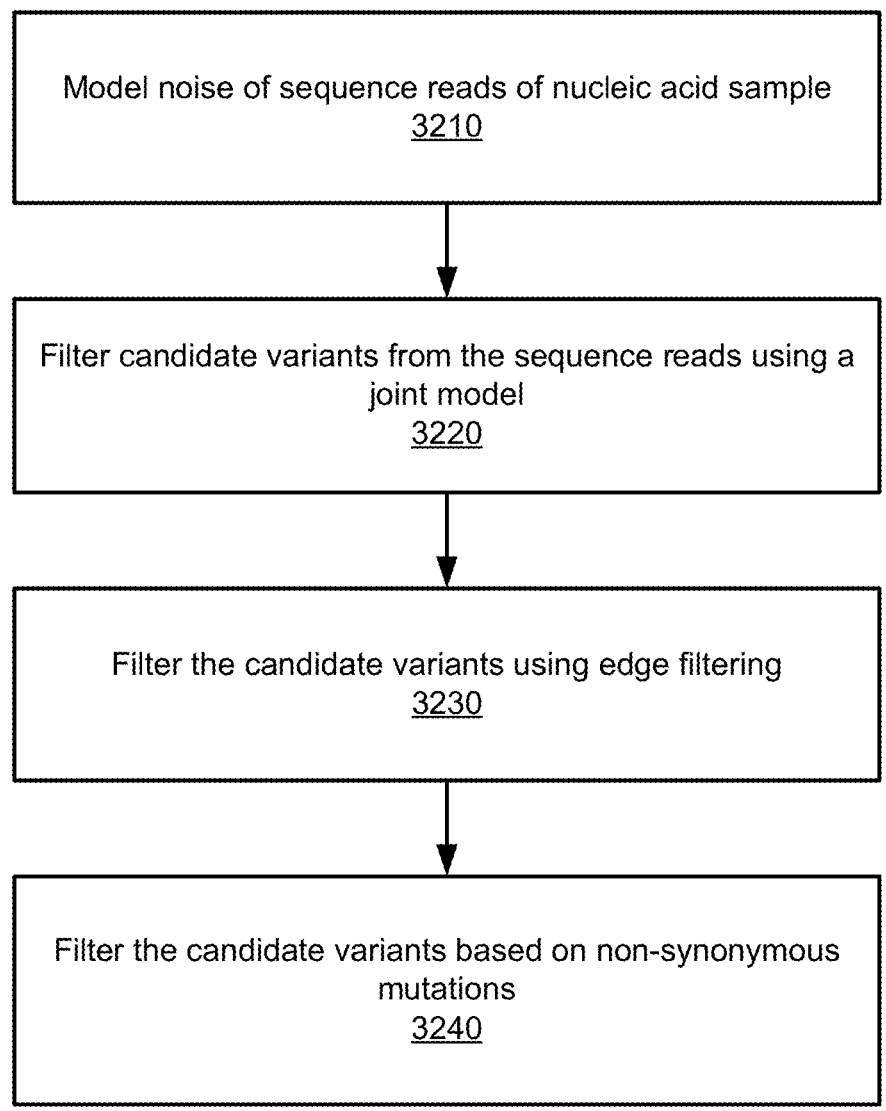
FIG. 32 is flowchart of a method for processing candidate variants using different types of filters and models according to one embodiment.

FIG. 32 is flowchart of a method 3200 for processing candidate variants using different types of filters and models 225 according to one embodiment. One or more steps of the method 3200 may be performed in conjunction with other methods described herein, or with another method. For example, the method 3200 may be performed as part of the method 300 shown in FIG. 3 to identify and remove any false positives, e.g., before calling variants. The method 3200 may include different, additional, or fewer steps than those described in conjunction with FIG. 32 in some embodiments or perform steps in different orders than the order described in conjunction with FIG. 32. For instance, the method 3200 may filter using a joint model but not with edge filtering. As a different example, the method 3200 may perform edge filtering before filtering using the joint model. In some embodiments, one or more steps may be combined, e.g., the method 3200 includes filtering using the joint model and edge filtering in the same step.

At step 3210, the processing system 200 uses at least one model 225 to model noise of sequence reads of a nucleic acid sample, e.g., a cfDNA sample. The model 225 may be a Bayesian hierarchical model as previously described with reference to FIGS. 4-9, which approximates expected noise distribution per position of the sequence reads. At step 3220, the processing system 200 filters candidate variants from the sequence reads using a joint model 225, e.g., as previously described with reference to FIGS. 10-19. In some embodiments, the processing system 200 uses the joint model 225 to determine whether a given candidate variant observed in the cfDNA sample is likely associated with a nucleotide mutation of a corresponding gDNA sample (e.g., from white blood cells).

At step 3230, the processing system 200 filters the candidate variants using edge filtering, in some embodiments. In particular, the edge filter 250 may use a sample-specific rate prediction model 2415 (see FIG. 24A) and an edge variant prediction model 2435 (see FIG. 24B) to determine how aggressively to filter the sample to remove edge variants, e.g., as previously described with reference to FIGS. 23A-31. In some embodiments, the score engine 235 uses the models for edge filtering to analyze and assign a support score to each candidate variant (or called variant), where the support score represents a level of confidence that the candidate variant is a non-edge variant. The edge filter 250 keeps a candidate variant associated with a support score that greater than a threshold score, whereas the edge filter 250 filters out candidate variants associated with a support score less than (or equal to) the threshold score. In some embodiments, the score engine 235 generates the support score for a candidate variant based on prior knowledge about the candidate variant and/or systematic errors observed in a set of healthy samples for that chromosome/position. In some scenarios, the support score may be determined based on sequencing depth of a target region including the candidate variant, and the threshold score may be based on an average sequencing depth of the target region in a set of previously sequenced samples (e.g., reference data).

As described above regarding the edge filter 250, sequence reads obtained from sample may include both sequence reads that that include an alternative allele as well as sequence reads that include a reference allele. Specifically, given the collection of candidate variants for a sample, the edge filter 250 may perform a likelihood estimation to determine a predicted rate of edge variants in the sample. Given certain conditions of the sample, the predicted rate may best explain the observed collection of candidate variants for the sample in view of two distributions. One distribution describes features of known edge variants whereas another trained distribution describes features of known non-edge variants. The predicted rate is a sample-specific parameter that controls how aggressively the sample is analyzed to identify and filter edge from the sample. Edge variants of the sample are filtered and removed, leaving non-edge variants for subsequent consideration (e.g., for determination of presence/absence of cancer or likelihood of cancer or other disease).

At step 3240, the non-synonymous filter 260 may optionally filter the candidate variants based on non-synonymous mutations, in some embodiments. In contrast to a synonymous mutation, a non-synonymous mutation of a nucleic acid sequence results in a change in the amino acid sequence of a protein associated with the nucleic acid sequence. For instance, non-synonymous mutations may alter one or more phenotypes of an individual or cause (or leave more vulnerable) the individual to develop cancer, cancerous cells, or other types of diseases. In some embodiments, the non-synonymous filter 260 determines that a candidate variant should result in a non-synonymous mutation by determining that a modification to one or more nucleobases of a trinucleotide would cause a different amino acid to be produced based on the modified trinucleotide. In some embodiments, the non-synonymous filter 260 keeps candidate variants associated with non-synonymous mutations and filters out other candidate variants associated with synonymous mutations because the former group of candidate variants are more likely to have a functional impact on an individual.

X. B. Examples of Combined Filtering and Scoring

Figure 33B:
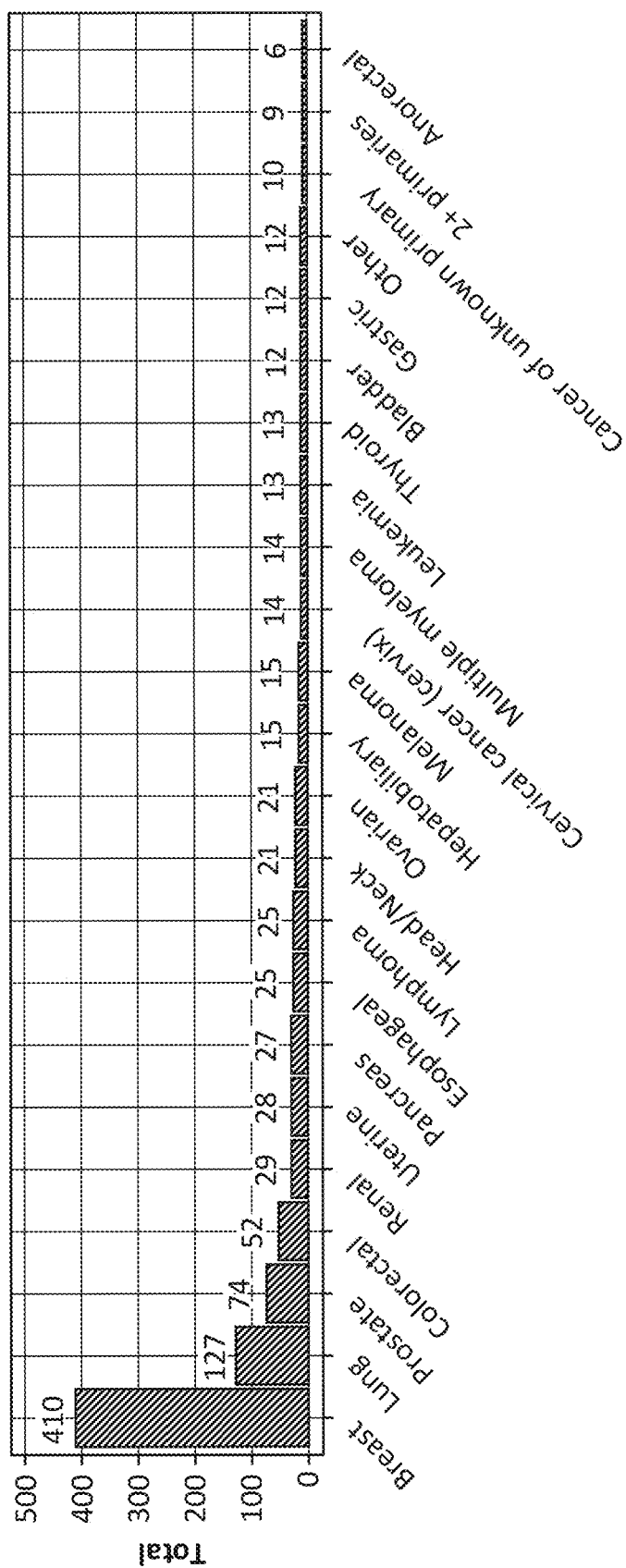
FIG. 33B is a chart indicating types of cancers associated with the sample set for the cell free genome study of FIG. 33A according to one embodiment.

The example data in the following FIGS. 34A-H were generated using sequence reads obtained from a sample set of individuals of a cell free genome study and processed using one or more of the methods described herein (e.g., noise modeling, joint modeling, edge filtering, non-synonymous filtering, etc.). The sample set includes healthy individuals from which blood samples (e.g., cfDNA) were obtained. Additionally, the sample set includes individuals known to have at least one type of cancer, from which blood samples and tissue samples (e.g., tumor or gDNA) were obtained. The data was collected from individuals over approximately 140 centers in the United States of America and Canada. FIGS. 33A-C show further details regarding the sample set.

Figure 34A:
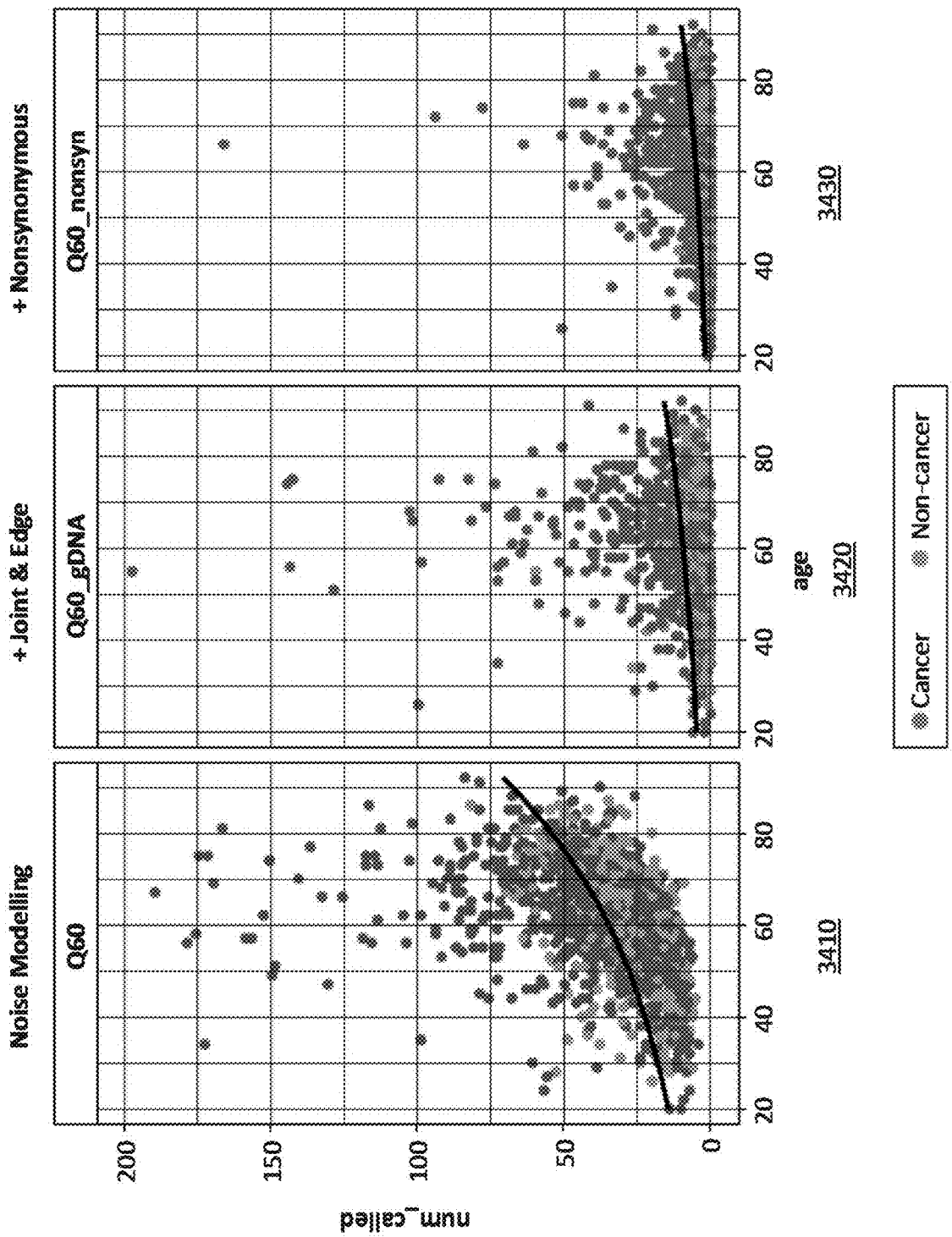
FIG. 34A shows diagrams of example counts of called variants determined using one or more types of filters and models according to one embodiment.

FIG. 33A is a table describing individuals of a sample set for a cell free genome study according to one embodiment. The sample set includes samples known to have at least breast, lung, prostate, colorectal, and other types of cancer. The demographic data (e.g., age, gender, and ethnicity) of the individuals are also shown in FIG. 33A. FIG. 33B is a chart indicating types of cancers associated with the sample set for the cell free genome study of FIG. 33A according to one embodiment. FIG. 33C is another table describing the sample set for the cell free genome study of FIG. 33A according to one embodiment. Particularly, the table shows counts of the samples known to have cancer organized based on clinical stages of the cancers. FIG. 34A shows diagrams of example counts of called variants determined using one or more types of filters and models according to one embodiment. Each of the diagrams includes data points of the sample set plotted on an x-axis representing age of the corresponding individual and a y-axis representing a number of called variants after processing by the processing system 200. Diagram 3410 includes results from processing sequence reads of the sample set using noise modeling. Diagram 3420 includes results from processing sequence reads of the sample set using joint modeling and edge filtering in addition to the noise modeling. Diagram 3430 includes results from processing sequence reads of the sample set using non-synonymous filtering in addition to the joint modeling, edge filtering, and noise modeling. Further, the example results shown in FIGS. 34B-H were also generated using non-synonymous filtering in addition to the joint modeling, edge filtering, and noise modeling.

As illustrated by the progression of diagrams, the number of called variants generally decreases as the extent of filtering increases. Thus, the examples suggest that that non-synonymous filtering, joint modeling, edge filtering, and noise modeling by the processing system 200 can successfully identify and remove a notable amount of false positives. Accordingly, the processing system 200 provides for a more accurate variant caller that mitigates influence from various sources of noise or artifacts. Targeted assays analyzing cfDNA from blood samples using the disclosed methods may be able to capture tumor relevant biology. A slight proportional correlation may be observed in the diagrams between the count of called variants and age of the individuals (e.g., more evident in diagram 3410). Moreover, there are greater counts of called variants for cancer samples than non-cancer samples as expected.

Figure 34B:
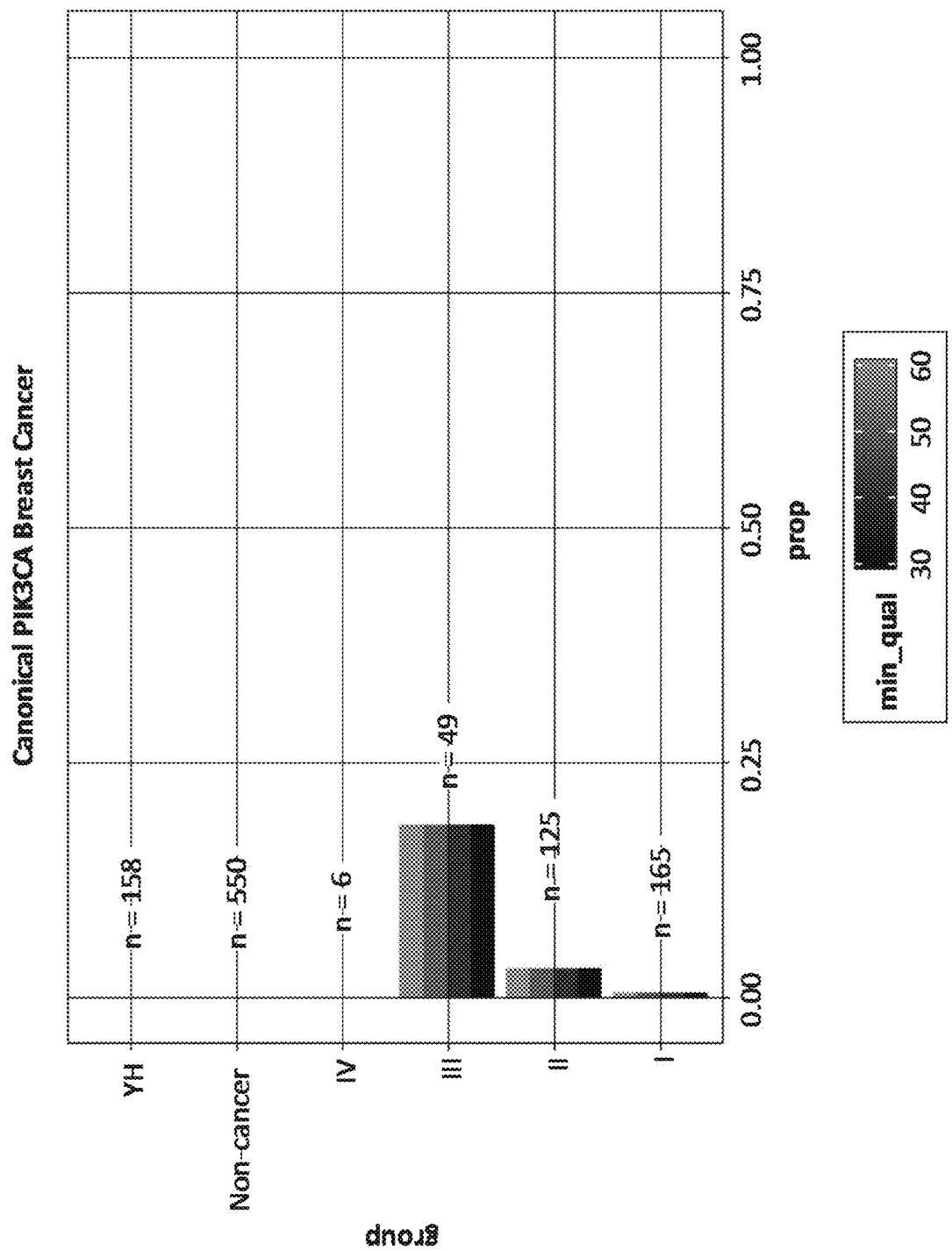
FIG. 34B is a diagram of example quality scores of samples known to have breast cancer according to one embodiment.
Figure 34C:
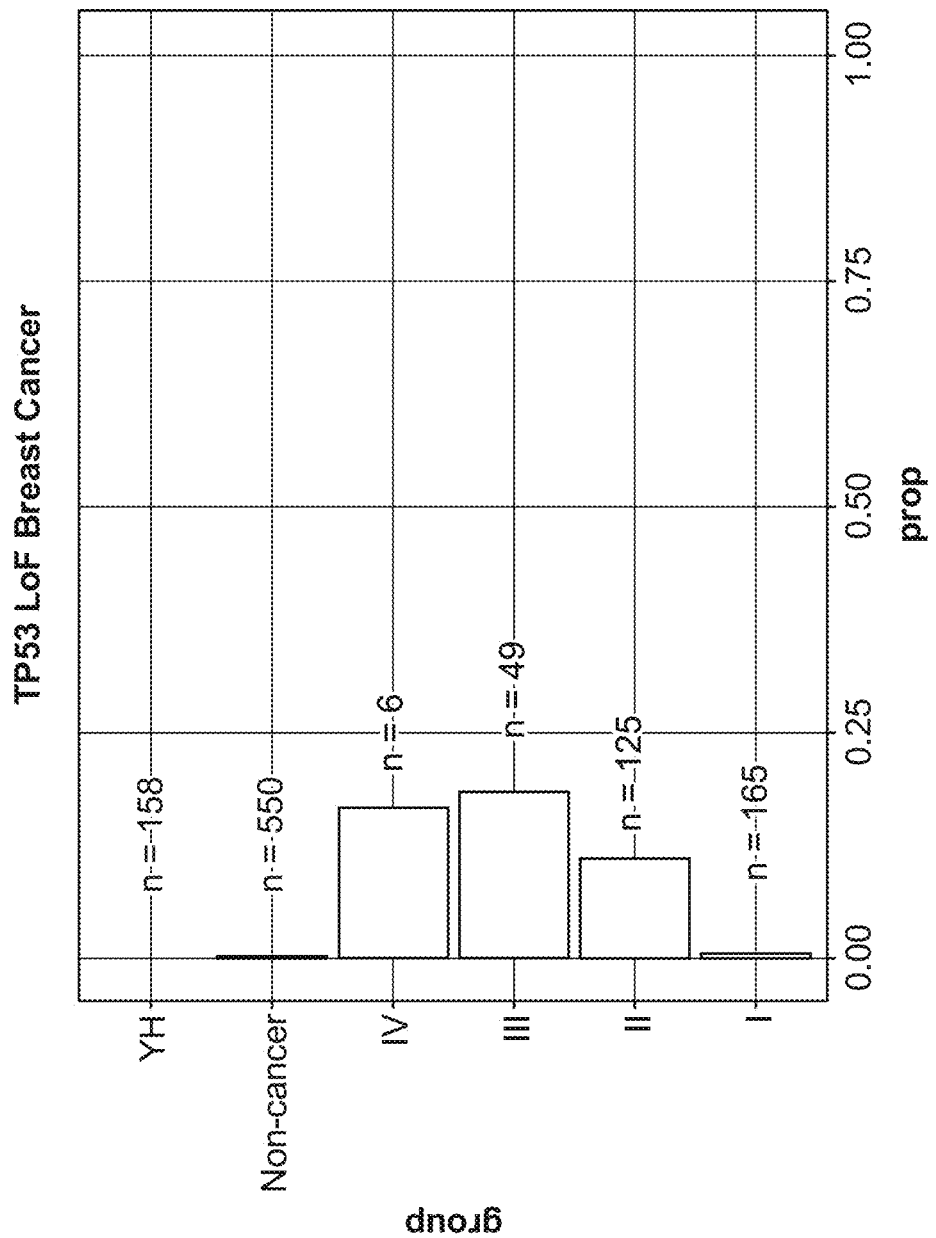
FIG. 34C is another diagram of example quality scores of samples known to have breast cancer according to one embodiment.
Figure 34D:
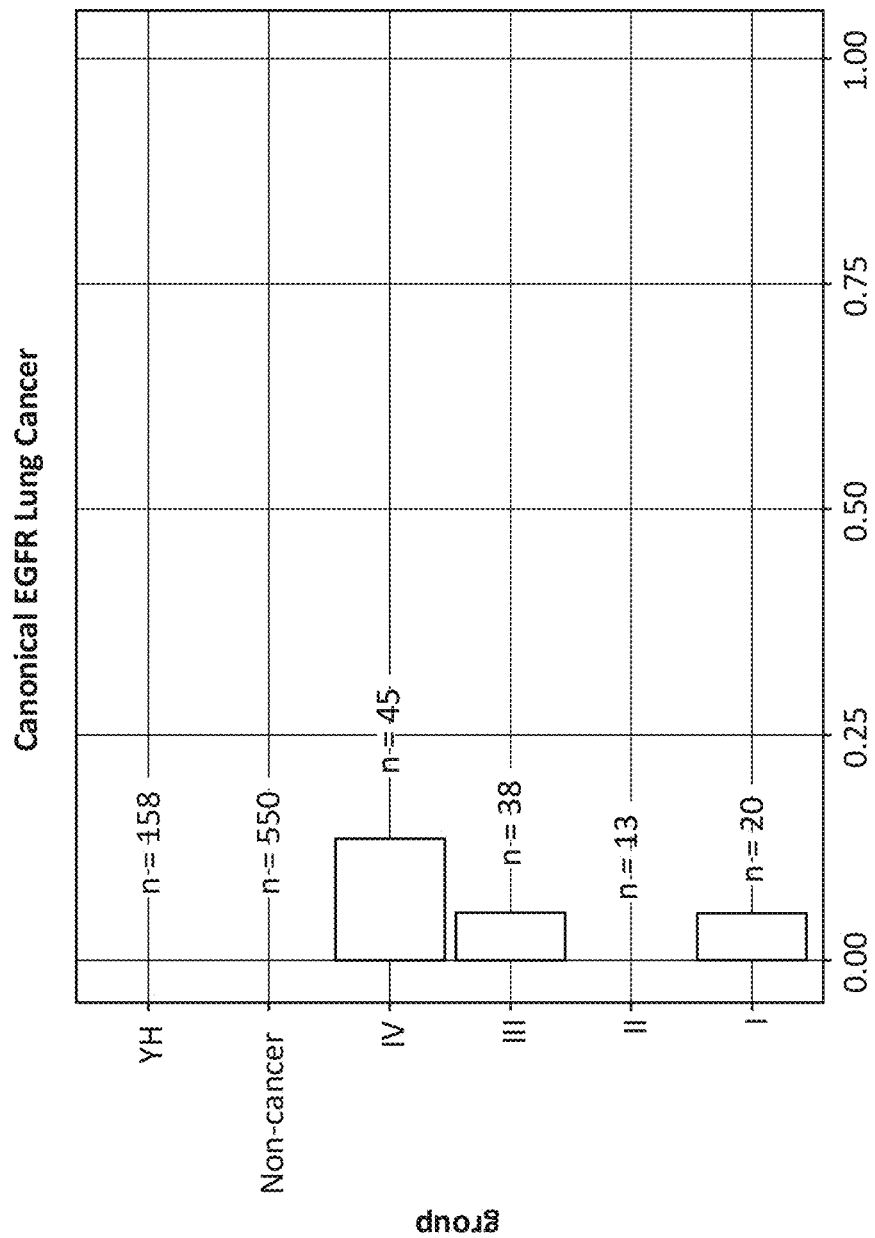
FIG. 34D is a diagram of example quality scores of samples known to have lung cancer according to one embodiment.

FIG. 34B is a diagram of example quality scores of samples known to have breast cancer according to one embodiment. FIG. 34C is another diagram of example quality scores of samples known to have breast cancer according to one embodiment. FIG. 34D is a diagram of example quality scores of samples known to have lung cancer according to one embodiment. The quality scores may be determined by the score engine 235 using a noise model 225 as previously described with reference to FIGS. 3, 4, and 9. In particular, FIGS. 34B, 34C, and 34D show quality scores for candidate variants of sequence reads from canonical PIK3CA, TP53 loss-of-function (LoF), and canonical epidermal growth factor receptor (EGFR) genes, respectively. The x-axes represent the proportion of individuals having a certain canonical mutation in a given group (e.g., stage of cancer). FIGS. 34B-D indicate a trend where the quality scores tend to increase as the stages of cancer increase from group I to group IV.

FIG. 34E is a table of example counts of called variants for samples known to have various types of cancer and at different stages of cancer according to one embodiment. Similar to FIGS. 34B-D, FIG. 34E also shows a trend where the number of called variants tend to increase as the stages of cancer increase from group I to group IV.

Figure 34F:
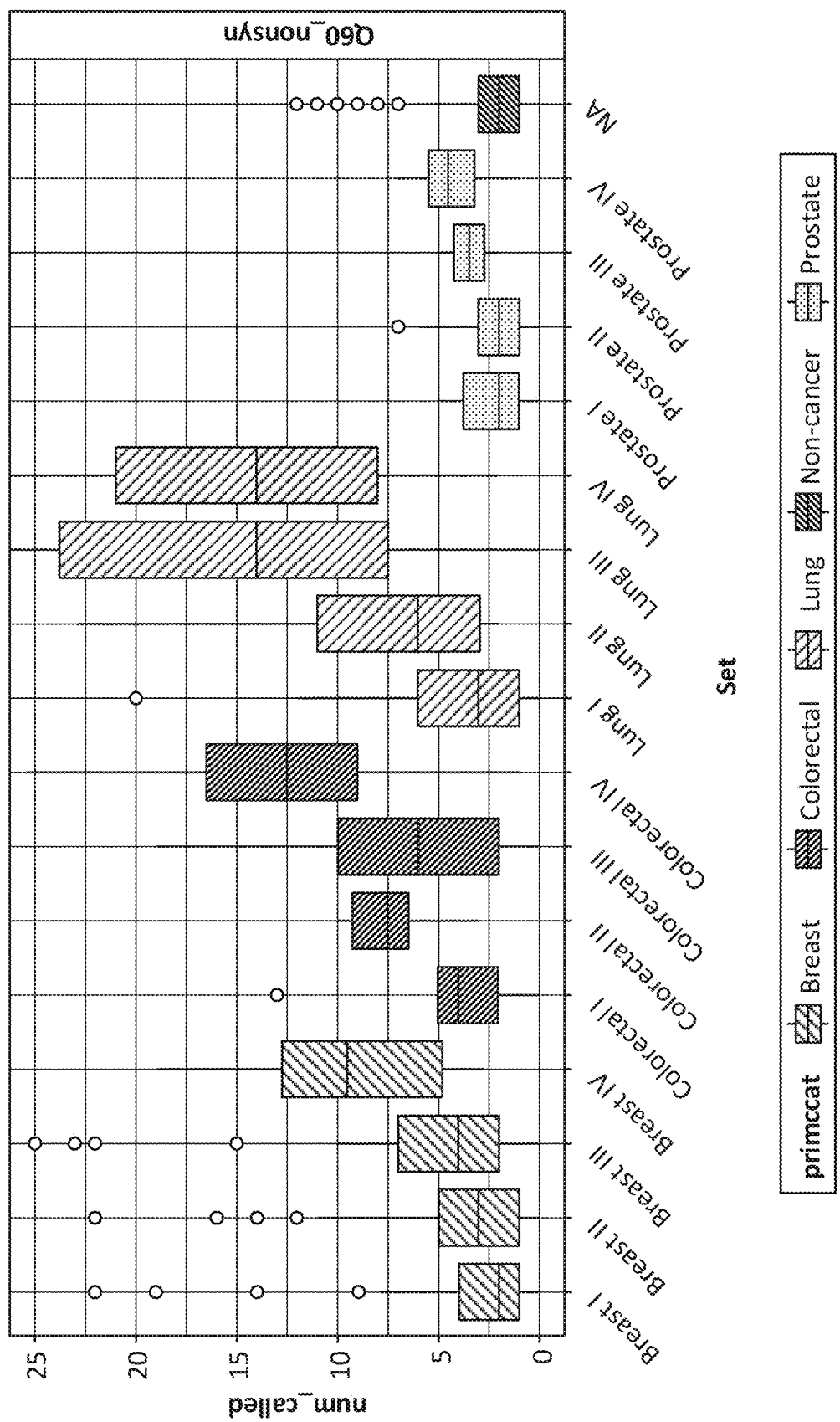
FIG. 34F is a diagram of example counts of called variants for samples known to have various types of cancer and at different stages of cancer according to one embodiment.

FIG. 34F is a diagram of example counts of called variants for samples known to have various types of cancer and at different stages of cancer according to one embodiment. As shown by the box plots for samples known to have breast, colorectal, lung, or prostate cancers, the median number of called variants tend to increase as the stages of cancer increase from I to IV, and the number for non-cancer samples is relatively lower compared to those of the cancer samples.

Figure 34G:
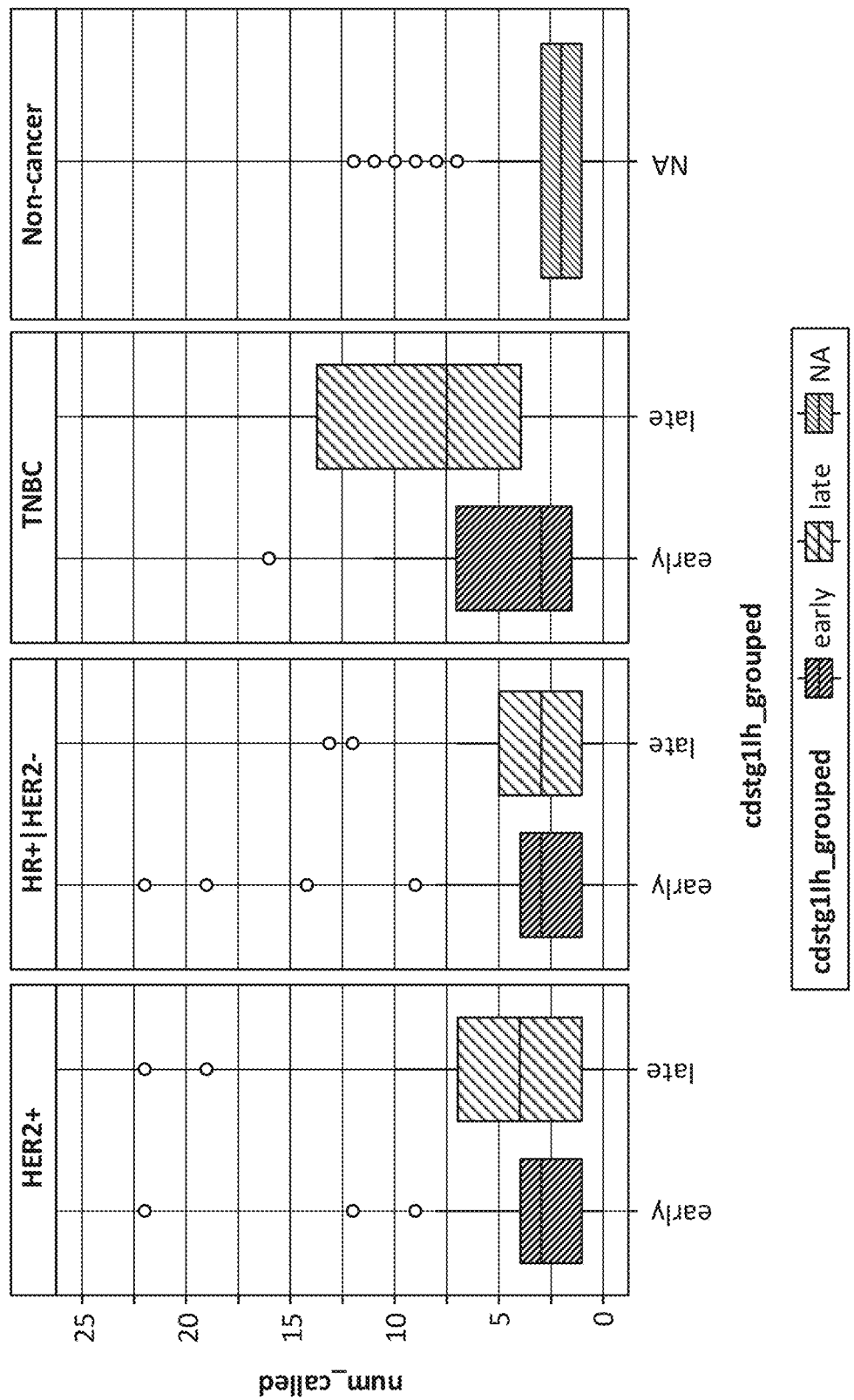
FIG. 34G is a diagram of example counts of called variants for samples known to have early or late stage cancer according to one embodiment.
Figure 34H:
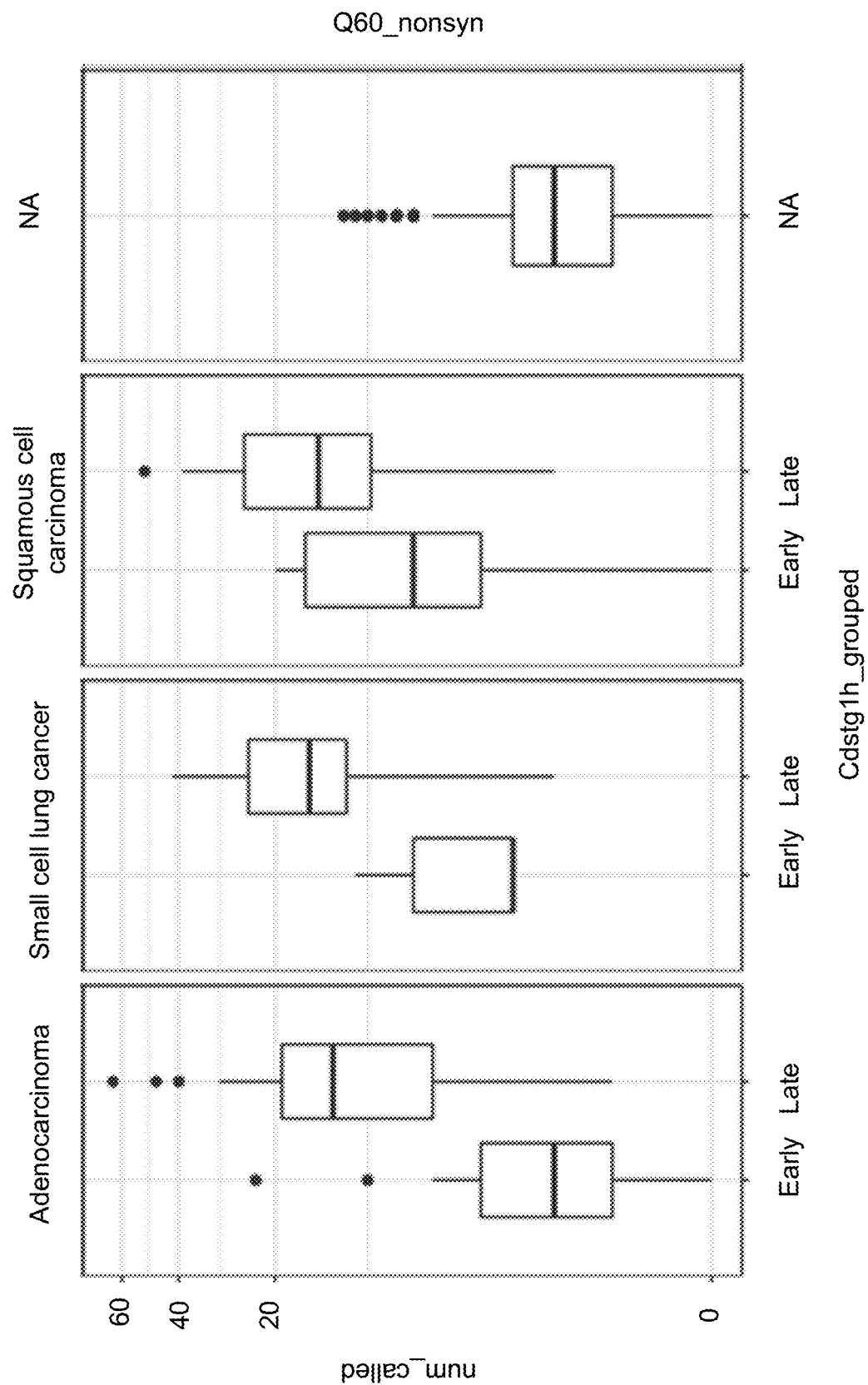
FIG. 34H is another diagram of example counts of called variants for samples known to have early or late stage cancer according to one embodiment.

FIG. 34G is a diagram of example counts of called variants for samples known to have early or late stage cancer according to one embodiment. FIG. 34H is another diagram of example counts of called variants for samples known to have early or late stage cancer according to one embodiment. In particular, FIG. 34G and FIG. 34H show called variants of sequence reads from cdstg11h_grouped genes associated with breast cancer (e.g., HER2+, HR+|HER2−, TNBC) and lung cancer (e.g., Adenocarcinoma, small cell lung cancer, and squamous cell carcinoma), respectively. FIGS. 34G-H show a trend where the number of called variants tend to increase as the cancers progress from early stage to late stage. The example data indicates that the processing system 200 can detect different subtypes or variants of sequences in genes. Additionally, the number for non-cancer samples is relatively lower compared to those of the cancer samples.

XI. Example Features for Cancer Model

XI. A. Example Small Variant Features

As used hereafter, a small variant sequencing assay refers to a physical assay that generates sequence reads, typically through targeted gene sequencing panels that can be used to determine small variants, examples of which include single nucleotide variants (SNVs) and insertions or deletions. Alternatively, as one of skill in the art would appreciate, assessment of small variants may also be done using a whole genome sequencing approach or a whole exome sequencing approach. An example small variant sequencing assay is previously described with reference to FIG. 1A.

In some embodiments, sequence reads generated from application of a small variant sequencing assay are processed using a computational analysis, which outputs one or more small variant features. The computational analysis (also referred to as a small variant computational assay) may include steps from any of the methods described herein, for example, as shown in FIG. 1A, 3, 8-10, 20, 25, or 32. For instance, small variant features are generated using the candidate variants output in step 324 of the method 300 of FIG. 3. Moreover, the computational analysis may involve any number of trained models ("Bayesian Hierarchical model," "Joint Model," etc.) or filters of the embodiments described herein. Example small variant features include a total number of somatic variants, a total number of nonsynonymous variants, a total number of synonymous variants, a presence or absence of somatic variants per gene, a presence or absence of somatic variants for particular genes that are known to be associated with at least one type of cancer, an allele frequency of a somatic variant per gene, order statistics according to AF of somatic variants, classification of somatic variants that are known to be associated with at least one type of cancer based on their allele frequency, an allele frequency (AF) of a somatic variant per gene in a gene panel, an AF of a somatic variant per category as designated by a publicly available database, such as OncoKB, and a ranked order of somatic variants according to the AF of somatic variants.

The feature representing the AF of a somatic variant per gene (e.g., in a targeted gene panel) refers to a measure of the frequency of somatic variants in the sequence reads that relate to a particular gene. Generally, this feature is represented by one feature value per gene of a gene panel or per gene across the genome. The value of this feature can be a statistical value of AFs of somatic variants of the gene. The exact measurement used to prescribe a value to the feature can vary by embodiment. In one embodiment, the value for this feature is determined as the maximum AF of all somatic variants in the gene per position (e.g., in the genome). In another embodiment, the value for this feature is determined as the average AF of all somatic variants of the gene per position. Therefore, for an example targeted gene panel of 500 genes, there are 500 feature values that represent the AF of a somatic variant per gene. Measures other than max AF or mean AF may also be used.

The feature(s) representing the AF of a somatic variant per category can be determined by accessing a publicly available database, such as OncoKB. Chakravarty et al., JCO PO 2017. For example, OncoKB categorizes clinical information of genes in one of four different categories such as FDA approved, standard care, emerging clinical evidence, and biological evidence. Each such category may be its own feature having its own corresponding value. Other publicly available databases that may be accessed for determining features include the Catalogue Of Somatic Mutations In Cancer (COSMIC) and The Cancer Genome Atlas (TCGA) supported by the National Cancer Institutes' Genomic Data Commons (GDC). Forbes et al. COSMIC: somatic cancer genetics at high-resolution, Nucleic Acids Research, Volume 45, Issue D1, 4 Jan. 2017, Pages D777-D783. In one embodiment, the value of the AF of a somatic variant per category feature is determined as a maximum AF of a somatic variant across the genes in the category. In another embodiment, the value of the AF of a somatic variant per category feature is determined as a mean AF across somatic variants across the genes in the category. Measures other than max AF per category and mean AF per category may also be used.

Generally, the feature values for the small variant features are predicated on the accurate identification of somatic variants that may be indicative of cancer in the individual. The small variant computational analysis identifies candidate variants and from amongst the candidate variants, differentiates between somatic variants likely present in the genome of the individual and false positive variants that are unlikely to be predictive of cancer in the individual. More specifically, the small variant computational analysis identifies candidate variants present in cfDNA that are likely to be derived from a somatic source in view of interfering signals such as noise and/or variants that can be attributed to a genomic source (e.g., from gDNA or WBC DNA). Additionally candidate variants can be filtered to remove false positive variants that may arise due to an artifact and therefore are not indicative of cancer in the individual. As an example, false positive variants may be variants detected at or near the edge of sequence reads, which arise due to spontaneous cytosine deamination and end repair errors. Thus, somatic variants, and features thereof, that remain following the filtering out of false positive variants can be used to determine the small variant features.

For the feature of the total number of somatic variants, the small variant computational analysis totals the identified somatic variants across the genome, or gene panel. Thus, for a cfDNA sample obtained from an individual, the feature of the total number of somatic variants is represented as a single, numerical value of the total number of somatic variants identified in the cfDNA of the sample.

For the feature of the total number of nonsynonymous variants, the small variant computational analysis may further filter the identified somatic variants to identify the somatic variants that are nonsynonymous variants. As is well known in the art, a non-synonymous variant of a nucleic acid sequence results in a change in the amino acid sequence of a protein associated with the nucleic acid sequence. For instance, non-synonymous variants may alter one or more phenotypes of an individual or cause (or leave more vulnerable) the individual to develop cancer, cancerous cells, or other types of diseases. Therefore, the small variant computation analysis determines that a candidate variant would result in a non-synonymous variant by determining that a modification to one or more nucleobases of a trinucleotide would cause a different amino acid to be produced based on the modified trinucleotide. A feature value for the total number of nonsynonymous variants is determined by summating the identified nonsynonymous variants across the genome. Thus, for a cfDNA sample obtained from an individual, the feature of the total number of nonsynonymous variants is represented as a single, numerical value.

For the feature of the total number of synonymous variants, synonymous variants represent other somatic variants that are not categorized as nonsynonymous variants. In other words, the small variant computational analysis can perform the filtering of identified somatic variants, as described in relation to nonsynonymous variants, and identify the synonymous variants across the genome, or gene panel. Thus, for a cfDNA sample obtained from an individual, the feature of the total number of synonymous variants is represented as a single numerical value.

The feature of a presence/absence of somatic variants per gene can involve multiple feature values for a cfDNA sample. For example, a targeted gene panel may include 500 genes in the panel and therefore, the small variant computational analysis can generate 500 feature values, each feature value representing either a presence or absence of somatic variants for a gene in the panel. As an example, if a somatic variant is present in the gene, then the value of the feature is 1. Conversely, if a somatic variant is not present in the gene, then the value of the feature is 0. In general, any size gene panel may be used. For example, the gene panel may comprise 100, 200, 500, 1000, 2000, 10,000 or more genes targets across the genome. In other embodiments, the gene panel may comprise from about 50 to about 10,000 gene targets, from about 100 to about 2,000 gene targets, or from about 200 to about 1,000 gene targets.

For the feature of presence/absence of somatic variants for particular genes that are known to be associated with cancer, the particular genes known to be associated with cancer can be accessed from a public database such as OncoKB. Examples of genes known to be associated with cancer include p53, LRP1B, and KRAS. Each gene known to be associated with cancer can be associated with a feature value, such as a 1 (indicating that a somatic variant is present in the gene) or a 0 (indicating that a somatic variant is not present in the gene).

The AF of a somatic variant per gene (e.g., in a gene panel) refers to the frequency of one or more somatic variants in the sequence reads. Generally, this feature is represented by one feature value per gene of a gene panel or per gene across the genome. The value of this feature can be a statistical value of AFs of somatic variants of the gene. In various embodiments, this feature refers to the one somatic variant in the gene with the maximum AF. In some embodiments, this feature refers to the average AF of somatic variants of the gene. Therefore, for a targeted gene panel of 500 genes, there are 500 feature values that represent the AF of a somatic variant per gene (e.g., in a gene panel).

The AF of a somatic variant per category as designated by a publicly available database, such as OncoKB. For example, OncoKB categorizes genes in one of four different categories. In one embodiment, the AF of a somatic variant per category is a maximum AF of a somatic variant across the genes in the category. In one embodiment, the AF of a somatic variant per category is a mean AF across somatic variants across the genes in the category.

The ranked order of somatic variants according to the AF of somatic variants refers to the top N allele frequencies of somatic variants. In general, the value of a variant allele frequency can be between 0 to 1, where a variant allele frequency of 0 indicates no sequence reads that possess the alternate allele at the position and where a variant allele frequency of 1 indicates that all sequence reads possess the alternate allele at the position. In other embodiments, other ranges and/or values of variant allele frequencies can be used. In various embodiments, the ranked order feature is independent of the somatic variants themselves and instead, is only represented by the values of the top N variant allele frequencies. An example of the ranked order feature for the top five allele frequencies can be represented as: [0.1, 0.08, 0.05, 0.03, 0.02] which indicates that the five highest allele frequencies, independent of the somatic variants, range from 0.02 up to 0.1.

XI. B. Example Predictive Cancer Model

Small variant features may be used as input to one or more types of models such as a predictive cancer model. The predictive cancer model may generate predications associated with cancer, e.g., predicting a likelihood that a given individual has, or is likely to develop, at least one particular type of cancer or disease. The predictive cancer model may be used to predict detections of one or more of stage I, stage II, stage III, and stage IV cancer. Example types of cancer include breast cancer, lung cancer, colorectal cancer, ovarian cancer, uterine cancer, melanoma, renal cancer, pancreatic cancer, thyroid cancer, gastric cancer, hepatobiliary cancer, esophageal cancer, prostate cancer, lymphoma, multiple myeloma, head and neck cancer, bladder cancer, cervical cancer, or any combination thereof. In some embodiments, the predictive cancer model is used to classify breast cancer as HR positive, HER2 overexpression, HER2 amplified, or triple negative, based on analysis of the sequence reads from a test sample.

In some embodiments, analysis using a predictive cancer model includes detecting the presence of one or more viral-derived nucleic acids in a test sample. The detection of cancer may be based, in part, on detection of the one or more viral nucleic acids. In some embodiments, the one or more viral-derived nucleic acids are selected from the group consisting of human papillomavirus, Epstein-Barr virus, hepatitis B, hepatitis C, and any combination thereof.

Figure 35A:
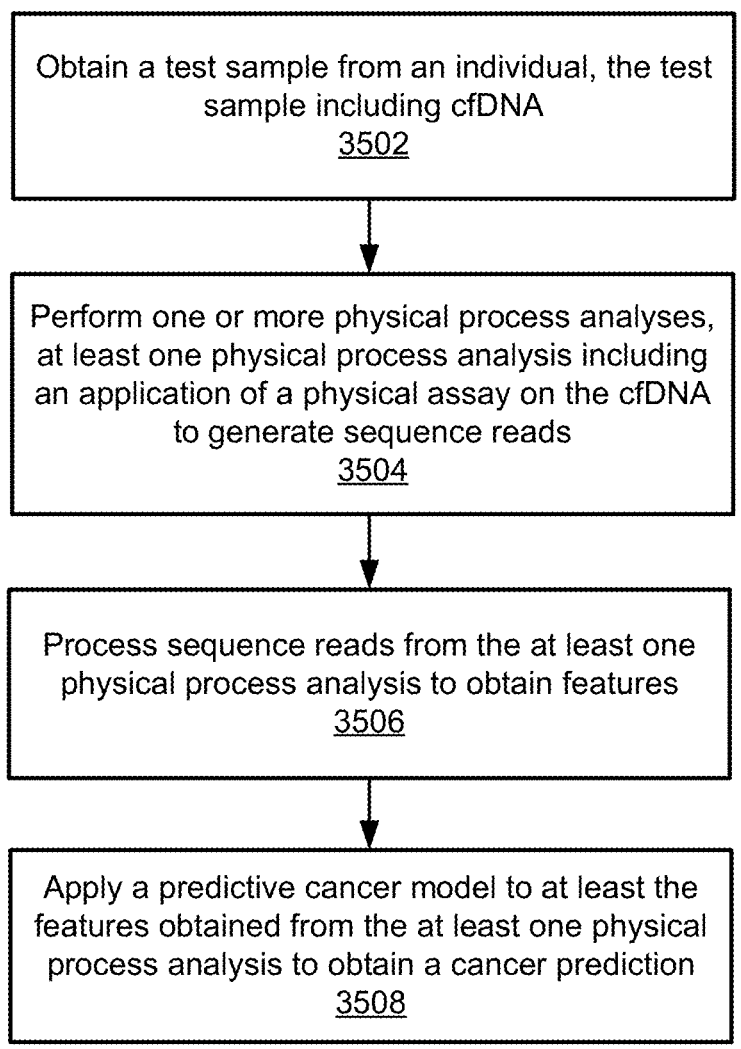
FIG. 35A is a flowchart of a method for generating a cancer prediction based on features derived from a cfDNA sample, obtained from an individual according to one embodiment.

FIG. 35A is a flowchart of a method 3500 for generating a cancer prediction based on features derived from a cfDNA sample, obtained from an individual according to one embodiment. In other embodiments, the method 3500 may be used to generate predictions of one or more types of diseases (e.g., hereditary diseases or cardiovascular disease), other health related conditions (e.g., clonal hematopoiesis of indeterminate potential (ChIP)), other classifications, or other metrics. At step 3502, a test sample is obtained from the individual. Generally, samples may be from healthy subjects, subjects known to have or suspected of having cancer, or subjects where no prior information is known (e.g., asymptomatic subjects). The test sample may be a sample selected from the group consisting of blood, plasma, serum, urine, fecal, and saliva samples. Alternatively, the test sample may comprise a sample selected from the group consisting of whole blood, a blood fraction, a tissue biopsy, pleural fluid, pericardial fluid, cerebral spinal fluid, and peritoneal fluid. The test sample may include cfDNA. In various embodiments, a test sample may include genomic DNA (gDNA), e.g., from white blood cell (WBC) DNA.

At step 3504, one or more physical process analyses are performed, at least one physical process analysis including a sequencing-based assay on cfDNA to generate sequence reads. At step 3506, the sequence reads generated as a result of performing the sequencing-based assay are processed to determine values for features. Features, generally, are types of information obtainable from physical assays and/or computational analyses that may be used in predicting cancer in an individual. Generally, any given predictive model for identifying cancer in an individual includes one or more features as constituent components of the model. For any given patient or sample, a feature will have a value that is determined from the physical and/or computational analysis. These values are input into the predictive model to generate an output of the model.

Sequence reads are processed by applying a computational analysis. Generally, each computational analysis represents an algorithm that is executable by a processor of a computer, hereafter referred to as a processing system. Therefore, each computational analysis analyzes sequence reads and outputs values features based on the sequence reads. Each computational analysis is specific for a given sequencing-based assay and therefore, each computational analysis outputs a particular type of feature that is specific for the sequencing-based assay. Sequence reads generated from application of a small variant sequencing assay are processed using a computational analysis, otherwise referred to as a small variant computational analysis. The computational analysis outputs small variant feature(s).

At step 3508, a predictive cancer model is applied to the features to generate a cancer prediction for the individual. Examples of a cancer prediction include a presence or absence of cancer, a tissue of origin of cancer, a severity, stage, a grade of cancer, a cancer sub-type, a treatment decision, and a likelihood of response to a treatment. In various embodiments, the cancer prediction output by the predictive cancer model is a score, such as a likelihood or probability that indicates one or more of: a presence or absence of cancer, a tissue of origin of cancer, a severity, stage, a grade of cancer, a cancer sub-type, a treatment decision, and a likelihood of response to a treatment.

Generally, any such scores may either be singular, such as the presence absence of cancer generally, presence/absence of a particular type of cancer. Alternatively, such scores may be plural, such that the output of the predictive cancer model may, for example, be a score representing the presence/absence of each of a number of types of cancer, a score representing the severity/grade of each of a number of types of cancer, a score representing the likelihood that particular cfDNA originated in each of a number of types of tissue, and so on. For clarity of description, the output of the predictive cancer model is generally referred to as a set of scores, the set comprising one or more scores depending upon what the predictive cancer model is configured to determine.

In various embodiments, the predictive cancer model can be one of a decision tree, an ensemble (e.g., bagging, boosting, random forest), gradient boosting machine, linear regression, Naïve Bayes, neural network, or logistic regression. Each predictive cancer model includes learned weights for the features that are adjusted during training. The term weights is used generically here to represent the learned quantity associated with any given feature of a model, regardless of which particular machine learning technique is used.

During training, training data is processed to generate values for features that are used to train the weights of the predictive cancer model. As an example, training data can include cfDNA and/or WBC DNA obtained from training samples, as well as an output label. For example, the output label can be indication as to whether the individual is known to be cancerous or known to be devoid of cancer (e.g., healthy), an indication of a cancer tissue of origin, or an indication of a severity of the cancer. Depending on the particular embodiment, the predictive cancer model receives the values for one or more of the features obtained from one or more the physical assays and computational analyses relevant to the model to be trained. Depending on the differences between the scores output by the model-in-training and the output labels of the training data, the weights of the predictive cancer model are optimized enable the predictive cancer model to make more accurate predictions. In various embodiments, a predictive cancer model may be a non-parametric model (e.g., k-nearest neighbors) and therefore, the predictive cancer model can be trained to more accurately make predictions without having to optimize parameters. The trained predictive cancer model can be stored and subsequently retrieved when needed, for example, during deployment in step 3508 of FIG. 35A.

XI. C. Example Feature Tuning

In various embodiments, during preparation of sequence reads from a small variant sequencing assay, or during computational analysis, one or more steps may be performed to improve, tune, or optimize the output features. For instance, as result of tuned features, a predictive cancer model may generate predictions with greater sensitivity (e.g., true positive detection rate) or specificity (e.g., false positive detection rate).

The processing system 200 may determine that a small variant potentially belong to one or more particular biological categories. Biological categories indicate, for example, a gene, intron or exon of a gene, particular region of a gene such as a five prime untranslated region (5' UTR), three prime untranslated region (3' UTR), or enhancer region, or protein coding region, among other suitable categories. Responsive to the determination, the processing system 200 may label the small variant with annotations of the corresponding biological categories. In some embodiments, the processing system 200 determines a likelihood that the small variant belongs to a category and annotates the small variant responsive to determining that the likelihood is greater than a threshold.

The processing system 200 may use information extracted using the Ensemble Variant Effect Predictor (VEP) tool for annotation. Based on an input position (e.g., in the genome) of a small variant and a corresponding type of mutation (e.g., SNV or indel), the VEP may determine effect of the variant on one or more genes (e.g., canonical representation or structure of the gene), or any downstream products created therefrom, such as transcripts, protein sequences, and regulatory regions. By evaluating these effects, the processing system 200 may determine whether to assign a particular biological category to a small variant. In addition to determining which biological category (e.g., splicing sites, UTRs, synonymous or non-synonymous sites) to use, the processing system 200 may determine a gene representation (e.g., canonical transcript or other isoforms) to use for determining features. In one embodiment, the processing system 200 includes genes having a dash character (–) in a string representation of the gene name as a potential biological category for annotation. For instance, the processing system 200 processes small variants in the NKX2-1 and NKX3-1 genes. NKX2-1 may be used as biomarker for lung or thyroid tumor, and NKX3-1 is known to be a prostatic tumor suppressor gene.

The annotations are intended to label small variants affecting the set of coding genes covered by a targeted gene sequencing panel. In addition to labeling small variants that are nonsynonymous (e.g., affecting a corresponding amino acid of a gene), the processing system 200 can also label small variants that may otherwise influence gene transcription or expression. For example, a TERT (Telomerase reverse transcriptase) promoter can influence the telomere length or transcription mechanics. Since TERT promoter mutations may be a biomarker of tumorigenesis, the processing system 200 may be configured to systematically annotate small variants in these regions. As another example, splice site mutations may also influence transcription or protein translation, even though a splice site mutation may not necessarily be located in a coding region. Since splice sites are located near boundaries of exons or introns, a splice site mutation may cause one or more exons to be dropped or added during transcription. Thus, the splice site mutation may affect resulting protein structure without modifying an amino acid in an intermediate step.

In one embodiment, the processing system 200 uses annotation information to help determine small variant features input to a predictive cancer model for cancer predictions. In the same or a different embodiment, annotation itself may be a feature, where the value of the feature is the specific annotation assigned to each gene per position (e.g., in the genome). For instance, based on the annotation, the predictive cancer model may determine presence or absence of mutation in a particular TERT promoter or splice site region.

The processing system 200 may also use the annotations to generate additional features during computational analysis across a greater number of biological categories. As an example, the processing system 200 determines features indicating maximum AF in a particular TERT promoter or splice site region. Another additional feature may be a total number of small variants in a set of one or more TERT promoter or splice site regions. This concept is extendable to other features having the same or different measures (e.g., max AF or mean AF), focused on the presence or absence of variants relevant to other genomic conditions.

XI. D. Example Predictions Using Small Variant Features

Figure 35B:
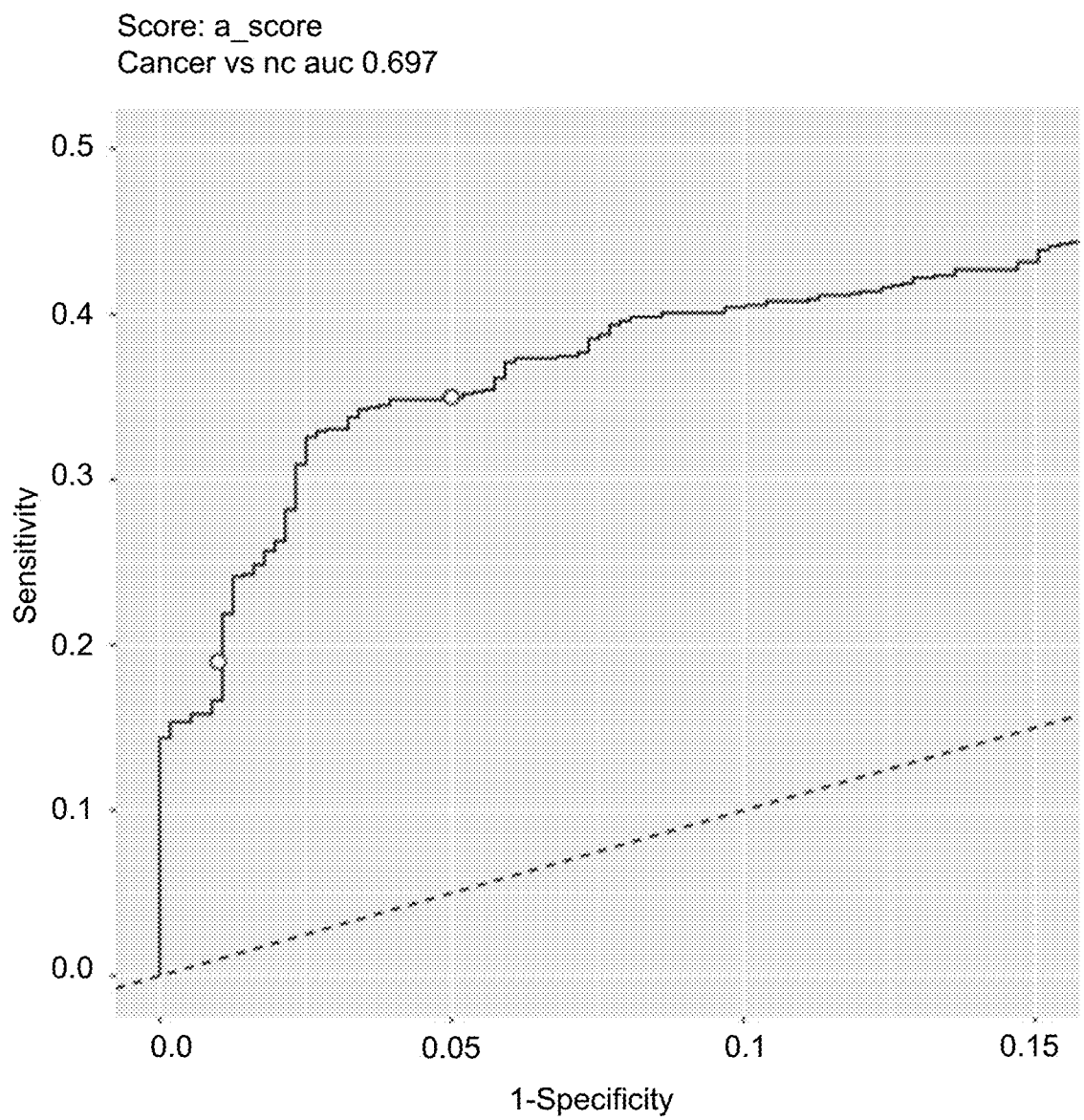
FIG. 35B depicts a receiver operating characteristic (ROC) curve of the specificity and sensitivity of a predictive cancer model that predicts the presence of cancer using a first set of small variant features according to one embodiment.

FIG. 35B depicts a receiver operating characteristic (ROC) curve of the specificity and sensitivity of a predictive cancer model that predicts the presence of cancer using a first set of small variant features according to one embodiment. Specifically the predictive cancer model outputs a score, hereafter referred to as an "A_score" that indicates the presence or absence of cancer. The total area under the curve (AUC) of the ROC curve is 0.697. Given that the goal is to achieve a sensitivity given a set specificity (e.g., 95% or 99% specificity), FIG. 35B depicts the performance of a predictive cancer model in a 85%-100% specificity range. In this example, the first set of small variant features provided to the predictive cancer model include: a total number of somatic variants and a total number of nonsynonymous variants. The ROC curve indicates a 35% sensitivity at a 95% specificity and a ~19% sensitivity at a 99% specificity. Proceeding from 99% specificity to 95% specificity, the ROC curve increases non-linearly, thereby indicating that there are likely true positives detected in this sensitivity/specificity tradeoff In an embodiment, a small variant predictive cancer model at a 95% specificity uses the total number of non-synonymous variants as a feature and outputs an "A_score." The predictive cancer model has an average sensitivity of 47% detecting stage I/II/III cancers with greater than 25% 5-year mortality. The predictive cancer model has an average sensitivity of 80% detecting stage IV cancers with greater than 25% 5-year mortality. The predictive cancer model has an average sensitivity of 8% detecting stage I/II/III cancers with less than 25% 5-year mortality. The predictive cancer model has an average sensitivity of 50% detecting stage IV cancers with less than 25% 5-year mortality.

Figure 35C:
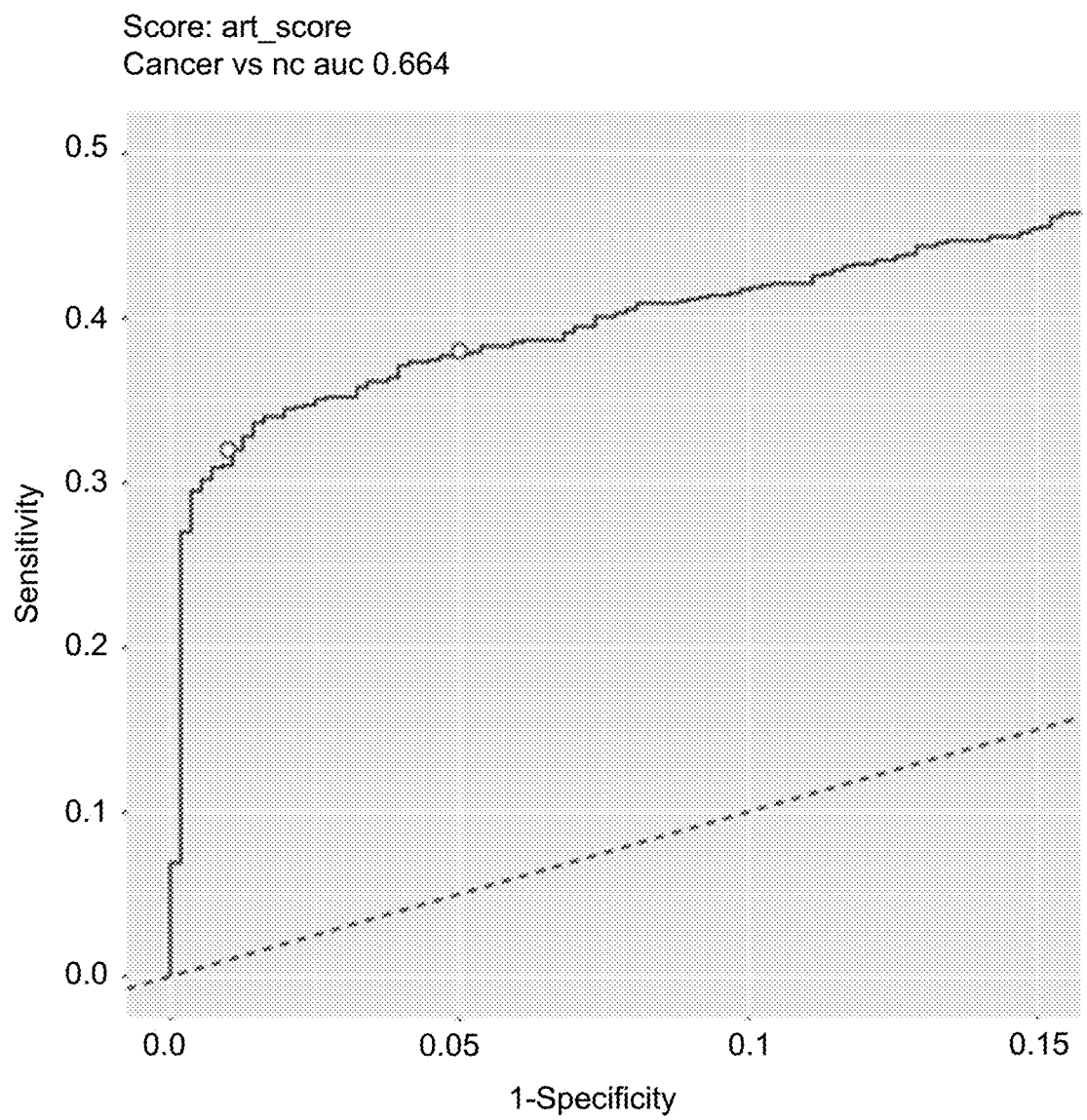
FIG. 35C depicts a ROC curve of the specificity and sensitivity of a predictive cancer model that predicts the presence of cancer using a second set of small variant features according to one embodiment.

FIG. 35C depicts a ROC curve of the specificity and sensitivity of a predictive cancer model that predicts the presence of cancer using a second set of small variant features according to one embodiment. Specifically the predictive cancer model outputs a score, hereafter referred to as a variant gene score that indicates the presence or absence of cancer. The total AUC of the ROC curve is 0.664. FIG. 35C depicts the performance of the predictive cancer model in a 85%-100% specificity range. In this example, the second set of small variant features provided to the predictive cancer model include an AF of somatic variants per gene. Here, the AF of somatic variants per gene represents the maximum AF of a somatic variant in each gene. Therefore, a total of 500 values of the maximum AF of somatic variants per gene (corresponding to 500 genes) were provided as feature values to the predictive cancer model. The ROC curve indicates a ~38% sensitivity at a 95% specificity and a ~31% sensitivity at a 99% specificity. This represents an improvement in comparison to the results of the predictive cancer model shown in FIG. 35B.

Figure 35D:
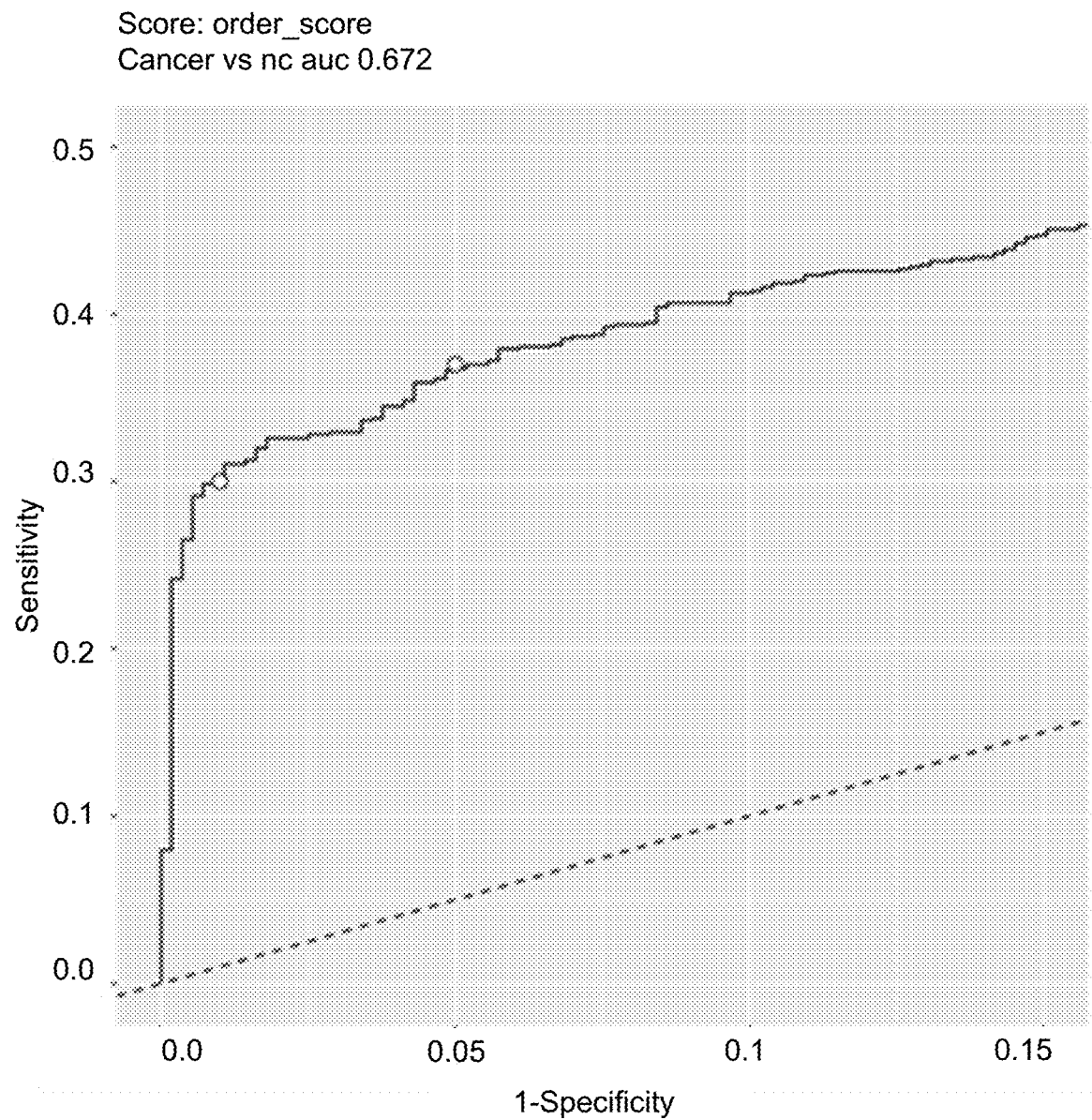
FIG. 35D depicts a ROC curve of the specificity and sensitivity of a predictive cancer model that predicts the presence of cancer using a third set of small variant features according to one embodiment.

FIG. 35D depicts a ROC curve of the specificity and sensitivity of a predictive cancer model that predicts the presence of cancer using a third set of small variant features according to one embodiment. Specifically the predictive cancer model outputs a score, hereafter referred to as an Order score that indicates the presence or absence of cancer. The total AUC of the ROC curve is 0.672. FIG. 35D depicts the performance of the predictive cancer model in a 85%-100% specificity range. In this example, the small variant features of the predictive cancer model include the top 6 ranked order according to AF of somatic variants. The ROC curve indicates a ~37% sensitivity at a 95% specificity and a ~30% sensitivity at a 99% specificity. Again, this represents an improvement in comparison to the results of the predictive cancer model shown in FIG. 35B.

XII. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
   generating a plurality of candidate variants of a cell free nucleic acid sample of a subject;
   for each position of a plurality of positions of a reference allele:
      determining a first depth and a first alternate depth of first sequence reads from the cell free nucleic acid sample, wherein the first sequence reads are obtained from a sample of blood, whole blood, plasma, serum, urine, cerebrospinal fluid, feces, saliva, tears, a tissue biopsy, pleural fluid, pericardial fluid, or peritoneal fluid of the subject, and wherein the first depth represents a total number of the first sequence reads at the position, and wherein the first alternate depth represents a number of the first sequence reads having a mutation at the position based on the reference allele; and determining a second depth and a second alternate depth of second sequence reads from a genomic nucleic acid sample of the subject, wherein the second sequence reads are obtained from a sample of white blood cells or tumor cells of a tumor biopsy of the subject, and wherein the second depth represents a total number of the second sequence reads at the position, and wherein the second alternate depth represents a number of the second sequence reads having a mutation at the position based on the reference allele;

determining a first likelihood of true alternate frequency of the cell free nucleic acid sample by applying a Bayesian hierarchical model to model the first alternate depths using aa first function parameterized by the first depths and the true alternate frequency of the cell free nucleic acid sample and (ii) a first noise level of mutations with respect to healthy cell free nucleic acid samples, wherein the first noise level describes expected noise rates per position of the first sequence reads;

determining a second likelihood of true alternate frequency of the genomic nucleic acid sample by applying the Bayesian hierarchical model to model the second alternate depths using aa second function parameterized by the second depths and the true alternate frequency of the genomic nucleic acid sample and (ii) a second noise level of mutations with respect to healthy genomic nucleic acid samples, wherein the second noise level describes expected noise rates per position of the second sequence reads;

filtering the plurality of candidate variants at least by a machine learning model using the first likelihood and the second likelihood to determine a probability that the true alternate frequency of the cell free nucleic acid sample is greater than a function of the true alternate frequency of the genomic nucleic acid sample; and outputting the filtered candidate variants.

2. The method of claim 1, wherein the first function is a Poisson distribution function parameterized by a product of one of the first depths and the true alternate frequency of the cell free nucleic acid sample, and wherein the second function is another Poisson distribution function parameterized by another product of one of the second depths and the true alternate frequency of the genomic nucleic acid sample.

3. The method of claim 1, wherein the probability represents a confidence level that mutations from the first sequence reads from the cell free nucleic acid sample are not found in the second sequence reads from the genomic nucleic acid sample of the subject.

4. The method of claim 1, further comprising:
responsive to determining that the probability is greater than one or more parameters, determining that at least some mutations from the first sequence reads from the cell free nucleic acid sample are not found in the second sequence reads from the genomic nucleic acid sample of the subject.

5. The method of claim 1, wherein determining the probability further comprises:
determining the probability that the true alternate frequency of the cell free nucleic acid sample is greater than the true alternate frequency of the genomic nucleic acid sample multiplied by one or more parameters.

6. The method of claim 1, wherein determining the probability comprises:
determining a joint likelihood of the first likelihood and the second likelihood, the first likelihood and the second likelihood being conditionally independent given the first sequence reads and the second sequence reads.

7. The method of claim 1, wherein determining the probability comprises numerically approximating a joint likelihood of the first likelihood and the second likelihood by:
determining a cumulative sum of one of the first and second likelihoods; and
determining an integral of the other of the first and second likelihoods.

8. The method of claim 1, wherein determining the probability is further based on a first parameter determined using a third function taking as input an alternate frequency of healthy genomic nucleic acid samples.

9. The method of claim 8, wherein the third function is defined by criteria to guard against loss of heterozygosity events in sequence reads.

10. The method of claim 9, wherein the third function is a non-linear function.

11. The method of claim 9, wherein the criteria indicates a value of 3 for the first parameter and a lower threshold value of ⅓ for the alternate frequency of the healthy genomic nucleic acid samples.

12. The method of claim 1, wherein determining the probability is further based on a first parameter determined using a third function taking as input (i) one of the second alternate depths of the second sequence reads from the genomic nucleic acid sample, (ii) a reference depth of the genomic nucleic acid sample, and (iii) a model of noise levels of mutations with respect to healthy genomic nucleic acid samples.

13. The method of claim 12, wherein determining the probability is further based on a second parameter, the first and second parameters determined empirically by cross-validating with sets of cell free nucleic acid samples and genomic nucleic acid samples of a plurality of individuals.

14. The method of claim 13, wherein the first parameter has a value between 1 and 5, inclusive, and wherein the second parameter has another value between 0.5 and 1.

15. The method of claim 13, wherein the cross-validating includes applying candidate parameter values derived using samples associated with a plurality of types of diseases to test another sample associated with a different type of disease.

16. The method of claim 1, further comprising:
determining the first noise level of mutations with respect to the healthy cell free nucleic acid samples using a third function parameterized by first parameters; and
determining the second noise level of mutations with respect to the healthy genomic nucleic acid samples using a fourth function parameterized by second parameters.

17. The method of claim 16, wherein modeling the first alternate depths includes adding the first noise level to an output of the first function, and wherein modeling the second alternate depths includes adding the second noise level to another output of the second function.

18. The method of claim 16, wherein the first and second parameters represent parameters of distributions that encode noise levels of mutations with respect to a given position of a sequence read.

19. The method of claim 16, wherein the third and fourth functions are each a negative binomial function parameterized by a mean rate and dispersion parameter.

20. The method of claim 16, wherein the third and fourth functions are a same type of function and parameterized by same types of parameters.

21. The method of claim 16, wherein the first parameters are derived using a first machine learning model trained using a set of cell free nucleic acid samples, and the second parameters are derived using a second machine learning model trained using a set of genomic nucleic acid samples.

22. The method of claim 21, wherein the set of genomic nucleic acid samples are from white blood cells.

23. The method of claim 21, wherein the first and second machine learning models are Bayesian Hierarchical models.

24. The method of claim 21, wherein the first and second machine learning models are a same type of model.

25. The method of claim 1, further comprising:
collecting or having collected the cell free nucleic acid sample from a blood sample of the subject; and
performing enrichment on the cell free nucleic acid sample to generate the first sequence reads.

26. The method of claim 1, wherein the first sequence reads are obtained from an isolate of cells from blood including at least CD4+cells of the subject.

27. A computer-product comprising a non-transitory computer readable medium storing a plurality of instructions for controlling a computer system to:
generate a plurality of candidate variants of a cell free nucleic acid sample of a subject;
for each position of a plurality of positions of a reference allele:
determine a first depth and a first alternate depth of first sequence reads from the cell free nucleic acid sample, wherein the first sequence reads are obtained from a sample of blood, whole blood, plasma, serum, urine, cerebrospinal fluid, feces, saliva, tears, a tissue biopsy, pleural fluid, pericardial fluid, or peritoneal fluid of the subject, and wherein the first depth represents a total number of the first sequence reads at the position, and wherein the first alternate depth represents a number of the first sequence reads having a mutation at the position based on the reference allele; and
determine a second depth and a second alternate depth of second sequence reads from a genomic nucleic acid sample of the subject, wherein the second sequence reads are obtained from a sample of white blood cells or tumor cells of a tumor biopsy of the subject, and wherein the second depth represents a total number of the second sequence reads at the position, and wherein the second alternate depth represents a number of the second sequence reads having a mutation at the position based on the reference allele;
determine a first likelihood of true alternate frequency of the cell free nucleic acid sample by applying a Bayesian hierarchical model to model the first alternate depths using aa first function parameterized by the first depths and the true alternate frequency of the cell free nucleic acid sample and (ii) a first noise level of mutations with respect to healthy cell free nucleic acid samples wherein the first noise level describes expected noise rates per position of the first sequence reads;
determine a second likelihood of true alternate frequency of the genomic nucleic acid sample by applying the Bayesian hierarchical model to model the second alternate depths using aa second function parameterized by the second depths and the true alternate frequency of the genomic nucleic acid sample and (ii) a second noise level of mutations with respect to healthy genomic nucleic acid samples, wherein the second noise level describes expected noise rates per position of the second sequence reads;
filter the plurality of candidate variants at least by a machine learning model using the first likelihood and the second likelihood to determine a probability that the true alternate frequency of the cell free nucleic acid sample is greater than a function of the true alternate frequency of the genomic nucleic acid sample; and
output the filtered candidate variants.

28. A system comprising a computer processor and a memory, the memory storing computer program instructions that when executed by the computer processor cause the processor to perform steps comprising:
generating a plurality of candidate variants of a cell free nucleic acid sample of a subject;
for each position of a plurality of positions of a reference allele:
determining a first depth and a first alternate depth of first sequence reads from the cell free nucleic acid sample, wherein the first sequence reads are obtained from a sample of blood, whole blood, plasma, serum, urine, cerebrospinal fluid, feces, saliva, tears, a tissue biopsy, pleural fluid, pericardial fluid, or peritoneal fluid of the subject, and wherein the first depth represents a total number of the first sequence reads at the position, and wherein the first alternate depth represents a number of the first sequence reads having a mutation at the position based on the reference allele; and
determining a second depth and a second alternate depth of second sequence reads from a genomic nucleic acid sample of the subject, wherein the second sequence reads are obtained from a sample of white blood cells or tumor cells of a tumor biopsy of the subject, and wherein the second depth represents a total number of the second sequence reads at the position, and wherein the second alternate depth represents a number of the second sequence reads having a mutation at the position based on the reference allele;
determining a first likelihood of true alternate frequency of the cell free nucleic acid sample by applying a Bayesian hierarchical model to model the first alternate depths using (i) a first function parameterized by the first depths and the true alternate frequency of the cell free nucleic acid sample and (ii) a first noise level of mutations with respect to healthy cell free nucleic acid samples, wherein the first noise level describes expected noise rates per position of the first sequence reads;
determining a second likelihood of true alternate frequency of the genomic nucleic acid sample by applying the Bayesian hierarchical model to model the second alternate depths using aa second function parameterized by the second depths and the true alternate frequency of the genomic nucleic acid sample and (ii) a second noise level of mutations with respect to healthy genomic nucleic acid samples, wherein the second noise level describes expected noise rates per position of the second sequence reads;

filtering the plurality of candidate variants at least by a machine learning model using the first likelihood and the second likelihood to determine a probability that the true alternate frequency of the cell free nucleic acid sample is greater than a function of the true alternate frequency of the genomic nucleic acid sample; and outputting the filtered candidate variants.

* * * * *

UNITED STATES PATENT AND TRADEMARK OFFICE
CERTIFICATE OF CORRECTION

| | | |
|---|---|---|
| PATENT NO. | : 11,961,589 B2 | Page 1 of 1 |
| APPLICATION NO. | : 16/201912 | |
| DATED | : April 16, 2024 | |
| INVENTOR(S) | : Blocker et al. | |

It is certified that error appears in the above-identified patent and that said Letters Patent is hereby corrected as shown below:

In the Claims

In Column 69, in Claim 1, Line 25, delete "aa" and insert -- (i) a --, therefor.

In Column 69, in Claim 1, Line 35, delete "aa" and insert -- (i) a --, therefor.

In Column 71, in Claim 26, Line 30, delete "CD+cells" and insert -- CD+ cells --, therefor.

In Column 71, in Claim 27, Line 64, delete "aa" and insert -- (i) a --, therefor.

In Column 72, in Claim 27, Line 1, delete "samples" and insert -- samples, --, therefor.

In Column 72, in Claim 27, Line 6, delete "aa" and insert -- (i) a --, therefor.

In Column 72, in Claim 28, Line 64, delete "aa" and insert -- (i) a --, therefor.

Signed and Sealed this
Twenty-fifth Day of June, 2024

Katherine Kelly Vidal
*Director of the United States Patent and Trademark Office*